(12) United States Patent
Takahashi et al.

(10) Patent No.: US 10,077,429 B2
(45) Date of Patent: Sep. 18, 2018

(54) METHOD OF EFFICIENTLY ESTABLISHING INDUCED PLURIPOTENT STEM CELLS

(71) Applicant: KYOTO UNIVERSITY, Kyoto-shi, Kyoto (JP)

(72) Inventors: Kazutoshi Takahashi, Kyoto (JP); Koji Tanabe, Kyoto (JP); Shinya Yamanaka, Kyoto (JP)

(73) Assignee: Kyoto University, Kyoto (JP)

( * ) Notice: Subject to any disclaimer, the term of this patent is extended or adjusted under 35 U.S.C. 154(b) by 254 days.

(21) Appl. No.: 14/438,106

(22) PCT Filed: Oct. 23, 2013

(86) PCT No.: PCT/JP2013/079474
§ 371 (c)(1),
(2) Date: Apr. 23, 2015

(87) PCT Pub. No.: WO2014/065435
PCT Pub. Date: May 1, 2014

(65) Prior Publication Data
US 2015/0252330 A1    Sep. 10, 2015

Related U.S. Application Data

(60) Provisional application No. 61/717,250, filed on Oct. 23, 2012.

(51) Int. Cl.
| | | |
|---|---|---|
| *C12N 5/02* | (2006.01) | |
| *C12N 15/63* | (2006.01) | |
| *C07K 14/00* | (2006.01) | |
| *C07H 21/04* | (2006.01) | |
| *C12N 5/074* | (2010.01) | |

(52) U.S. Cl.
CPC ............ *C12N 5/0696* (2013.01); *C12N 15/63* (2013.01); *C12N 2501/16* (2013.01); *C12N 2501/405* (2013.01); *C12N 2501/60* (2013.01); *C12N 2501/602* (2013.01); *C12N 2501/603* (2013.01); *C12N 2501/604* (2013.01); *C12N 2501/606* (2013.01); *C12N 2506/00* (2013.01); *C12N 2506/1307* (2013.01); *C12N 2510/00* (2013.01)

(58) Field of Classification Search
CPC .............. C12N 5/0696; C12N 2501/60; C12N 2506/00; C12N 15/63; C07H 21/04
USPC ................... 435/377, 455; 530/350; 536/23.5
See application file for complete search history.

(56) References Cited

U.S. PATENT DOCUMENTS

| | | |
|---|---|---|
| 8,048,999 B2 | 11/2011 | Yamanaka et al. |
| 2009/0068742 A1 | 3/2009 | Yamanaka |
| 2013/0267030 A1 | 10/2013 | Yamanaka et al. |

FOREIGN PATENT DOCUMENTS

| | | |
|---|---|---|
| JP | 2010-537634 A | 12/2010 |
| WO | WO 2007/069666 A1 | 6/2007 |
| WO | WO 2008/118820 A2 | 10/2008 |
| WO | WO 2009/032194 A1 | 3/2009 |
| WO | WO 2009/157593 A1 | 12/2009 |
| WO | WO 2010/007031 A2 | 1/2010 |
| WO | WO 2010/117879 A1 | 10/2010 |
| WO | WO 2011/091270 A2 | 7/2011 |
| WO | WO 2011/102531 A1 | 8/2011 |
| WO | WO 2012/074117 A1 | 6/2012 |
| WO | WO 2012/141181 A1 | 10/2012 |

OTHER PUBLICATIONS

Chin et al., 2014, US 20140227300 A1, effective filing date Jun. 27, 2011.*
Watarai et al., 2011, US 20110231944 A1.*
Li et al., 2014, Journal of Hematology & Oncology, 7:50, p. 1-18.*
Sommer et al., 2013, J. Cell. Physiol., vol. 228, p. 267-275.*
Zhang et al., 2012, Cell Cycle, vol. 11, No. 24, p. 1-9.*
Pandey, Prativa, 2007, Abstracts, 59th Southeast regional Meeting of the American Chemical Society, Greenville, SC, United States, GEN-671, Publisher: American Chemical Society, Washington D.C.*
Bryan et al., 2013, http://www.elsevierblogs.com/currentcomments/?p=962, Implications of protein fold switching, p. 1-4.*
Maqbool et al., 2015, Biochemical Society Transactions, vol. 43, No. 5, p. 1011-1017.*
Choi et al., *Developmental Biology*, 304(2): 735-744 (2007).
Chang et al., *PLoS Computational Biology*, 7(12): e1002300 (2011).
Hong et al., *Nature*, 460: 1132-1135 (2009).
Hong et al., *Jikken Igaku* (*Experimental Medicine*), "Suppression of iPS cell generation by p53 pathway," 28(3): 378-382 (2010).
Katoh et al., *International Journal of Molecular Medicine*, 17: 795-799 (2006).
Maekawa et al., *Nature*, 474: 225-229 (2011).
Rao et al., *Biology of Reproduction*, 71: 1772-1778 (2004).
Richards et al., *Stem Cells*, 22: 51-64 (2004).
Takahashi et al., *Cell*, 126: 663-676 (2006).
Takahashi et al., *Cell*, 131: 861-872 (2007).
Wang et al., "Foxo3a Is Involved in the Proper Generation of Induced Pluripotent Stem Cell (iPSC)," *J. Neuroimmune Pharmacol.*, 7 (Suppl 1): S58-S59 (2012).
Wang et al., *Biochemical and Biophysical Research Communications*, 330: 934-942 (2005).
Yu et al., *Science*, 318: 1917-1920 (2007).
Japanese Patent Office, International Search Report in International Application No. PCT/JP2013/079474 (dated Dec. 3, 2013).
Gadue et al., "Wnt and TGF-β signaling are required for the induction of an in vitro model of primitive streak formation using embryonic stem cells," *Proc. Natl. Acad. Sci. U.S.A.*, 103(45): 16806-16811 (2006).

* cited by examiner

*Primary Examiner* — Shin Lin Chen
(74) *Attorney, Agent, or Firm* — Leydig, Voit & Mayer, Ltd.

(57) ABSTRACT

The present invention provides a method of improving iPS cell establishment efficiency, comprising contacting a protein involved in primitive streak (PrS) formation, preferably Foxh1, or a nucleic acid that encodes the same with a somatic cell in a nuclear reprogramming step. Also provided is a method of producing an iPS cell, comprising contacting the protein involved in PrS formation or a nucleic acid that encodes the same, and nuclear reprogramming substance(s) with a somatic cell.

12 Claims, 23 Drawing Sheets
(20 of 23 Drawing Sheet(s) Filed in Color)
Specification includes a Sequence Listing.

SEQUENCE LISTING

<160> NUMBER OF SEQ ID NOS: 95

<210> SEQ ID NO 1
<211> LENGTH: 21
<212> TYPE: DNA
<213> ORGANISM: Artificial Sequence
<220> FEATURE:
<223> OTHER INFORMATION: Synthetic shRNA against FOXH1

<400> SEQUENCE: 1
cacctcctac ttgcctatct a                                              21

<210> SEQ ID NO 2

```
<211> LENGTH: 21
<212> TYPE: DNA
<213> ORGANISM: Artificial Sequence
<220> FEATURE:
<223> OTHER INFORMATION: Synthetic shRNA against FOXH1

<400> SEQUENCE: 2
gcctatctac actcccaatg t                                           21

<210> SEQ ID NO 3
<211> LENGTH: 21
<212> TYPE: DNA
<213> ORGANISM: Artificial Sequence
<220> FEATURE:
<223> OTHER INFORMATION: Synthetic shRNA against FOXH1

<400> SEQUENCE: 3
tgcagcctgt gaggctctta a                                           21

<210> SEQ ID NO 4
<211> LENGTH: 24
<212> TYPE: DNA
<213> ORGANISM: Artificial Sequence
<220> FEATURE:
<223> OTHER INFORMATION: Synthetic qRT-PCR primer for endogenous OCT3/4

<400> SEQUENCE: 4
gacaggggga ggggaggagc tagg                                        24

<210> SEQ ID NO 5
<211> LENGTH: 26
<212> TYPE: DNA
<213> ORGANISM: Artificial Sequence
<220> FEATURE:
<223> OTHER INFORMATION: Synthetic qRT-PCR primer for endogenous OCT3/4

<400> SEQUENCE: 5
cttccctcca accagttgcc ccaaac                                      26

<210> SEQ ID NO 6
<211> LENGTH: 23
<212> TYPE: DNA
<213> ORGANISM: Artificial Sequence
<220> FEATURE:
<223> OTHER INFORMATION: Synthetic qRT-PCR primer for total OCT3/4

<400> SEQUENCE: 6
ccccagggcc ccattttggt acc                                         23

<210> SEQ ID NO 7
<211> LENGTH: 26
<212> TYPE: DNA
<213> ORGANISM: Artificial Sequence
<220> FEATURE:
<223> OTHER INFORMATION: Synthetic qRT-PCR primer for total OCT3/4

<400> SEQUENCE: 7
acctcagttt gaatgcatgg gagagc                                      26

<210> SEQ ID NO 8
<211> LENGTH: 26
<212> TYPE: DNA
<213> ORGANISM: Artificial Sequence
<220> FEATURE:
<223> OTHER INFORMATION: Synthetic qRT-PCR primer for endogenous SOX2

<400> SEQUENCE: 8
```

```
gggaaatggg aggggtgcaa aagagg                                          26

<210> SEQ ID NO 9
<211> LENGTH: 26
<212> TYPE: DNA
<213> ORGANISM: Artificial Sequence
<220> FEATURE:
<223> OTHER INFORMATION: Synthetic qRT-PCR primer for endogenous SOX2

<400> SEQUENCE: 9
ttgcgtgagt gtggatggga ttggtg                                          26

<210> SEQ ID NO 10
<211> LENGTH: 24
<212> TYPE: DNA
<213> ORGANISM: Artificial Sequence
<220> FEATURE:
<223> OTHER INFORMATION: Synthetic qRT-PCR primer for total SOX2

<400> SEQUENCE: 10
ttcacatgtc ccagcactac caga                                            24

<210> SEQ ID NO 11
<211> LENGTH: 26
<212> TYPE: DNA
<213> ORGANISM: Artificial Sequence
<220> FEATURE:
<223> OTHER INFORMATION: Synthetic qRT-PCR primer for total SOX2

<400> SEQUENCE: 11
tcacatgtgt gagaggggca gtgtgc                                          26

<210> SEQ ID NO 12
<211> LENGTH: 24
<212> TYPE: DNA
<213> ORGANISM: Artificial Sequence
<220> FEATURE:
<223> OTHER INFORMATION: Synthetic qRT-PCR primer for NANOG

<400> SEQUENCE: 12
tggctgccgt ctctggctat agat                                            24

<210> SEQ ID NO 13
<211> LENGTH: 24
<212> TYPE: DNA
<213> ORGANISM: Artificial Sequence
<220> FEATURE:
<223> OTHER INFORMATION: Synthetic qRT-PCR primer for NANOG

<400> SEQUENCE: 13
aagcctccca atcccaaaca atac                                            24

<210> SEQ ID NO 14
<211> LENGTH: 20
<212> TYPE: DNA
<213> ORGANISM: Artificial Sequence
<220> FEATURE:
<223> OTHER INFORMATION: Synthetic qRT-PCR primer for KLF2

<400> SEQUENCE: 14
actcacacct gcagctacgc                                                 20

<210> SEQ ID NO 15
<211> LENGTH: 20
<212> TYPE: DNA
```

```
<213> ORGANISM: Artificial Sequence
<220> FEATURE:
<223> OTHER INFORMATION: Synthetic qRT-PCR primer for KLF2

<400> SEQUENCE: 15
gtctgagcgc gcaaacttcc                                                  20

<210> SEQ ID NO 16
<211> LENGTH: 30
<212> TYPE: DNA
<213> ORGANISM: Artificial Sequence
<220> FEATURE:
<223> OTHER INFORMATION: Synthetic qRT-PCR primer for KLF4

<400> SEQUENCE: 16
catgccagag gagcccaagc caaagagggg                                        30

<210> SEQ ID NO 17
<211> LENGTH: 30
<212> TYPE: DNA
<213> ORGANISM: Artificial Sequence
<220> FEATURE:
<223> OTHER INFORMATION: Synthetic qRT-PCR primer for KLF4

<400> SEQUENCE: 17
cgcaggtgtg ccttgagatg ggaactcttt                                        30

<210> SEQ ID NO 18
<211> LENGTH: 26
<212> TYPE: DNA
<213> ORGANISM: Artificial Sequence
<220> FEATURE:
<223> OTHER INFORMATION: Synthetic qRT-PCR primer for KLF5

<400> SEQUENCE: 18
tccaaattta cccaccaccc tgccag                                            26

<210> SEQ ID NO 19
<211> LENGTH: 26
<212> TYPE: DNA
<213> ORGANISM: Artificial Sequence
<220> FEATURE:
<223> OTHER INFORMATION: Synthetic qRT-PCR primer for KLF5

<400> SEQUENCE: 19
tccagtcgca gccttcccag gtacac                                            26

<210> SEQ ID NO 20
<211> LENGTH: 24
<212> TYPE: DNA
<213> ORGANISM: Artificial Sequence
<220> FEATURE:
<223> OTHER INFORMATION: Synthetic qRT-PCR primer for c-MYC

<400> SEQUENCE: 20
gccgccgcct cagagtgcat cgac                                              24

<210> SEQ ID NO 21
<211> LENGTH: 24
<212> TYPE: DNA
<213> ORGANISM: Artificial Sequence
<220> FEATURE:
<223> OTHER INFORMATION: Synthetic qRT-PCR primer for c-MYC

<400> SEQUENCE: 21
cgagtggagg gaggcgctgc gtag                                              24
```

<210> SEQ ID NO 22
<211> LENGTH: 26
<212> TYPE: DNA
<213> ORGANISM: Artificial Sequence
<220> FEATURE:
<223> OTHER INFORMATION: Synthetic qRT-PCR primer for MYCN

<400> SEQUENCE: 22
gtggtcactg tggagaagcg gcgttc                                          26

<210> SEQ ID NO 23
<211> LENGTH: 26
<212> TYPE: DNA
<213> ORGANISM: Artificial Sequence
<220> FEATURE:
<223> OTHER INFORMATION: Synthetic qRT-PCR primer for MYCN

<400> SEQUENCE: 23
gacgtgggga cgcctcgctc tttatc                                          26

<210> SEQ ID NO 24
<211> LENGTH: 24
<212> TYPE: DNA
<213> ORGANISM: Artificial Sequence
<220> FEATURE:
<223> OTHER INFORMATION: Synthetic qRT-PCR primer for MYCL1

<400> SEQUENCE: 24
accccctgga tccctgcatg aagc                                            24

<210> SEQ ID NO 25
<211> LENGTH: 26
<212> TYPE: DNA
<213> ORGANISM: Artificial Sequence
<220> FEATURE:
<223> OTHER INFORMATION: Synthetic qRT-PCR primer for MYCL1

<400> SEQUENCE: 25
tcctcatctt cctttcccc tgcagc                                           26

<210> SEQ ID NO 26
<211> LENGTH: 20
<212> TYPE: DNA
<213> ORGANISM: Artificial Sequence
<220> FEATURE:
<223> OTHER INFORMATION: Synthetic qRT-PCR primer for LIN28A

<400> SEQUENCE: 26
agtaagctgc acatggaagg                                                 20

<210> SEQ ID NO 27
<211> LENGTH: 20
<212> TYPE: DNA
<213> ORGANISM: Artificial Sequence
<220> FEATURE:
<223> OTHER INFORMATION: Synthetic qRT-PCR primer for LIN28A

<400> SEQUENCE: 27
cctgtctcct tttgatctgc                                                 20

<210> SEQ ID NO 28
<211> LENGTH: 26
<212> TYPE: DNA
<213> ORGANISM: Artificial Sequence
<220> FEATURE:

<223> OTHER INFORMATION: Synthetic qRT-PCR primer for LIN28B

<400> SEQUENCE: 28
aaaggccttg agtcaatacg ggtaac                                          26

<210> SEQ ID NO 29
<211> LENGTH: 26
<212> TYPE: DNA
<213> ORGANISM: Artificial Sequence
<220> FEATURE:
<223> OTHER INFORMATION: Synthetic qRT-PCR primer for LIN28B

<400> SEQUENCE: 29
ggccaccaca gttgtagcat ctatct                                          26

<210> SEQ ID NO 30
<211> LENGTH: 23
<212> TYPE: DNA
<213> ORGANISM: Artificial Sequence
<220> FEATURE:
<223> OTHER INFORMATION: Synthetic qRT-PCR primer for GDF3

<400> SEQUENCE: 30
gctacgtaaa ggagctgggc gtc                                             23

<210> SEQ ID NO 31
<211> LENGTH: 23
<212> TYPE: DNA
<213> ORGANISM: Artificial Sequence
<220> FEATURE:
<223> OTHER INFORMATION: Synthetic qRT-PCR primer for GDF3

<400> SEQUENCE: 31
ccctttcttt gatggcagac agg                                             23

<210> SEQ ID NO 32
<211> LENGTH: 23
<212> TYPE: DNA
<213> ORGANISM: Artificial Sequence
<220> FEATURE:
<223> OTHER INFORMATION: Synthetic qRT-PCR primer for LEFTY2

<400> SEQUENCE: 32
aaccgcacct ccctcatcga ctc                                             23

<210> SEQ ID NO 33
<211> LENGTH: 23
<212> TYPE: DNA
<213> ORGANISM: Artificial Sequence
<220> FEATURE:
<223> OTHER INFORMATION: Synthetic qRT-PCR primer for LEFTY2

<400> SEQUENCE: 33
gctccctctg caccgacacc tgt                                             23

<210> SEQ ID NO 34
<211> LENGTH: 24
<212> TYPE: DNA
<213> ORGANISM: Artificial Sequence
<220> FEATURE:
<223> OTHER INFORMATION: Synthetic qRT-PCR primer for GSC

<400> SEQUENCE: 34
cagctggccc ggaaagtgca cctc                                            24

```
<210> SEQ ID NO 35
<211> LENGTH: 24
<212> TYPE: DNA
<213> ORGANISM: Artificial Sequence
<220> FEATURE:
<223> OTHER INFORMATION: Synthetic qRT-PCR primer for GSC

<400> SEQUENCE: 35
ttctccggtg acgccttcga cgac                                          24

<210> SEQ ID NO 36
<211> LENGTH: 24
<212> TYPE: DNA
<213> ORGANISM: Artificial Sequence
<220> FEATURE:
<223> OTHER INFORMATION: Synthetic qRT-PCR primer for HEX

<400> SEQUENCE: 36
atcgacgcgc taaatggagg agac                                          24

<210> SEQ ID NO 37
<211> LENGTH: 24
<212> TYPE: DNA
<213> ORGANISM: Artificial Sequence
<220> FEATURE:
<223> OTHER INFORMATION: Synthetic qRT-PCR primer for HEX

<400> SEQUENCE: 37
ggagggcgaa cattgagagc tatc                                          24

<210> SEQ ID NO 38
<211> LENGTH: 24
<212> TYPE: DNA
<213> ORGANISM: Artificial Sequence
<220> FEATURE:
<223> OTHER INFORMATION: Synthetic qRT-PCR primer for SFRP5

<400> SEQUENCE: 38
accaagatct gcgcccagtg tgag                                          24

<210> SEQ ID NO 39
<211> LENGTH: 24
<212> TYPE: DNA
<213> ORGANISM: Artificial Sequence
<220> FEATURE:
<223> OTHER INFORMATION: Synthetic qRT-PCR primer for SFRP5

<400> SEQUENCE: 39
aatcagcttc cggtccccat tctc                                          24

<210> SEQ ID NO 40
<211> LENGTH: 24
<212> TYPE: DNA
<213> ORGANISM: Artificial Sequence
<220> FEATURE:
<223> OTHER INFORMATION: Synthetic qRT-PCR primer for DKK1

<400> SEQUENCE: 40
cgaggagaaa ttgaggaaac catc                                          24

<210> SEQ ID NO 41
<211> LENGTH: 24
<212> TYPE: DNA
<213> ORGANISM: Artificial Sequence
<220> FEATURE:
<223> OTHER INFORMATION: Synthetic qRT-PCR primer for DKK1
```

<210> SEQ ID NO 41
<400> SEQUENCE: 41
tgaccggaga caaacagaac cttc                                          24

<210> SEQ ID NO 42
<211> LENGTH: 24
<212> TYPE: DNA
<213> ORGANISM: Artificial Sequence
<220> FEATURE:
<223> OTHER INFORMATION: Synthetic qRT-PCR primer for GATA4

<400> SEQUENCE: 42
cgggtgttgg attttctcag atgc                                          24

<210> SEQ ID NO 43
<211> LENGTH: 24
<212> TYPE: DNA
<213> ORGANISM: Artificial Sequence
<220> FEATURE:
<223> OTHER INFORMATION: Synthetic qRT-PCR primer for GATA4

<400> SEQUENCE: 43
aaacccacgg tctaggccac agtg                                          24

<210> SEQ ID NO 44
<211> LENGTH: 24
<212> TYPE: DNA
<213> ORGANISM: Artificial Sequence
<220> FEATURE:
<223> OTHER INFORMATION: Synthetic qRT-PCR primer for TBX6

<400> SEQUENCE: 44
ctccttccgc ttccccgaga ccac                                          24

<210> SEQ ID NO 45
<211> LENGTH: 24
<212> TYPE: DNA
<213> ORGANISM: Artificial Sequence
<220> FEATURE:
<223> OTHER INFORMATION: Synthetic qRT-PCR primer for TBX6

<400> SEQUENCE: 45
gccccgcagt ttcctcttca cacg                                          24

<210> SEQ ID NO 46
<211> LENGTH: 18
<212> TYPE: DNA
<213> ORGANISM: Artificial Sequence
<220> FEATURE:
<223> OTHER INFORMATION: Synthetic qRT-PCR primer for HNF3-beta

<400> SEQUENCE: 46
ggagcggtga agatggaa                                                 18

<210> SEQ ID NO 47
<211> LENGTH: 20
<212> TYPE: DNA
<213> ORGANISM: Artificial Sequence
<220> FEATURE:
<223> OTHER INFORMATION: Synthetic qRT-PCR primer for HNF3-beta

<400> SEQUENCE: 47
tacgtgttca tgccgttcat                                               20

<210> SEQ ID NO 48
<211> LENGTH: 26

```
<212> TYPE: DNA
<213> ORGANISM: Artificial Sequence
<220> FEATURE:
<223> OTHER INFORMATION: Synthetic qRT-PCR primer for SOX17

<400> SEQUENCE: 48
cgctttcatg gtgtgggcta aggacg                                        26

<210> SEQ ID NO 49
<211> LENGTH: 26
<212> TYPE: DNA
<213> ORGANISM: Artificial Sequence
<220> FEATURE:
<223> OTHER INFORMATION: Synthetic qRT-PCR primer for SOX17

<400> SEQUENCE: 49
tagttggggt ggtcctgcat gtgctg                                        26

<210> SEQ ID NO 50
<211> LENGTH: 24
<212> TYPE: DNA
<213> ORGANISM: Artificial Sequence
<220> FEATURE:
<223> OTHER INFORMATION: Synthetic qRT-PCR primer for T

<400> SEQUENCE: 50
caaggcccag gtcccgaaag atgc                                          24

<210> SEQ ID NO 51
<211> LENGTH: 23
<212> TYPE: DNA
<213> ORGANISM: Artificial Sequence
<220> FEATURE:
<223> OTHER INFORMATION: Synthetic qRT-PCR primer for T

<400> SEQUENCE: 51
ggtgccgtgt gctcctccac tgc                                           23

<210> SEQ ID NO 52
<211> LENGTH: 20
<212> TYPE: DNA
<213> ORGANISM: Artificial Sequence
<220> FEATURE:
<223> OTHER INFORMATION: Synthetic qRT-PCR primer for KDR

<400> SEQUENCE: 52
tgatcggaaa tgacactgga                                               20

<210> SEQ ID NO 53
<211> LENGTH: 20
<212> TYPE: DNA
<213> ORGANISM: Artificial Sequence
<220> FEATURE:
<223> OTHER INFORMATION: Synthetic qRT-PCR primer for KDR

<400> SEQUENCE: 53
cacgactcca tgttggtcac                                               20

<210> SEQ ID NO 54
<211> LENGTH: 28
<212> TYPE: DNA
<213> ORGANISM: Artificial Sequence
<220> FEATURE:
<223> OTHER INFORMATION: Synthetic qRT-PCR primer for PAX6

<400> SEQUENCE: 54
```
acccattatc cagatgtgtt tgcccgag                                              28

<210> SEQ ID NO 55
<211> LENGTH: 26
<212> TYPE: DNA
<213> ORGANISM: Artificial Sequence
<220> FEATURE:
<223> OTHER INFORMATION: Synthetic qRT-PCR primer for PAX6

<400> SEQUENCE: 55
atggtgaagc tgggcatagg cggcag                                               26

<210> SEQ ID NO 56
<211> LENGTH: 24
<212> TYPE: DNA
<213> ORGANISM: Artificial Sequence
<220> FEATURE:
<223> OTHER INFORMATION: Synthetic qRT-PCR primer for MIXL1

<400> SEQUENCE: 56
cgcgctcacc ctgctccccg agtc                                                 24

<210> SEQ ID NO 57
<211> LENGTH: 25
<212> TYPE: DNA
<213> ORGANISM: Artificial Sequence
<220> FEATURE:
<223> OTHER INFORMATION: Synthetic qRT-PCR primer for MIXL1

<400> SEQUENCE: 57
ttggttcggg caggcagttc acatc                                                25

<210> SEQ ID NO 58
<211> LENGTH: 24
<212> TYPE: DNA
<213> ORGANISM: Artificial Sequence
<220> FEATURE:
<223> OTHER INFORMATION: Synthetic qRT-PCR primer for endogenous GLIS1

<400> SEQUENCE: 58
cacctcgccc acctgctgtc gctc                                                 24

<210> SEQ ID NO 59
<211> LENGTH: 24
<212> TYPE: DNA
<213> ORGANISM: Artificial Sequence
<220> FEATURE:
<223> OTHER INFORMATION: Synthetic qRT-PCR primer for endogenous GLIS1

<400> SEQUENCE: 59
gtgcgcccag ctcaagctcg gatg                                                 24

<210> SEQ ID NO 60
<211> LENGTH: 25
<212> TYPE: DNA
<213> ORGANISM: Artificial Sequence
<220> FEATURE:
<223> OTHER INFORMATION: Synthetic qRT-PCR primer for total GLIS1

<400> SEQUENCE: 60
tgcccccatc ctctcagagc cattc                                                25

<210> SEQ ID NO 61
<211> LENGTH: 26
<212> TYPE: DNA
<213> ORGANISM: Artificial Sequence

```
<220> FEATURE:
<223> OTHER INFORMATION: Synthetic qRT-PCR primer for total GLIS1

<400> SEQUENCE: 61
cagccatccg gtagcagtcg ccatag                                        26

<210> SEQ ID NO 62
<211> LENGTH: 20
<212> TYPE: DNA
<213> ORGANISM: Artificial Sequence
<220> FEATURE:
<223> OTHER INFORMATION: Synthetic qRT-PCR primer for G3PDH

<400> SEQUENCE: 62
accacagtcc atgccatcac                                               20

<210> SEQ ID NO 63
<211> LENGTH: 20
<212> TYPE: DNA
<213> ORGANISM: Artificial Sequence
<220> FEATURE:
<223> OTHER INFORMATION: Synthetic qRT-PCR primer for G3PDH

<400> SEQUENCE: 63
tccaccaccc tgttgctgta                                               20

<210> SEQ ID NO 64
<211> LENGTH: 23
<212> TYPE: DNA
<213> ORGANISM: Artificial Sequence
<220> FEATURE:
<223> OTHER INFORMATION: Synthetic qRT-PCR primer for FOXH1

<400> SEQUENCE: 64
ttggtgattc aggccgctcc ctc                                           23

<210> SEQ ID NO 65
<211> LENGTH: 23
<212> TYPE: DNA
<213> ORGANISM: Artificial Sequence
<220> FEATURE:
<223> OTHER INFORMATION: Synthetic qRT-PCR primer for FOXH1

<400> SEQUENCE: 65
gtccttgggc accttgcgga agc                                           23

<210> SEQ ID NO 66
<211> LENGTH: 23
<212> TYPE: DNA
<213> ORGANISM: Artificial Sequence
<220> FEATURE:
<223> OTHER INFORMATION: Synthetic qRT-PCR primer for LHX1

<400> SEQUENCE: 66
cggtctgcgg agttcgtggt tgt                                           23

<210> SEQ ID NO 67
<211> LENGTH: 23
<212> TYPE: DNA
<213> ORGANISM: Artificial Sequence
<220> FEATURE:
<223> OTHER INFORMATION: Synthetic qRT-PCR primer for LHX1

<400> SEQUENCE: 67
gacagccagt gcgcggatcc cag                                           23
```

<210> SEQ ID NO 68
<211> LENGTH: 24
<212> TYPE: DNA
<213> ORGANISM: Artificial Sequence
<220> FEATURE:
<223> OTHER INFORMATION: Synthetic qRT-PCR primer for CER1

<400> SEQUENCE: 68
ggacagtgcc cttcagccag acta                                           24

<210> SEQ ID NO 69
<211> LENGTH: 24
<212> TYPE: DNA
<213> ORGANISM: Artificial Sequence
<220> FEATURE:
<223> OTHER INFORMATION: Synthetic qRT-PCR primer for CER1

<400> SEQUENCE: 69
tggcaggcaa acagtgagag cagg                                           24

<210> SEQ ID NO 70
<211> LENGTH: 24
<212> TYPE: DNA
<213> ORGANISM: Artificial Sequence
<220> FEATURE:
<223> OTHER INFORMATION: Synthetic qRT-PCR primer for FOXF1

<400> SEQUENCE: 70
accctggacc ggcacaagaa actg                                           24

<210> SEQ ID NO 71
<211> LENGTH: 24
<212> TYPE: DNA
<213> ORGANISM: Artificial Sequence
<220> FEATURE:
<223> OTHER INFORMATION: Synthetic qRT-PCR primer for FOXF1

<400> SEQUENCE: 71
gccaaccgca gcgctgtgtc tttg                                           24

<210> SEQ ID NO 72
<211> LENGTH: 24
<212> TYPE: DNA
<213> ORGANISM: Artificial Sequence
<220> FEATURE:
<223> OTHER INFORMATION: Synthetic qRT-PCR primer for ID3

<400> SEQUENCE: 72
acttcgccct gcccacttga cttc                                           24

<210> SEQ ID NO 73
<211> LENGTH: 24
<212> TYPE: DNA
<213> ORGANISM: Artificial Sequence
<220> FEATURE:
<223> OTHER INFORMATION: Synthetic qRT-PCR primer for ID3

<400> SEQUENCE: 73
cagccactcc ttccacacct ccac                                           24

<210> SEQ ID NO 74
<211> LENGTH: 24
<212> TYPE: DNA
<213> ORGANISM: Artificial Sequence
<220> FEATURE:
<223> OTHER INFORMATION: Synthetic qRT-PCR primer for EVX1

```
<400> SEQUENCE: 74
ccgccttcac ccgagagcag attg                                          24

<210> SEQ ID NO 75
<211> LENGTH: 24
<212> TYPE: DNA
<213> ORGANISM: Artificial Sequence
<220> FEATURE:
<223> OTHER INFORMATION: Synthetic qRT-PCR primer for EVX1

<400> SEQUENCE: 75
ttgtccttca tgcgccggtt ctgg                                          24

<210> SEQ ID NO 76
<211> LENGTH: 24
<212> TYPE: DNA
<213> ORGANISM: Artificial Sequence
<220> FEATURE:
<223> OTHER INFORMATION: Synthetic qRT-PCR primer for BMP4

<400> SEQUENCE: 76
taccggcttc agtctgggga ggag                                          24

<210> SEQ ID NO 77
<211> LENGTH: 24
<212> TYPE: DNA
<213> ORGANISM: Artificial Sequence
<220> FEATURE:
<223> OTHER INFORMATION: Synthetic qRT-PCR primer for BMP4

<400> SEQUENCE: 77
ttcactggtc cctgggatgt tctc                                          24

<210> SEQ ID NO 78
<211> LENGTH: 22
<212> TYPE: DNA
<213> ORGANISM: Artificial Sequence
<220> FEATURE:
<223> OTHER INFORMATION: Synthetic Primer for analyzing methylome of
      OCT3/4 CR1

<400> SEQUENCE: 78 tttttggat gggtggagga ga                                             22

<210> SEQ ID NO 79
<211> LENGTH: 23
<212> TYPE: DNA
<213> ORGANISM: Artificial Sequence
<220> FEATURE:
<223> OTHER INFORMATION: Synthetic Primer for analyzing methylome of
      OCT3/4 CR1

<400> SEQUENCE: 79
caccattacc accaccatta aac                                           23

<210> SEQ ID NO 80
<211> LENGTH: 15
<212> TYPE: DNA
<213> ORGANISM: Artificial Sequence
<220> FEATURE:
<223> OTHER INFORMATION: Synthetic Primer for analyzing methylome of
      OCT3/4 CR1

<400> SEQUENCE: 80
atgggtggag gagag                                                    15
```

<210> SEQ ID NO 81
<211> LENGTH: 30
<212> TYPE: DNA
<213> ORGANISM: Artificial Sequence
<220> FEATURE:
<223> OTHER INFORMATION: Synthetic Primer for analyzing methylome of
      OCT3/4 CR2

<400> SEQUENCE: 81
gggtgtggag aaaaaatatt tgattttagg                                30

<210> SEQ ID NO 82
<211> LENGTH: 28
<212> TYPE: DNA
<213> ORGANISM: Artificial Sequence
<220> FEATURE:
<223> OTHER INFORMATION: Synthetic Primer for analyzing methylome of
      OCT3/4 CR2

<400> SEQUENCE: 82
ccaaacccat tcaaaaatta aacactta                                  28

<210> SEQ ID NO 83
<211> LENGTH: 15
<212> TYPE: DNA
<213> ORGANISM: Artificial Sequence
<220> FEATURE:
<223> OTHER INFORMATION: Synthetic Primer for analyzing methylome of
      OCT3/4 CR2

<400> SEQUENCE: 83
gggggtagga taatg                                                15

<210> SEQ ID NO 84
<211> LENGTH: 29
<212> TYPE: DNA
<213> ORGANISM: Artificial Sequence
<220> FEATURE:
<223> OTHER INFORMATION: Synthetic Primer for analyzing methylome of
      NANOG CR1

<400> SEQUENCE: 84
tttgtattat aatggttttg gtgagattg                                 29

<210> SEQ ID NO 85
<211> LENGTH: 24
<212> TYPE: DNA
<213> ORGANISM: Artificial Sequence
<220> FEATURE:
<223> OTHER INFORMATION: Synthetic Primer for analyzing methylome of
      NANOG CR1

<400> SEQUENCE: 85
cctactaacc cacccttata aatt                                      24

<210> SEQ ID NO 86
<211> LENGTH: 16
<212> TYPE: DNA
<213> ORGANISM: Artificial Sequence
<220> FEATURE:
<223> OTHER INFORMATION: Synthetic Primer for analyzing methylome of
      NANOG CR1

<400> SEQUENCE: 86
gttttggtga gattgg                                               16

<210> SEQ ID NO 87
<211> LENGTH: 19
<212> TYPE: DNA
<213> ORGANISM: Artificial Sequence
<220> FEATURE:
<223> OTHER INFORMATION: Synthetic Primer for analyzing methylome of
    OCT3/4 5' UTR

<400> SEQUENCE: 87
gtgggattgg ggagggaga                                               19

<210> SEQ ID NO 88
<211> LENGTH: 19
<212> TYPE: DNA
<213> ORGANISM: Artificial Sequence
<220> FEATURE:
<223> OTHER INFORMATION: Synthetic Primer for analyzing methylome of
    OCT3/4 5' UTR

<400> SEQUENCE: 88
cccctaaccc atcacctcc                                               19

<210> SEQ ID NO 89
<211> LENGTH: 24
<212> TYPE: DNA
<213> ORGANISM: Artificial Sequence
<220> FEATURE:
<223> OTHER INFORMATION: Synthetic Primer for analyzing methylome of
    OCT3/4 5' UTR

<400> SEQUENCE: 89
gtaagttttt attttattag gttt                                         24

<210> SEQ ID NO 90
<211> LENGTH: 25
<212> TYPE: DNA
<213> ORGANISM: Artificial Sequence
<220> FEATURE:
<223> OTHER INFORMATION: Synthetic ChIP-PCR primer for GLIS1 locus

<400> SEQUENCE: 90
acacagaacg ttgcaggagg gtatc                                        25

<210> SEQ ID NO 91
<211> LENGTH: 25
<212> TYPE: DNA
<213> ORGANISM: Artificial Sequence
<220> FEATURE:
<223> OTHER INFORMATION: Synthetic ChIP-PCR primer for GLIS1 locus

<400> SEQUENCE: 91
aaatgcctgc tgagtgttat tgctg                                        25

<210> SEQ ID NO 92
<211> LENGTH: 25
<212> TYPE: DNA
<213> ORGANISM: Artificial Sequence
<220> FEATURE:
<223> OTHER INFORMATION: Synthetic ChIP-PCR primer for GLIS1 locus

<400> SEQUENCE: 92
agggcctgag acagaacagc actgg                                        25

<210> SEQ ID NO 93
<211> LENGTH: 25
<212> TYPE: DNA

```
<213> ORGANISM: Artificial Sequence
<220> FEATURE:
<223> OTHER INFORMATION: Synthetic ChIP-PCR primer for GLIS1 locus

<400> SEQUENCE: 93
gacttcacca cctaccgtgc accag                                          25

<210> SEQ ID NO 94
<211> LENGTH: 25
<212> TYPE: DNA
<213> ORGANISM: Artificial Sequence
<220> FEATURE:
<223> OTHER INFORMATION: Synthetic ChIP-PCR primer for GLIS1 locus

<400> SEQUENCE: 94
ttgagtaatt tctggtgcga ggctg                                          25

<210> SEQ ID NO 95
<211> LENGTH: 25
<212> TYPE: DNA
<213> ORGANISM: Artificial Sequence
<220> FEATURE:
<223> OTHER INFORMATION: Synthetic ChIP-PCR primer for GLIS1 locus

<400> SEQUENCE: 95
gctttatggt ggtgtgcgtg tgtgc                                          25
```

METHOD OF EFFICIENTLY ESTABLISHING INDUCED PLURIPOTENT STEM CELLS

CROSS-REFERENCE TO RELATED APPLICATIONS

This patent application is the U.S. national phase of International Patent Application No. PCT/JP2013/079474, filed Oct. 23, 2013, which claims the benefit of U.S. Provisional Patent Application No. 61/717,250, filed on Oct. 23, 2012, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 20,292 bytes ASCII (Text) file named "720577Sequence-Listing.txt," created Apr. 22, 2015.

TECHNICAL FIELD OF THE INVENTION

The present invention relates to a method of improving the efficiency of establishment of induced pluripotent stem cells (hereinafter referred to as iPS cells) and a reagent therefor, more specifically to a factor [gene or protein] that improves the efficiency of establishment of iPS cells from a somatic cell and a method of improving the efficiency of establishment of iPS cells using the factor.

BACKGROUND OF THE INVENTION

In recent years, mouse and human iPS cells have been established one after another. Yamanaka et al. induced iPS cells by transferring the Oct3/4, Sox2, Klf4 and c-Myc genes into mouse and human fibroblasts, and forcing the cells to express the genes [1-3]. Thomson et al. produced human iPS cells using Nanog and Lin28 in place of Klf4 and c-Myc [4, 5]. However, the efficiency of iPS cell establishment was low at less than 1%.

Various efforts to improve the efficiency of iPS cell establishment have been made. For example, the present inventors reported that the inhibition of p53-p21 pathway remarkably increased the efficiency of iPS cell establishment [6, 7]. Maekawa et al. reported that the efficiency of iPS cell establishment was remarkably improved by transferring Glis1 along with Oct3/4, Sox2 and Klf4 into a somatic cell [8, 9]. In addition, it was found that Glis1 inhibits the proliferation of cells with imperfect reprogramming but only proliferates completely reprogrammed ones. They found that Glis1 was able to facilitate reprogramming by increasing the expressions of several genes that are reported to be involved in reprogramming.

CITED REFERENCES

1. WO 2007/069666
2. Takahashi, K. and Yamanaka, S., Cell, 126: 663-676 (2006)
3. Takahashi, K. et al., Cell, 131: 861-872 (2007)
4. WO 2008/118820
5. Yu, J. et al., Science, 318: 1917-1920 (2007)
6. WO 2009/157593
7. Hong, H. et al., Nature, 460: 1132-1135 (2009)
8. WO 2011/102531
9. Maekawa, M. et al., Nature, 474: 225-229 (2011)

SUMMARY OF THE INVENTION

It is an object of the present invention to provide a means of improving the efficiency of establishment of iPS cells, and a method of efficiently producing iPS cells using the means.

It is important to understand the process of direct reprogramming to facilitate induction of pluripotency. However, large numbers of non-reprogrammed cells during iPS cell generation inhibit accurate analyses of the reprogramming process. To overcome this issue, we used a pluripotent cell-specific surface antigen, TRA-1-60 to capture nascent reprogrammed cells. Comprehensive gene expression analyses revealed that TRA-1-60 (+) nascent human reprogrammed cells share the common gene expression signatures with primitive streak (PrS).

Another set of evidence connecting reprogramming and PrS arose from Glis1, which the present inventors previously reported as a maternal transcription factor enhancing iPSC generation. We found that Glis1 is highly expressed in PrS and mesoendoderm derived from human ES/iPS cells, but that it is barely expressed in undifferentiated human pluripotent stem cells. We also found that forced expression of Glis1 in human ES cells markedly increases expression of not only pluripotency-related genes but also PrS-related genes.

From these findings, the present inventors hypothesized that genes that play important roles in PrS formation during development may facilitate iPSC generation. To confirm this hypothesis, the present inventors focused on Forkhead box H1 (Foxh1), since knockout mouse experiments have shown that the transcription factor is essential for PrS formation.

Transduction of Foxh1 along with Oct3/4, Sox2, Klf4 and c-Myc markedly increased the number of iPSC colonies. The effect of Foxb1 was stronger than p53 shRNA and Glis1, two of the strongest known enhancers of reprogramming. Foxh1 and p53 shRNA showed synergistic effects, suggesting that Foxb1 enhances reprogramming independently of p53 inhibition. Stage-specific activation of Foxh1 demonstrated that Foxh1 facilitates reprogramming efficiency in late stages in contrast to Glis1 that facilitates reprogramming in earlier stages.

The present inventors conducted further investigations based on these findings, and have developed the present invention.

Accordingly, the present invention provides:

[1] A method of improving iPS cell establishment efficiency, comprising contacting a protein involved in primitive streak (PrS) formation or a nucleic acid that encodes the same with a somatic cell in a nuclear reprogramming step.

[2] The method according to [1] above, wherein the protein is selected from the group consisting of Foxh1, brachyury, goosecoid, Foxa2, eomesodermin, LHX1, Sox17, MIXL1, Lefty2, Nodal, Hand1, Wnt3, noggin, CER1, Foxf1, GATA4, GATA6, GSC, HESX1, HNF1A, HNF4A, OTX2, RNF111, Sox7, SP5, TBX6, Foxb1, Foxf2 and Foxg1.

[3] The method according to [1] above, wherein the protein is selected from the group consisting of Foxh1, brachyury, Foxa2, LHX1, Foxf1, Foxb1, Foxf2 and Foxg1.

[4] The method according to [1] above, wherein the protein is Foxh1.

[5] The method according to any one of [1] to [4] above, wherein the somatic cell is further contacted with Glis1 or a nucleic acid that encodes the same and/or a p53 inhibitor in a nuclear reprogramming step.

[6] An agent for improving iPS cell establishment efficiency comprising a protein involved in primitive streak (PrS) formation or a nucleic acid that encodes the same.
[7] The agent according to [6] above, wherein the protein is selected from the group consisting of Foxh1, brachyury, goosecoid, Foxa2, eomesodermin, LHX1, Sox17, MIXL1, GDF3, Lefty2, Nodal, Hand1, Wnt3, noggin, CER1, Foxf1, GATA4, GATA6, HESX1, HNF1A, HNF4A, OTX2, RNF111, Sox7, SP5, TBX6, Foxb1, Foxf2 and Foxg1.
[8] The agent according to [6] above, wherein the protein is selected from the group consisting of Foxh1, brachyury, Foxa2, LHX1, Foxf1, Foxb1, Foxf2 and Foxg1.
[9] The agent according to [6] above, wherein the protein is Foxh1.
[10] The agent according to any one of [6] to [9] above, further comprising Glis1 or a nucleic acid that encodes the same and/or a p53 inhibitor.
[11] A method of producing an iPS cell, comprising contacting a protein involved in primitive streak (PrS) formation or a nucleic acid that encodes the same, and nuclear reprogramming substance(s) with a somatic cell.
[12] The method according to [11] above, wherein the nuclear reprogramming substance(s) is(are) selected from the group consisting of members of the Oct family, members of the Sox family, members of the Klf family, members of the Myc family, members of the Lin family and the Nanog, as well as nucleic acids that encode the same.
[13] The method according to [11] above, wherein the nuclear reprogramming substances are Oct3/4, Sox2 and Klf4, or nucleic acids that encode the same.
[14] The method according to [11] above, wherein the nuclear reprogramming substances are Oct3/4, Sox2, Klf4 and L-Myc or c-Myc, or nucleic acids that encode the same.
[15] The method according to any one of [11] to [14] above, wherein the protein involved in primitive streak (PrS) formation is selected from the group consisting of a Fox family member, brachyury, goosecoid, eomesodermin, LHX1, Sox17, MIXL1, Lefty2, Nodal, Hand1, Wnt3, noggin, CER1, GATA4, GATA6, GSC, HESX1, HNF1A, HNF4A, OTX2, RNF111, Sox7, SP5 and TBX6.
[16] The method according to [15] above, wherein the Fox family member is selected from the group consisting of Foxa1, Foxa2, Foxa3, Foxb1, Foxc1, Foxc2, Foxd1, Foxd3, Foxd5, Foxe3, Foxf1, Foxf2, Foxg1, Foxh1, Foxi1, Foxi2, Foxj1, Foxj2, Foxj3, Foxk1, Foxk2, Foxl2, Foxm1, Foxn1, Foxan2, Foxn3, Foxn4, Foxo3, Foxo4, Foxp1, Foxp3, Foxp4, Foxr1, Foxr2 and Foxs1.
[17] The method according to any one of [11] to [14] above, wherein the protein is selected from the group consisting of Foxh1, brachyury, Foxa2, LHX1, Foxf1, Foxb1, Foxf2 and Foxg1.
[18] The method according to any one of [11] to [14] above, wherein the protein involved in primitive streak (PrS) formation is Foxh1.
[19] The method according to any one of [11] to [18] above, wherein the somatic cell is further contacted with Glis1 or a nucleic acid that encodes the same and/or a p53 inhibitor.
[20] An agent for inducing an iPS cell from a somatic cell, comprising a protein involved in primitive streak (PrS) formation or a nucleic acid that encodes the same, and nuclear reprogramming substance(s).
[21] The agent according to [20] above, wherein the nuclear reprogramming substance(s) is(are) selected from the group consisting of members of the Oct family, members of the Sox family, members of the Klf family, members of the Myc family, members of the Lin family and the Nanog, as well as nucleic acids that encode the same.
[22] The agent according to [20] above, wherein the nuclear reprogramming substances are Oct3/4, Sox2 and Klf4, or nucleic acids that encode the same.
[23] The agent according to [20] above, wherein the nuclear reprogramming substances are Oct3/4, Sox2, Klf4 and L-Myc or c-Myc, or nucleic acids that encode the same.
[24] The agent of any one of [20] to [23] above, wherein the protein involved in primitive streak (PrS) formation is selected from the group consisting of a Fox family member, brachyury, goosecoid, eomesodermin, LHX1, Sox17, MIXL1, GDF3, Lefty2, Nodal, Hand1, Wnt3, noggin, CER1, GATA4, GATA6, GSC, HESX1, HNF1A, HNF4A, OTX2, RNF111, Sox7, SP5 and TBX6.
[25] The method according to [24] above, wherein the Fox family member is selected from the group consisting of Foxa1, Foxa2, Foxa3, Foxb1, Foxc1, Foxc2, Foxd1, Foxd3, Foxd5, Foxe3, Foxf1, Foxf2, Foxg1, Foxh1, Foxi1, Foxi2, Foxj1, Foxj2, Foxj3, Foxk1, Foxk2, Foxl2, Foxm1, Foxn1, Foxan2, Foxn3, Foxn4, Foxo3, Foxo4, Foxp1, Foxp3, Foxp4, Foxr1, Foxr2 and Foxs1.
[26] The agent according to any one of [20] to [23] above, wherein the protein is selected from the group consisting of Foxh1, brachyury, Foxa2, LHX1, Foxf1, Foxb1, Foxf2 and Foxg1.
[27] The agent of any one of [20] to [23] above, wherein the protein involved in primitive streak (PrS) formation is Foxb1.
[28] The agent of any one of [20] to [27] above, further comprising Glis1 or a nucleic acid that encodes the same and/or a p53 inhibitor.
[29] An iPS cell containing an exogenous nucleic acid that encodes Foxb1.
[30] The iPS cell according to [29] above, wherein the exogenous nucleic acid is integrated in the genome.
[31] A method of producing a somatic cell, comprising performing a differentiation induction treatment on the iPS cell according to [29] or [30] above to cause the iPS cell to differentiate into a somatic cell.
[32] A method of producing a somatic cell, comprising the steps of:
(1) producing an iPS cell by the method according to any one of [11] to [19] above, and
(2) performing a differentiation induction treatment on the iPS cell obtained through the step (1) to cause the iPS cell to differentiate into a somatic cell.
[33] A use of a protein involved in primitive streak (PrS) formation or a nucleic acid that encodes the same for improving the efficiency of establishment of iPS cells.
[34] The use according to [33] above, wherein the protein is selected from the group consisting of Foxh1, brachyury, goosecoid, Foxa2, eomesodermin, LHX1, Sox17, MIXL1, Lefty2, Nodal, Hand1, Wnt3, noggin, CER1, GATA4, GATA6, GSC, HESX1, HNF1A, HNF4A, OTX2, RNF111, Sox7, SP5 and TBX6, Foxb1, Foxf2 and Foxg1.
[35] The use according to [33] above, wherein the protein is selected from the group consisting of Foxh1, brachyury, Foxa2, LHX1, Foxf1, Foxb1, Foxf2 and Foxg1.
[36] The use according to [33] above, wherein the protein is Foxh1.

[37] A use of a protein involved in primitive streak (PrS) formation or a nucleic acid that encodes the same in combination with nuclear reprogramming substance(s) for producing an iPS cell.

[38] The use according to [37] above, wherein the nuclear reprogramming substance(s) is(are) selected from the group consisting of members of the Oct family, members of the Sox family, members of the Klf family, members of the Myc family, members of the Lin28 family, and the Nanog, as well as nucleic acids that encode the same.

[39] The use according to [37] above, wherein the nuclear reprogramming substances are Oct3/4, Sox2 and Klf4, or nucleic acids that encode the same.

[40] The use according to [37] above, wherein the nuclear reprogramming substances are Oct3/4, Sox2, Klf4 and L-Myc or c-Myc, or nucleic acids that encode the same.

[41] The use according to any one of [37] to [40] above, wherein the protein involved in primitive streak (PrS) formation is selected from the group consisting of a Fox family member, brachyury, goosecoid, eomesodermin, LHX1, Sox17, MIXL1, Lefty2, Nodal, Hand1, Wnt3, noggin, CER1, GATA4, GATA6, GSC, HESX1, HNF1A, HNF4A, OTX2, RNF111, Sox7, SP5 and TBX6.

[42] The method according to [41] above, wherein the Fox family member is selected from the group consisting of Foxa1, Foxa2, Foxa3, Foxb1, Foxc1, Foxc2, Foxd1, Foxd3, Foxd5, Foxe3, Foxf1, Foxf2, Foxg1, Foxh1, Foxi1, Foxi2, Foxj1, Foxj2, Foxj3, Foxk1, Foxk2, Fox12, Foxm1, Foxn1, Foxan2, Foxn3, Foxn4, Foxo3, Foxo4, Foxp1, Foxp3, Foxp4, Foxr1, Foxr2 and Foxs1.

[43] The use according to any one of [37] to [40] above, wherein the protein is selected from the group consisting of Foxi1, brachyury, Foxa2, LHX1, Foxf1, Foxb1, Foxf2 and Foxg1.

[44] The use according to any one of [37] to [40] above, wherein the protein is Foxi1.

[45] A use of the iPS cell according to [29] or [30] above in producing a somatic cell.

[46] The iPS cell according to [29] or [30] above as a source of cells for producing a somatic cell.

Because the iPS cell establishment efficiency improving factor of the present invention can more efficiently establish iPS cells by means of 3 factors except c-Myc, compared to the strongest known enhancers of reprogramming, p53 shRNA and Glis1, as stated above, it is useful in, for example, applying iPS cells to regenerative medicine (e.g., preparation of safe human differentiated cells for transplantation).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 1A:
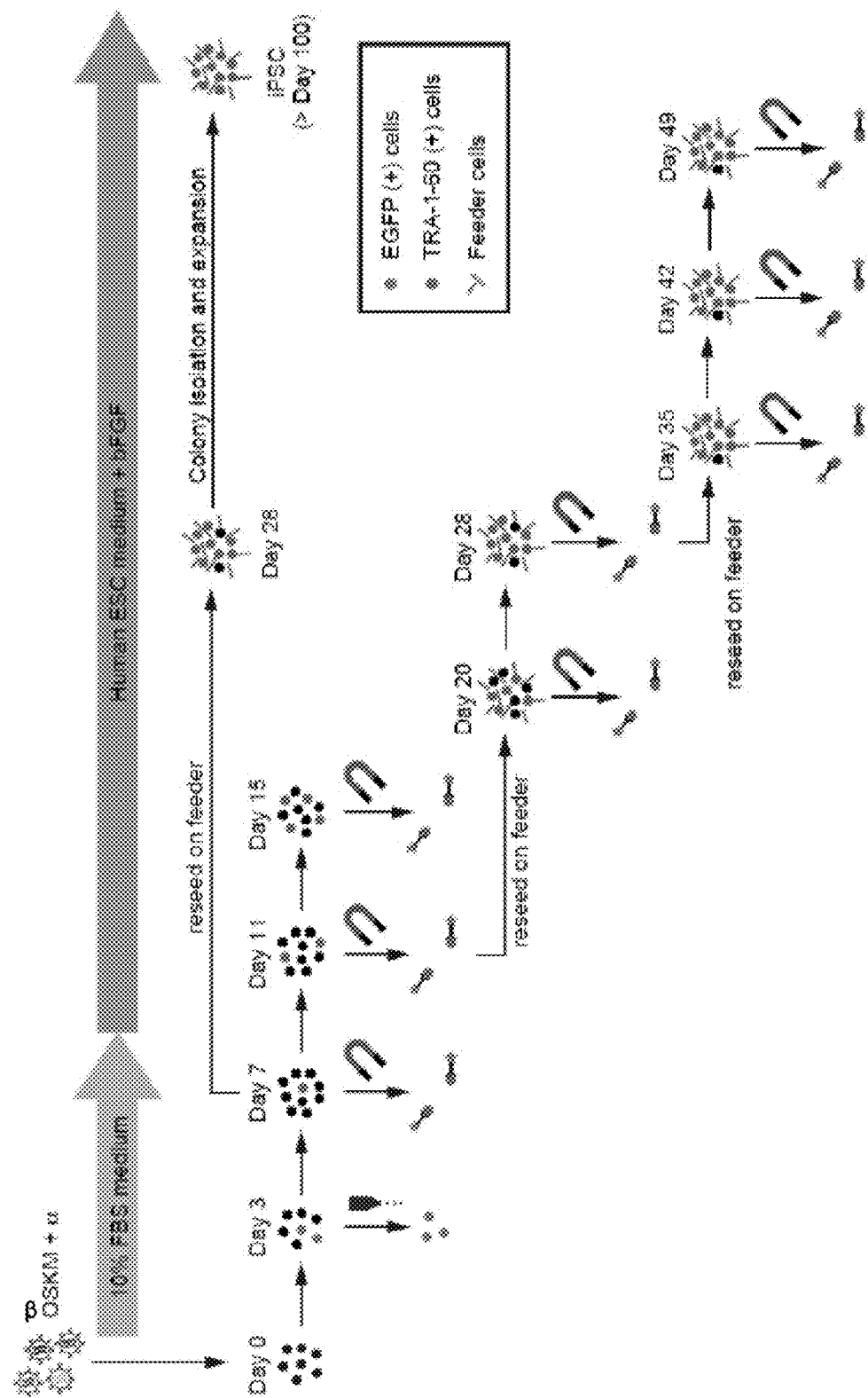
FIG. 1 shows that TRA-1-60 (+) cells are origins of human iPSC.

a. Scheme drawing of TRA-1-60 (+) intermediate cells throughout the human cellular reprogramming.

b. Percentage of TRA-1-60 (+) cells in post-transduction of Oct3/4, Sox2, Klf4 and c-Myc (OSKM) into human dermal fibroblasts (HDF).

c. The efficiencies of iPSC generation from single TRA-1-60 (+) cell in each time point. Colony forming efficiencies were estimated by the number of iPSC colony-formed wells in single TRA-1-60 (+) cell-sorted 96-well plates. N=3. Error bars indicate standard deviation.

d. The number of iPSC colonies at day 28 derived from $1 \times 10^5$ of TRA-1-60 (+) and (−) cells at day 7 post-transduction. N=3.

e. The expression of pluripotency-associated genes in TRA-1-60 (+) cells. Mean expression of three microarray data for each time point normalized by those of ESC are shown.

FIG. 2 shows characteristics of TRA-1-60 (+) intermediate cells.

a. PCA (principle component analysis) of nascent reprogrammed cells, parental HDF and ES/iPS cells (ESC/iPSC). All entities of microarray data were laid out with component 1 and 2. The arrow indicates the direction of reprogramming progression.

b. Classification of fluctuating genes during human cellular reprogramming. Gene ontology analyses of unidirectional (green) and transiently-fluctuated (red) gene clusters. We choose the top 10 biological terms with statistically significances.

c. Two categories of gene expression changes during reprogramming. The comparison of gene expression included in component 1 (unidirectional) and component 2 (transiently-fluctuated) with three germ layers such as PrS, ME, NE and EN.

d. PCA of nascent reprogrammed cells, parental HDF, ESC/iPSC and tri-lineage cells. All entities of microarray data were laid out with component 2 and 3. The arrow indicates the direction of reprogramming progression.

e. PCA of microarray expression data from TRA-1-60 (+) cells at each time point (d3-49), parental HDF and ESC/iPSC. Three microarray data are shown as each sample. The green arrow indicates a putative direction of the reprogramming progression. Both the PCA and hierarchical clustering were generated for the cell samples from averaged data in triplicate.

f. Classification of the fluctuating genes during human cellular reprogramming. Genes highly contributed for principal component 1 (Absolute contribution rate >0.6) were classified by gene ontology analyses. Green and red bars indicate top 10 categories of transiently-suppressed and activated genes, respectively. Shown are top 10 categories.

g. Comparison of global gene expression between TRA-1-60 (+) cells and various human tissues. Shown are the hierarchical clustering of global gene expression in parental HDF, TRA-1-60 (+) cells at indicated point, ESC/iPSC and ESC/iPSC-derived differentiated cells such as neuroectoderm (NE), endoderm (EN), mesoderm (ME) and primitive streak (PrS) and human tissues and tissue-derived cells such as peripheral blood mononuclear cell (PBMC), neural projenitor cell (NPC), epidermis (EDM), prostate epithelial cell (PrEC), normal bronchial epithelium (NHBE) adipose-tissue derived stem cell (ASC), astrocyte (HA) and dermal fibroblast (HDF).

h. The expression of mesenchymal and epithelial markers. Shown are the expression of representative mesenchymal and epithelial markers from microarray data.

FIG. 3 shows transient PrS-like status in nascent reprogrammed cells in the late stage of reprogramming.

a. Comparison of global gene expression between TRA-1-60 (+) cells and germ layers. Shown are the hierarchical clustering and heat map of global gene expression in parental HDF, TRA-1-60 (+) cells at indicated point, ESC/iPSC and differentiated cells such as EDM, PrS, EN, ME, and NE.

b. PrS-enriched genes transiently upregulated in TRA-1-60 (+) cells. Shown are percentages of ever-upregulated (black), ever-downregulated (blue), transiently-upregulated (red) and transiently downregulated (green) genes in enriched genes of endoderm (EN), mesoderm (ME), neuroectoderm (NE) or primitive streak (PrS).

c. The expression of representative primitive streak marker genes during human cellular reprogramming. Shown are the relative expression of selected primitive streak marker genes in TRA-1-60 (+) cells compared to parental HDF. In these analyses, the averages of three microarray data of each sample were used.

d. The expression and active histone marks of T gene during reprogramming, Blue circles indicate the relative expression of T compared to HDF. Red diamonds indicate the occupancy of H3K4me3 at the promoter region of T gene. N=3. Error bars indicate standard deviation.

e. Single cell expression of T. The expression of NANOG and T in single HDF, TRA-1-60 (+) cells on day 20 post-transduction and ESC. Each dot indicates one cell sample. The relative expressions were shown as ΔCt of qPCR.

f. Immunocytochemistry of T gene. The expression of NANOG (red) and T (green) in HDF, TRA-1-60 (+) cells on day 20, ESC and ESC-derived PrS were analyzed by immunocutochemistry. Nucleuses were visualized by staining with Hoechst 33342 (blue). Bars indicate 100 μm.

g. PCA of microarray expression data from TRA-1-60 (+) cells at each time point, parental cell lines (HDF, HA, ASC, NHBE and PrEC), ESC/iPSC and differentiated cells such as EN, NE, PrS and ME. Each arrow indicates a putative direction of the reprogramming progression. HA, astrocytes; NHBE, bronchial epithelium; PrEC, prostate epithelial cells; HDF, human dermal fibroblast; NE, neuroectoderm; ME, mesoderm; PrS, primitive streak; EN, endoderm.

FIG. 4 shows that nascent reprogrammed cells transiently express PrS-related genes.

a. Early-responding PrS-related genes in TRA-1-60 (+) cells during reprogramming.

b. Late-responding genes in TRA-1-60 (+) cells during reprogramming.

c. The signatures of TRA-1-60 (+) cells derived from various origins shifted to PrS. PCA of origins (closed circles), TRA-1-60 (+) cells (open circles) and PrS derived from human ESC/iPSC (square). All entities of microarray data were laid out with component 1 and 2. The arrow indicates the direction of reprogramming progression.

FIG. 5 shows that GLIS1 accelerates reprogramming with cell fate sifting to PrS and mesoderm.

a. Wild-type embryos at E5.5-6.5 were dissected and performed whole mount in situ hybridization with Glis1 cDNA probe as described previously (*Genes Dev* 15, 1242-1256, doi:10.1101/gad. 883901 (2001); *J Biol Chem* 277, 30901-30913, doi:10.1074/jbc.M203563200 [pii] (2002)).

b. The expression of T and GLIS1 in PrS differentiated from human ESC/iPSC. We used the results of G3PDH expression for normalization and adjusted ESC to 1.

c. Phase contrast images of undifferentiated human ESC/iPSC and PrS.

d. The expression of reprogramming-related genes in GLIS1-transgenic ESC. ESC introduced with empty vector (Mock), GLIS1 or NANOG were maintained in mTeSR1 medium on Matrigel-coated plates. The expression of reprogramming-related genes was quantified by qRT-PCR. We used the results of G3PDH expression for normalization and adjusted Mock to 1.

e. The expression of mesendodermal genes in GLIS1-transgenic ESC. The expression of PrS and mesoderm-related genes in the cells shown in FIG. 3d were quantified by qRT-PCR. We used the results of G3PDH expression for normalization and adjusted Mock to 1.

f. The scatter plots of microarray gene expression data. Colored dots indicate highly (red) or lowly (blue) expressed genes in indicated cell types.

g. GLIS1 induces biased differentiation potentials of ESC. The relative cell number of differentiated ESC into indicated lineages introduced with empty vector (Mock), GLIS1 or NANOG. N=3.

FIG. 6 shows that FOXH1 facilitates reprogramming efficiency.

a. FOXH1 is essential for PrS differentiation of ESC/iPSC. We performed PrS differentiation of ESC/iPSC transfected with non-targeted siRNA (nc) or FOXH1 siRNA (F), and then quantified the expression of pluripotent stem cell markers and PrS markers by qRT-PCR. We used the results of G3PDH expression for normalization and adjusted PrS derived from non-transfected ESC (−) to 1.

b. FOXH1 facilitates-iPSC generation. We introduced each PrS-related genes along with OSKM into HDF. On day 24 post-transduction, the number of iPSC colonies was counted. N=3. Error bars indicate standard deviation. Asterisks indicate P<0.05 compared to Mock.

c. The action of FOXH1 is independent from that of p53. We introduced OSKM along with various combinations of p53 shRNA, FOXH1 and GLIS1 as indicated by + and − into HDF. The relative number of iPSC colonies on day 24 post-transduction is shown. N=3. Error bars indicate standard deviation. Asterisks indicate P<0.05.

d. The expression of endogenous FOXH1 in TRA-1-60 (+) cells. Shown are the relative expression of endogenous FOXH1 (vs. iPSC (left) or HDF (right)) evaluated by qRT-PCR. N=3. Error bars indicate standard deviation.

e. FOXH1 affects the reprogramming efficiency in the late stage. We introduced OSKM alone (Mock), or along with FOXH1 into HDF. Then, we added 100 nM of Dex into the medium from the timing indicated by open circles to those by closed circles. Shown are relative numbers of iPSC colonies on day 24 post-transduction compared to OSKM alone. N=3. Error bars indicate standard deviation. Asterisks indicate P<0.05.

f. GLIS1 affects the reprogramming efficiency in the early stage. We introduced OSKM alone, or along with GLIS1 into HDF. Then, we added 100 nM of Dex into the medium from the timing indicated by open circles to those by closed circles. Shown are relative numbers of iPSC colonies on day 24 post-transduction compared to OSKM alone. N=3. Error bars indicate standard deviation. Asterisks indicate P<0.05.

g. FOXH1 increases the proportion of TRA-1-60 (+) cells in the late stage. Shown are the relative proportion of TRA-1-60 (+) cells induced by OSKM along with GLIS1 (closed bars) or FOXH1 (opened bars) on day 7, 11 and 15 post-transduction compared to those of OSKM alone at each time point. N=3. Error bars indicate standard deviation.

h. FOHX1 does not increase the proportion of TRA-1-60 (+) cells at day 7. We introduced OSKM along with FOXH1, p53 shRNA or GLIS1. The relative cell number of TRA-1-60 (+) cells at day 7 post transduction was shown. Mock=1. N=3. Asterisks indicate p<0.05.

i. FOXH1 promotes the epithelialization of TRA-1-60 (+) cells. The proportion of CD13 (+) or EpCAM (+) cells in TRA-1-60 (+) cells carrying OSKM with (opened bars) or without (closed bars) FOXH1 were analyzed by flow cytometry on day 7, 11 and 15 post-transduction. N=3. Error bars indicate standard deviation. Asterisks indicate P<0.05.

j. FOXH1 enhances the expression of late reprogramming markers. Shown are the relative expression of indicated genes in TRA-1-60 (+) cells induced by OSKMF on day 7, 11 and 15 compared to those of OSKM. N=3. Error bars indicate standard deviation.

k. FOXH1 is required normal PrS-differentiation from ESC/iPSC. We performed PrS-differentiation of ESC/iPSC transfected with negative control (nc) or FOXH1 siRNA. The marker gene expression evaluated by qPCR was normalized by G3PDH expression of each sample. Shown are the relative expression compared to PrS derived from non-transfected ESC/iPSC. N=3. Error bars indicate standard deviation.

l. Endogenous FOXH1 is required for iPSC generation. We as first introduced OSKM along with shRNA expression vector encoding scramble shRNA (Scr) or three different sequences of shRNAs against human FOXH1 gene (FOXH1 shRNA 1, 3 and 6) into human ESC. Next day, the knockdown efficiencies in transduced ESCs were evaluated by qRT-PCR (closed bars). Next, we introduced pMKO.1-puro encoding scramble shRNA (Scr), FOXH1 shRNA1, 3 or 6 with OSKM into HDF. Shown are the relative numbers of iPSC colonies on day 24 compared to Mock (opened bars). N=3. Error bars indicate standard deviation. Asterisks indicate $P<0.05$.

m. Endogenous FOXH1 does not affect HDF proliferation. Shown are relative cell numbers of HDF transduced with OSKM along with pMKO.1-puro encoding scramble shRNA (Scr), FOXH1 shRNA1, 3 or 6. N=3. Error bars indicate standard deviation.

FIG. 7 shows characterization of OSKMF-iPSC lines.

a. Phase contrast images of OSKMF-iPSC (1082A1) on SNL feeders at passage number 5. Bar indicates 100 μm.

b. The expression analyses of OCT3/4, SOX2 and NANOG in OSKMF-iPSC, H1 (ESC), 201B7 (OSKM-iPSC) and HDF. We used the results of G3PDH expression for normalization and adjusted ES cells to 1.

c. DNA methylation statuses of OCT3/4 promoter (CR1, CR2, 5' UTR) and NANOG promoter (CR1). White and black indicate the percentage of unmethylated and methylated CpG, respectively.

d. Karyotype analysis of OSKMF-iPSC.

e. The expression of surface markers such as SSEA-4, TRA-1-60 and TRA-2-49/6E in OSKMF-iPSC. Ten thousand of stained cells (closed histograms) were analyzed by flow cytometry. Open histogram indicates unstained control.

f. In vitro differentiation potentials of OSKMF-iPSC. OSKMF-iPSC were spontaneously differentiated by embryoid body-mediated protocol. A upper-left panel shows phase contrast of floating-cultured cells at day 8. After 16-days differentiation, the cells were stained with indicated antibodies (green or red) and Hoechst 33342 (blue). Bar indicates 100 μm.

g. In vivo differentiation potentials of OSKMF-iPSC. Sections of teratoma derived from OSKMF-iPSC were stained with hematoxylin and eosin.

Figure 8:
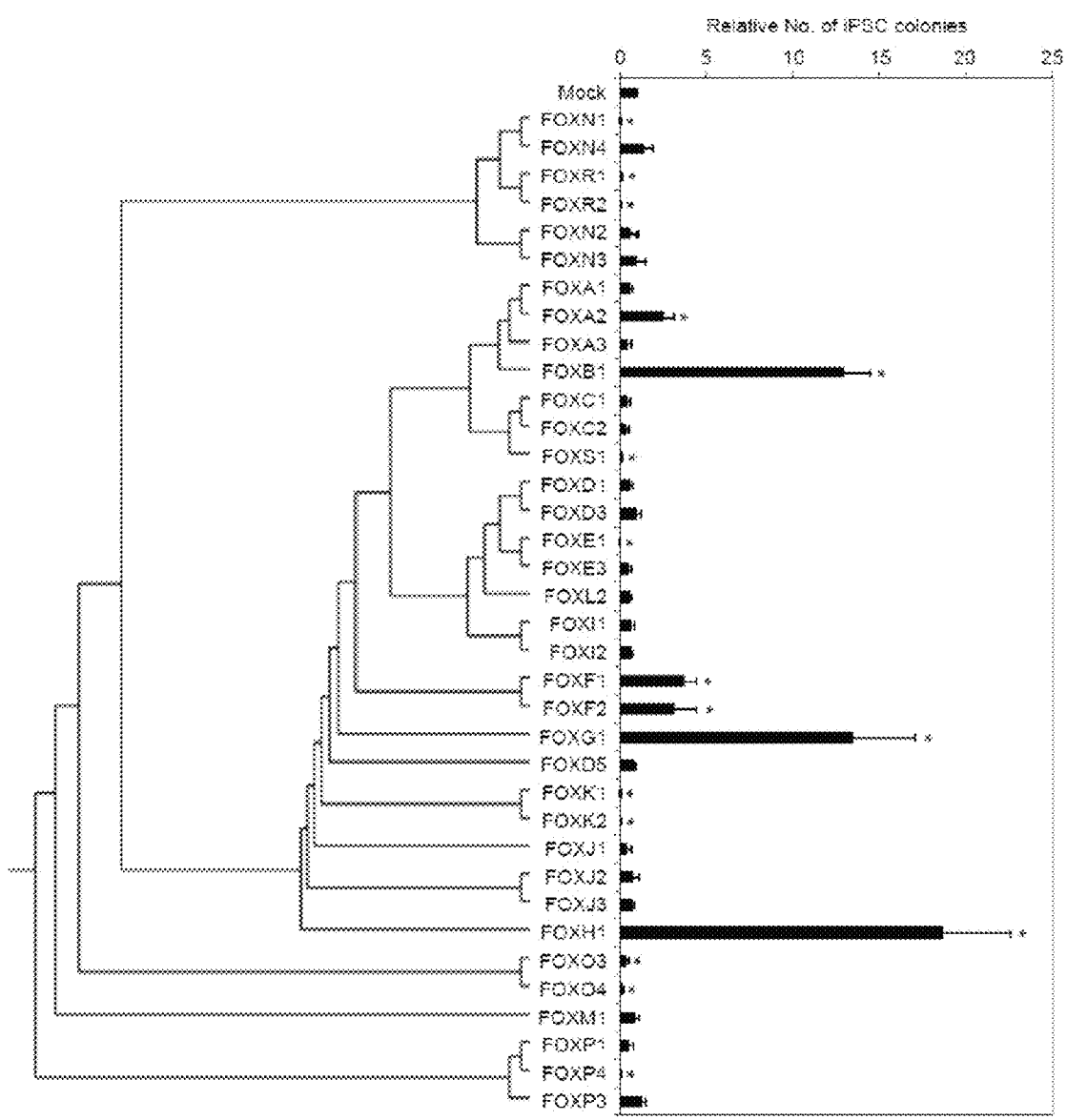

FIG. 8 shows the effects of FOX family genes on reprogramming. We introduced OSKM along with each FOX family gene as indicated into HDF by retroviral transduction. The numbers of iPSC colonies were counted on day 24 post-transduction. N=3. Error bars indicate standard deviation. Asterisks indicate $P<0.05$ compared to Mock. Left part of the figure shows the result of multiple protein sequence alignment as rooted phylogenetic tree.

Figure 9:
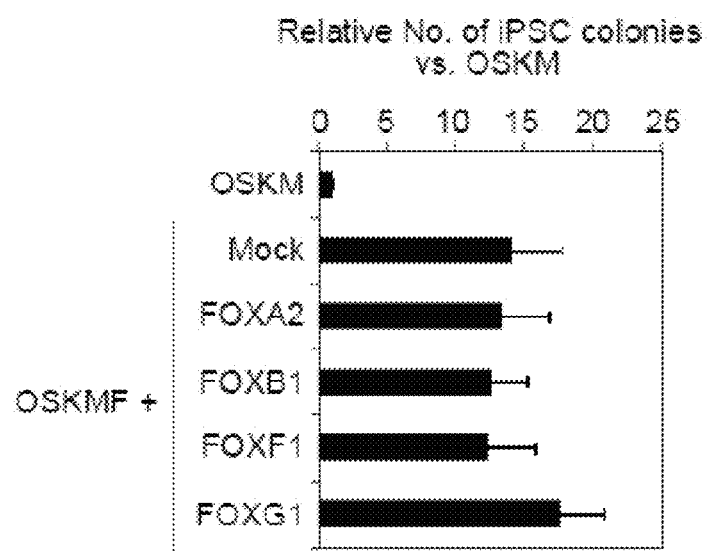

FIG. 9 shows the overlapping effects of FOX genes on reprogramming. We introduced OSKM or OSKMF along with Mock, FOXA2, FOXB1, FOXF1, FOXG1 into HDF by retroviral transduction. Shown are the numbers of iPSC colonies from $1\times10^5$ transduced HDF on day 24. N=3. Error bars indicate standard deviation.

DETAILED DESCRIPTION OF THE INVENTION

The present invention provides a method of improving the efficiency of iPS cell establishment by bringing a protein involved in PrS formation or a nucleic acid that encodes the same (hereinafter also referred to as the establishment efficiency improving factor of the present invention) into contact with a somatic cell in the step of nuclear reprogramming of the somatic cell. Here, the nuclear reprogramming of the somatic cell is achieved by transferring nuclear reprogramming substance(s) to the somatic cell; therefore, the present invention also provides a method of producing an iPS cell by bringing the establishment efficiency improving factor and nuclear reprogramming substance(s) into contact with a somatic cell. Herein, cases where iPS cells cannot be established by merely transferring nuclear reprogramming substance(s) alone to a somatic cell, but can be established by bringing nuclear reprogramming substance(s) along with the establishment efficiency improving factor of the present invention into contact with a somatic cell, are also deemed as corresponding to "an improvement of establishment efficiency."

(a) Source of Somatic Cells

In the present invention, any cells other than germ cells of mammalian origin (e.g., humans, mice, monkeys, pigs, rats etc.) can be used as starting material for the production of iPS cells. Examples include keratinizing epithelial cells (e.g., keratinized epidermal cells), mucosal epithelial cells (e.g., epithelial cells of the superficial layer of tongue), exocrine gland epithelial cells (e.g., mammary gland cells), hormone-secreting cells (e.g., adrenomedullary cells), cells for metabolism or storage (e.g., liver cells), intimal epithelial cells constituting interfaces (e.g., type I alveolar cells), intimal epithelial cells of the obturator canal (e.g., vascular endothelial cells), cells having cilia with transporting capability (e.g., airway epithelial cells), cells for extracellular matrix secretion (e.g., fibroblasts), contractile cells (e.g., smooth muscle cells), cells of the blood and the immune system (e.g., T lymphocytes), sense-related cells (e.g., rod cells), autonomic nervous system neurons (e.g., cholinergic neurons), sustentacular cells of sensory organs and peripheral neurons (e.g., satellite cells), nerve cells and glia cells of the central nervous system (e.g., astroglia cells), pigment cells (e.g., retinal pigment epithelial cells), progenitor cells thereof (tissue progenitor cells) and the like. There is no limitation on the degree of cell differentiation, the age of the animal from which cells are collected and the like; even undifferentiated progenitor cells (including somatic stem cells) and finally differentiated mature cells can be used alike as sources of somatic cells in the present invention. Examples of undifferentiated progenitor cells include tissue stem cells (somatic stem cells) such as neural stem cells, hematopoietic stem cells, mesenchymal stem cells, and dental pulp stem cells.

The choice of mammal individual as a source of somatic cells is not particularly limited; however, when the iPS cells obtained are to be used for the regenerative medicine in humans, it is preferable, from the viewpoint of prevention of graft rejection to collect the somatic cells from the patient or another person with the same or substantially the same HLA type as that of the patient. "Substantially the same HLA type" as used herein means that the HLA type of donor matches with that of patient to the extent that the transplanted cells, which have been obtained by inducing differentiation of iPS cells derived from the donor's somatic cells, can be engrafted when they are transplanted to the patient with use of immunosuppressant and the like. For example, it includes an HLA type wherein major HLAs (e.g., the three major loci of HLA-A, HLA-B and HLA-DR) are identical and the like (hereinafter the same meaning shall apply). When the iPS cells obtained are not to be administered (transplanted) to a human, but used as, for example, a source of cells for screening for evaluating a patient's drug susceptibility or adverse reactions, it is likewise desirable to collect the somatic cells from the patient or another person with the same genetic polymorphism correlating with the drug susceptibility or adverse reactions.

Before being subjected to the step of nuclear reprogramming, somatic cells separated from a mammal can be pre-cultured using a medium known per se suitable for the cultivation thereof, depending on the kind of the cells. Examples of such media include, but are not limited to, a minimal essential medium (MEM) containing about 5 to 20% fetal calf serum, Dulbecco's modified Eagle medium (DMEM), RPMI1640 medium, 199 medium, F12 medium and the like. When using, for example, a transfection reagent such as a cationic liposome in contacting the cell with the establishment efficiency improving factors of the present invention and nuclear reprogramming substance(s) (and another iPS cell establishment efficiency improver as required), it is sometimes preferable that the medium be previously replaced with a serum-free medium to prevent a reduction in the transfer efficiency.

(b) The Establishment Efficiency Improving Factor of the Present Invention

The establishment efficiency improving factor of the present invention is a protein involved in PrS formation, or a nucleic acid that encodes the same. The proteins involved in PrS formation include, but are not limited to, Foxh1, brachyury (T), goosecoid (GSC), Foxa2, eomesodermin (EOMES), LHX1, Sox17, MIXL1, GDF3, Lefty2, Nodal, Hand1, Wnt3, noggin (NOG), CER1, Foxf1, GATA4, GATA6, HESX1, HNF1A, HNF4A, OTX2, RNF111, Sox7, SP5 and TBX6. Preferably, the protein involved in PrS formation is Foxh1, brachyury (T), Foxa2, LHX1 or Foxf1, more preferably Foxh1.

Alternatively, each of the above factors may be substituted by any of other members of a family to which it belongs. For example, Foxh1 or Foxa2 may be substituted by other Fox family members including, but are not limited to, Foxa1, Foxa3, Foxb1, Foxc1, Foxc2, Foxd1, Foxd3, Foxd5, Foxe3, Foxf1, Foxf2, Foxg1, Foxi1, Foxi2, Foxj1, Foxj2, Foxj3, Foxk1, Foxk2, Foxl2, Foxm1, Foxn1, Foxan2, Foxn3, Foxn4, Foxo3, Foxo4, Foxp1, Foxp3, Foxp4, Foxr1, Foxr2 and Foxs1. Preferably, the Fox family member used as the establishment efficiency improving factor of the present invention is Foxh1, Foxa2, Foxb1, Foxf1, Foxf2 or Foxg1, more preferably Foxh1.

Although the establishment efficiency improving factor of the present invention may be proteins derived from optionally chosen mammals (e.g., humans, mice, rats, monkeys, bovines, horses, pigs, dogs and the like) or nucleic acids that encode the same, proteins or nucleic acids of human or mouse origin are preferred. Information on the amino acid sequences and cDNA sequences of Foxh1, brachyury (T), goosecoid (GSC), Foxa2, eomesodermin (EOMES), LHX1, Sox17, MIXL1, GDF3, Lefty2, Nodal, Hand1, Wnt3, noggin (NOG), CER1, Foxf1, GATA4, GATA6, HESX1, HNF1A, HNF4A, OTX2, RNF111, Sox7, SP5 and TBX6 of human or mouse origin can be acquired by referring to the NCBI accession numbers shown in Table 1; and information on the amino acid sequences and cDNA sequences of Foxa1, Foxa2, Foxa3, Foxb1, Foxa1, Foxc2, Foxd1, Foxd3, Foxd5, Foxe3, Foxf1, Foxf2, Foxg1, Foxi1, Foxi1, Foxi2, Foxj1, Foxj2, Foxj3, Foxk1, Foxk2, Foxl2, Foxm1, Foxn1, Foxan2, Foxn3, Foxn4, Foxo3, Foxo4, Foxp1, Foxp3, Foxp4, Foxr1, Foxr2 and Foxs1 of human or mouse origin can be acquired by referring to the NCBI accession numbers shown in Table 2. Those skilled in the art are easily able to isolate nucleic acids that encode the respective proteins on the basis of the cDNA sequence information, and to produce recombinant proteins as required.

TABLE 1

| Protein name (Gene name) | Human | | Mouse | |
| --- | --- | --- | --- | --- |
| | cDNA | Protein | cDNA | Protein |
| Foxh1 | NM_003923 | NP_003914 | NM_007989 | NP_032015 |
| brachyury (T) | NM_003181 | NP_003172 | NM_009309 | NP_033335 |
| goosecoid (GSC) | NM_173849 | NP_776248 | NM_010351 | NP_034481 |
| Foxa2 | NM_021784 | NP_068556 | NM_010446 | NP_034576 |
| eomesodermin (EOMES) | NM_005442 | NP_005433 | NM_010136 | NP_034266 |
| LHX1 | NM_005568 | NP_005559 | NM_008498 | NP_032524 |
| Sox17 | NM_022454 | NP_071899 | NM_011441 | NP_035571 |
| MIXL1 | NM_031944 | NP_114150 | NM_013729 | NP_038757 |
| GDF3 | NM_020634 | NP_065685 | NM_008108 | NP_032134 |
| Lefty2 | NM_003240 | NP_003231 | NM_177099 | NP_796073 |
| Nodal | NM_018055 | NP_060525 | NM_013611 | NP_038639 |
| Hand1 | NM_004821 | NP_004812 | NM_008213 | NP_032239 |
| Wnt3 | NM_030753 | NP_110380 | NM_009521 | NP_033547 |
| noggin (NOG) | NM_005450 | NP_005441 | NM_008711 | NP_032737 |
| CER1 | NM_005454 | NP_005445 | NM_009887 | NP_034017 |
| Foxf1 | NM_001451 | NP_001442 | NM_010426 | NP_034556 |
| GATA4 | NM_002052 | NP_002043 | NM_008092 | NP_032118 |
| GATA6 | NM_005257 | NP_005248 | NM_010258 | NP_034388 |
| GSC | NM_173849 | NP_776248 | NM_010351 | NP_034481 |
| HESX1 | NM_003865 | NP_003856 | NM_010420 | NP_034550 |
| HNF1A | NM_000545 | NP_000536 | NM_009327 | NP_033353 |
| HNF4A | NM_178849 | NP_000448 | NM_008261 | NP_032287 |
| OTX2 | NM_021728 | NP_068374 | NM_144841 | NP_659090 |
| RNF111 | NM_001270528 | NP_060080 | NM_033604 | NP_291082 |
| Sox7 | NM_031439 | NP_113627 | NM_011446 | NP_035576 |

TABLE 1-continued

| Protein name | Human | | Mouse | |
|---|---|---|---|---|
| (Gene name) | cDNA | Protein | cDNA | Protein |
| SP5 | NM_001003845 | NP_001003845 | NM_022435 | NP_071880 |
| TBX6 | NM_004608 | NP_004599 | NM_011538 | NP_035668 |

TABLE 2

| Protein name | Human | | Mouse | |
|---|---|---|---|---|
| (Gene name) | cDNA | Protein | cDNA | Protein |
| Foxa1 | NM_004496 | NP_004487 | NM_008259 | NP_032285 |
| Foxa2 | NM_021784 | NP_068556 | NM_010446 | NP_034576 |
| Foxa3 | NM_004497 | NP_004488 | NM_008260 | NP_032286 |
| Foxb1 | NM_012182 | NP_036314 | NM_022378 | NP_071773 |
| Foxc1 | NM_001453 | NP_001444 | NM_008592 | NP_032618 |
| Foxc2 | NM_005251 | NP_005242 | NM_013519 | NP_038547 |
| Foxd1 | NM_205192 | NP_004463 | NM_008242 | NP_004463 |
| Foxd3 | NM_012183 | NP_036315 | NM_010425 | NP_034555 |
| Foxd5 | NM_012184 | NP_036316 | NM_008022 | NP_032048 |
| Foxe3 | NM_012186 | NP_036318 | NM_015758 | NP_056573 |
| Foxf1 | NM_001451 | NP_001442 | NM_010426 | NP_034556 |
| Foxf2 | NM_001452 | NP_001443 | NM_010225 | NP_034355 |
| Foxg1 | NM_005249 | NP_005240 | NM_008241 | NP_001153584 |
| Foxh1 | NM_003923 | NP_003914 | NM_007989 | NP_032015 |
| Foxi1 | NM_012188 | NP_036320 | NM_023907 | NP_076396 |
| Foxi2 | NM_207426 | NP_997309 | NM_183193 | NP_899016 |
| Foxj1 | NM_001454 | NP_001445 | NM_008240 | NP_032266 |
| Foxj2 | NM_018416 | NP_060886 | NM_021899 | NP_068699 |
| Foxj3 | NM_014947 | NP_001185781 | NM_172699 | NP_766287 |
| Foxk1 | NM_001037165 | NP_001032242 | NM_199068 | NP_951031 |
| Foxk2 | NM_004514 | NP_004505 | NM_001080932 | NP_001074401 |
| Foxl2 | NM_023067 | NP_075555 | NM_012020 | NP_036150 |
| Foxm1 | NM_202002 | NP_973732 | NM_008021 | NP_032047 |
| Foxn1 | NM_003593 | NP_003584 | NM_008238 | NP_032264 |
| Foxn2 | NM_002158 | NP_002149 | NM_180974 | NP_851305 |
| Foxn3 | NM_001085471 | NP_001078940 | NM_183186 | NP_899009 |
| Foxn4 | NM_213596 | NP_998761 | NM_148935 | NP_683737 |
| Foxo3 | NM_001455 | NP_001446 | NM_019740 | NP_062714 |
| Foxo4 | NM_005938 | NP_005929 | NM_018789 | NP_061259 |
| Foxp1 | NM_032682 | NP_116071 | NM_053202 | NP_444432 |
| Foxp3 | NM_014009 | NP_054728 | NM_001199347 | NP_001186276 |
| Foxp4 | NM_001012426 | NP_001012426 | NM_001110824 | NP_001104294 |
| Foxr1 | NM_181721 | NP_859072 | NM_001033469 | NP_001028641 |
| Foxr2 | NM_198451 | NP_940853 | NM_001034894 | NP_001030066 |
| Foxs1 | NM_004118 | NP_004109 | NM_010226 | NP_034356 |

A natural or artificial mutant protein having an identity of 80% or more, preferably 90% or more, more preferably 95% or more, particularly preferably 97% or more, to each amino acid sequence shown above, and possessing a potential for improving iPS cell establishment efficiency equivalent to or greater than that of the wild-type protein and a nucleic acid that encodes the same, can also be utilized as the establishment efficiency improving factors of the present invention.

Out of the proteins involved in PrS formation (including nucleic acids that encode the same), any one kind alone may be used, and two kinds or more may be used in combination.

The establishment efficiency improving factor of the present invention may also be used as "a nuclear reprogramming substance" as stated below, in combination with any other nuclear reprogramming substance(s) in producing an iPS cell.

Transfer of the protein involved in PrS formation to a somatic cell can be achieved using a method known per se for protein transfer into a cell, provided that the substance is a proteinous factor. Such methods include, for example, the method using a protein transfer reagent, the method using a protein transfer domain (PTD)- or cell penetrating peptide (CPP)-fusion protein, the microinjection method and the like. Protein transfer reagents are commercially available, including those based on a cationic lipid, such as BioPOTER Protein Delivery Reagent (Gene Therapy Systems), Pro-Ject™ Protein Transfection Reagent (PIERCE) and ProVectin (IMGENEX); those based on a lipid, such as Profect-1 (Targeting Systems); those based on a membrane-permeable peptide, such as Penetrain Peptide (Q biogene) and Chariot Kit (Active Motif), GenomONE (ISHIHARA SANGYO KAISHA, LTD.) utilizing HVJ envelope (inactivated hemagglutinating virus of Japan) and the like. The transfer can be achieved per the protocols attached to these reagents, a common procedure being as described below. The protein involved in PrS formation is diluted in an appropriate solvent (e.g., a buffer solution such as PBS or HEPES), a transfer reagent is added, the mixture is incubated at room temperature for about 5 to 15 minutes to form a complex, this complex is added to cells after exchanging the medium with a serum-free medium, and the cells are incubated at 37° C. for one to several hours. Thereafter, the medium is removed and replaced with a serum-containing medium.

Alternatively, a reverse transfection may be used, wherein the protein is immobilized onto a solid phase such as a well plate, culture dish and the like followed by the addition of somatic cells to the solid phase.

Developed PTDs include those using transcellular domains of proteins such as drosophila-derived AntP, HIV-derived TAT (Frankel, A. et al, *Cell* 55, 1189-93 (1988) or Green, M. & Loewenstein, P. M. *Cell* 55, 1179-88 (1988)), Penetratin (Derossi, D. et al, *J. Biol. Chem.* 269, 10444-50 (1994)), Buforin II (Park, C. B. et al. *Proc. Natl Acad. Sci. USA* 97, 8245-50 (2000)), Transportan (Pooga, M. et al. *FASEB J.* 12, 67-77 (1998)), MAP (model amphipathic peptide) (Oehlke, J. et al. *Biochim. Biophys. Acta.* 1414, 127-39 (1998)), K-FGF (Lin, Y. Z. et al. *J. Biol. Chem.* 270, 14255-14258 (1995)), Ku70 (Sawada, M. et al. *Nature Cell Biol.* 5, 352-7 (2003)), Prion (Lundberg, P. et al. *Biochem. Biophys. Res. Commun.* 299, 85-90 (2002)), pVEC (Elmquist, A. et al. *Exp. Cell Res.* 269, 237-44 (2001)), Pep-1 (Morris, M. C. et al. *Nature Biotechnol.* 19, 1173-6 (2001)), Pep-7 (Gao, C. et al. *Bioorg. Med. Chem.* 10, 4057-65 (2002)), SynB1 (Rousselle, C. et al. *Mol. Pharmacol.* 57, 679-86 (2000)), HN-I (Hong, F. D. & Clayman, G L. *Cancer Res.* 60, 6551-6 (2000)), and HSV-derived VP22. CPPs derived from the PTDs include polyarginines such as 11R (*Cell Stem Cell,* 4, 381-384 (2009)) and 9R (*Cell Stem Cell,* 4, 472-476 (2009)).

A fusion protein expression vector incorporating a cDNA encoding the protein involved in PrS formation and a PTD or CPP sequence is prepared to allow the recombinant expression of the fusion protein, and the fusion protein is recovered for use for transfer. This transfer can be achieved as described above, except that no protein transfer reagent is added.

Microinjection, a method of placing a protein solution in a glass needle having a tip diameter of about 1 μm, and injecting the solution into a cell, ensures the transfer of the protein into the cell.

Other useful methods of protein transfer include electroporation, the semi-intact cell method [Kano, F. et al. Methods in Molecular Biology, Vol. 322, 357-365(2006)], transfer using the Wr-t peptide [Kondo, E. et al., Mol. Cancer Ther. 3(12), 1623-1630(2004)] and the like.

The protein transferring operation can be performed one or more optionally chosen times (e.g., once or more to 10 times or less, or once or more to 5 times or less and the like). Preferably, the transferring operation can be performed twice or more (e.g., 3 times or 4 times) repeatedly. The time interval for repeated transferring operation is, for example, 6 to 48 hours, preferably 12 to 24 hours.

The choice of a nucleic acid that encodes a protein involved in PrS formation is not particularly limited. The nucleic acid may be a DNA or an RNA, or a DNA/RNA chimera, and is preferably a DNA. The nucleic acid may be double-stranded or single-stranded. In the case of double strands, the nucleic acid may be a double-stranded DNA, a double-stranded RNA or a DNA:RNA hybrid.

A nucleic acid encoding a protein involved in PrS formation can, for example, be cloned from a cell or tissue [e.g., cells and tissues of thymus, bone marrow, spleen, brain, spinal cord, heart, skeletal muscle, kidney, lung, liver, pancreas or prostate, progenitor cells, stem cells or cancer cells of these cells, and the like] of a human or another mammal (e.g., mouse, rat, monkey, pig, dog and the like) by a conventional method.

Transfer of a nucleic acid encoding a protein involved in PrS formation to a somatic cell can be achieved using a method of gene transfer to cells known per se. A nucleic acid that encodes a protein involved in PrS formation is inserted into an appropriate expression vector containing a promoter capable of functioning in the host somatic cell. Useful expression vectors include, for example, viral vectors such as retrovirus, lentivirus, adenovirus, adeno-associated virus, herpes virus and Sendai virus, plasmids for the expression in animal cells (e.g., pA1-11, pXT1, pRc/CMV, pRc/RSV, pcDNAI/Neo) and the like.

A vector for this purpose can be chosen as appropriate according to the intended use of the iPS cell to be obtained. Useful vectors include adenovirus vector, plasmid vector, adeno-associated virus vector, retrovirus vector, lentivirus vector, Sendai virus vector, episomal vector and the like.

Examples of promoters used in expression vectors include the EF1α promoter, the CAG promoter, the SRα promoter, the SV40 promoter, the LTR promoter, the CMV (cytomegalovirus) promoter, the RSV (Rous sarcoma virus) promoter, the MoMuLV (Moloney mouse leukemia virus) LTR, the HSV-TK (herpes simplex virus thymidine kinase) promoter and the like, with preference given to the EF1α promoter, the CAG promoter, the MoMuLV LTR, the CMV promoter, the SRα promoter and the like.

The expression vector may contain as desired, in addition to a promoter, an enhancer, a polyadenylation signal, a selectable marker gene, a SV40 replication origin and the like. Examples of selectable marker genes include the dihydrofolate reductase gene, the neomycin resistant gene, the puromycin resistant gene and the like.

A nucleic acid that encodes a protein involved in PrS formation may be integrated alone into an expression vector, or along with one or more reprogramming genes into an expression vector. Preference is sometimes given to the former case when using a retrovirus or lentivirus vector, which offer high gene transfer efficiency, and to the latter case when using a plasmid, adenovirus, or episomal vector and the like, but there are no particular limitations.

In the context above, when a nucleic acid that encodes a protein involved in PrS formation and one or more reprogramming genes are integrated in one expression vector, these genes can preferably be integrated into the expression vector via a sequence enabling polycistronic expression. By using a sequence enabling polycistronic expression, it is possible to more efficiently express a plurality of genes integrated in one expression vector. Useful sequences enabling polycistronic expression include, for example, the 2A sequence of foot-and-mouth disease virus (*PLoS ONE* 3, e2532, 2008, Stem Cells 25, 1707, 2007), the IRES sequence (U.S. Pat. No. 4,937,190) and the like, with preference given to the 2A sequence.

An expression vector harboring a nucleic acid that encodes a protein involved in PrS formation can be introduced into a cell by a technique known per se according to the choice of the vector. In the case of a viral vector, for example, a plasmid containing the nucleic acid is introduced into an appropriate packaging cell (e.g., Plat-E cells) or a complementary cell line (e.g., 293-cells), the viral vector produced in the culture supernatant is recovered, and the vector is infected to the cell by a method suitable for each viral vector. For example, specific means using a retroviral vector are disclosed in WO2007/69666, *Cell,* 126, 663-676 (2006) and *Cell,* 131, 861-872 (2007); when a lentivirus vector is used, a disclosure is available in *Science,* 318, 1917-1920 (2007). When iPS cells are utilized as a source of cells for regenerative medicine, the expression (reactivation) of a protein involved in PrS formation or the activation of an endogenous gene present in the vicinity of the site where the exogenous gene is integrated potentially increases the risk of carcinogenesis in tissues regenerated from differentiated cells of iPS cell derivation; therefore, a nucleic acid that encodes a protein involved in PrS formation is preferably expressed transiently, without being integrated into the chromosome of the cells. From this viewpoint, use of an adenoviral vector, whose integration into chromosome is rare, is preferred. Specific means using an adenoviral vector is described in *Science*, 322, 945-949 (2008). Because an adeno-associated viral vector is also low in the frequency of integration into chromosome, and is lower than adenoviral vectors in terms of cytotoxicity and inflammation-inducibility, it can be mentioned as another preferred vector. Because Sendai viral vector is capable of being stably present outside the chromosome, and can be degraded and removed using an siRNA as required, it is preferably utilized as well. Regarding a Sendai viral vector, one described in *J. Biol. Chem.*, 282, 27383-27391 (2007) and JP-3602058 B can be used.

When a retroviral vector or a lentiviral vector is used, even if silencing of the transgene has occurred, it possibly becomes reactivated later; therefore, for example, a method can be used preferably wherein a nucleic acid that encodes a protein involved in PrS formation is cut out using the Cre/loxP system, when becoming unnecessary. That is, with loxP sequences arranged on both ends of the nucleic acid in advance, after iPS cells are induced, the Cre recombinase is allowed to act on the cells using a plasmid vector or adenoviral vector, and the region sandwiched by the loxP sequences can be cut out. Because the enhancer-promoter sequence of the LTR U3 region possibly upregulates a host gene in the vicinity thereof by insertion mutation, it is more preferable to avoid the expression regulation of the endogenous gene by the LTR outside of the loxP sequence remaining in the genome without being cut out, using a 3'-self-inactivating (SIN) LTR prepared by deleting the sequence, or substituting the sequence with a polyadenylation sequence such as of SV40. Specific means using the Cre-loxP system and SIN LTR is disclosed in Soldner et al., *Cell*, 136: 964-977 (2009), Chang et al., *Stem Cells*, 27: 1042-1049 (2009) and the like.

Meanwhile, being a non-viral vector, a plasmid vector can be transferred into a cell using the lipofection method, liposome method, electroporation method, calcium phosphate co-precipitation method, DEAE dextran method, microinjection method, gene gun method and the like. Specific means using a plasmid as a vector are described in, for example, *Science*, 322, 949-953 (2008) and the like.

When a plasmid vector, an adenovirus vector and the like are used, the transfection can be performed once or more optionally chosen times (e.g., once to 10 times, once to 5 times or the like). When two or more kinds of expression vectors are introduced into a somatic cell, it is preferable that these all kinds of expression vectors be concurrently introduced into a somatic cell; however, even in this case, the transfection can be performed once or more optionally chosen times (e.g., once to 10 times, once to 5 times or the like), preferably the transfection can be repeatedly performed twice or more (e.g., 3 times or 4 times).

Also when an adenovirus or a plasmid is used, the transgene can get integrated into chromosome; therefore, it is eventually necessary to confirm the absence of insertion of the gene into chromosome by Southern blotting or PCR. For this reason, like the aforementioned Cre-loxP system, it can be advantageous to use a means wherein the transgene is integrated into chromosome, thereafter the gene is removed. In another preferred mode of embodiment, a method can be used wherein the transgene is integrated into chromosome using a transposon, thereafter a transposase is allowed to act on the cell using a plasmid vector or adenoviral vector so as to completely eliminate the transgene from the chromosome.

As examples of preferable transposons, piggyBac, a transposon derived from a lepidopterous insect, and the like can be mentioned. Specific means using the piggyBac transposon is disclosed in Kaji, K. et al., *Nature*, 458: 771-775 (2009), Woltjen et al., *Nature*, 458: 766-770 (2009).

Another preferable non-integration type vector is an episomal vector, which is autonomously replicable outside the chromosome. Specific means with the use of an episomal vector is described by Yu et al. in *Science*, 324, 797-801 (2009). As appropriate, an expression vector in which a nucleic acid that encodes a protein involved in PrS formation is inserted into an episomal vector having loxP sequences placed in the same orientation on the 5' and 3' sides of the vector constituent essential for the replication of the episomal vector can be constructed and introduced into a somatic cell.

Examples of the episomal vector include a vector comprising, as a vector component, a sequence derived from EBV, SV40 and the like necessary for self-replication. The vector component necessary for self-replication is specifically exemplified by a replication origin and a gene that encodes a protein that binds to the replication origin to control the replication; examples include the replication origin oriP and the EBNA-1 gene for EBV, and the replication origin on and the SV40 large T antigen gene for SV40.

The episomal expression vector harbors a promoter that controls the transcription of a nucleic acid that encodes a protein involved in PrS formation. Useful promoters include those mentioned above. The episomal expression vector, like the aforementioned vectors, may further contain as desired an enhancer, a polyA addition signal, a selection marker gene and the like. Examples of useful selection marker genes include the dihydrofolate reductase gene, the neomycin resistance gene and the like.

The loxP sequences useful in the present invention include, in addition to the bacteriophage P1-derived wild type loxP sequence, optionally chosen mutant loxP sequences capable of deleting the sequence flanked by the loxP sequence by recombination when placed in the same orientation at positions flanking a vector component necessary for the replication of the introduced gene. Examples of such mutant loxP sequences include lox71, mutated in 5' repeat, lox66, mutated in 3' repeat, and lox2272 and lox511, mutated in spacer portion. Although the two loxP sequences placed on the 5' and 3' sides of the vector component may be identical or not, the two mutant loxP sequences mutated in spacer portion must be identical (e.g., a pair of lox2272 sequences, a pair of lox511 sequences). Preference is given to a combination of a mutant loxP sequence mutated in 5' repeat (e.g., lox71) and a mutant loxP sequence mutated in 3' repeat (e.g., lox66). In this case, the loxP sequences remaining on the chromosome have double mutations in the repeats on the 5' side and 3' side as a result of recombination, and are therefore unlikely to be recognized by Cre recombinase, thus reducing the risk of causing a deletion mutation in the chromosome due to unwanted recombination. When the mutant loxP sequences lox71 and lox66 are used in combination, each may be placed on any of the 5' and 3' sides of the aforementioned vector component, but it is necessary that the mutant loxP sequences be inserted in an orientation such that the mutated sites would be located at the outer ends of the respective loxP sequences. Although a preferred episomal vector of the present invention is a self-removal vector early shedding from the cell even without being acted on by Cre recombinase, there are possibly exceptional cases where longer time is taken for the episomal vector to be shed from the cell. It is preferable, therefore, that the loxP sequences be designed in preparation for risks such as unwanted recombination due to Cre recombinase treatment.

Each of the two loxP sequences is placed in the same orientation on the 5' and 3' sides of a vector constituent essential for the replication of the introduced gene (i.e., a replication origin, or a gene sequence that encodes a protein that binds to the replication origin to control the replication). The vector constituent flanked by the loxP sequences may be either the replication origin or a gene sequence that encodes a protein that binds to a replication origin to control the replication, or both.

The episomal vector allows the vector to be introduced into the cell using, for example, the lipofection method, liposome method, electroporation method, calcium phosphate co-precipitation method, DEAE dextran method, microinjection method, gene gun method and the like. Specifically, for example, methods described in *Science*, 324: 797-801 (2009) and elsewhere can be used.

Whether or not the vector component necessary for the replication of the introduced gene has been removed from the iPS cell can be confirmed by performing a Southern blot analysis or PCR analysis using a nucleic acid comprising a nucleotide sequence in the vector component as a probe or primer, with the episome fraction isolated from the iPS cell as a template, and determining the presence or absence of a band or the length of the band detected. The episome fraction can be prepared by a method well known in the art; for example, methods described in *Science*, 324: 797-801 (2009) and elsewhere can be used.

(c) Nuclear Reprogramming Substances

As used herein, "a nuclear reprogramming substance" can include a proteinous factor, a nucleic acid that encodes the same (including a form integrated in a vector) or a low molecular weight compound, as long as it can induce an iPS cell from a somatic cell upon its contact with the somatic cell together with the iPS cell establishment efficiency improving factors of the present invention. When the nuclear reprogramming substance is a proteinous factor or a nucleic acid that encodes the same, the following combinations, for example, are preferable (hereinafter, only the names for proteinous factors are shown).

(1) Oct3/4, Klf4, c-Myc
(2) Oct3/4, Klf4, c-Myc, Sox2 (Sox2 is replaceable with Sox1, Sox3, Sox15, Sox17 or Sox18; Klf4 is replaceable with Klf1, Klf2 or Klf5; c-Myc is replaceable with T58A (active mutant), N-Myc, or L-Myc)
(3) Oct3/4, Klf4, c-Myc, Sox2, Fbx15, Nanog, Eras, ECAT15-2, Tcl1, β-catenin (active mutant S33Y)
(4) Oct3/4, Klf4, c-Myc, Sox2, TERT, SV40 Large T antigen (hereinafter SV40LT)
(5) Oct3/4, Klf4, c-Myc, Sox2, TERT, HPV16 E6
(6) Oct3/4, Klf4, c-Myc, Sox2, TERT, HPV16 E7
(7) Oct3/4, Klf4, c-Myc, Sox2, TERT, HPV6 E6, HPV16 E7
(8) Oct3/4, Klf4, c-Myc, Sox2, TERT, Bmil [For more information on the factors shown above, see WO 2007/069666 (for information on replacement of Sox2 with Sox18 and replacement of Klf4 with Klf1 or Klf5 in the combination (2) above, see *Nature Biotechnology*, 26, 101-106 (2008)); for the combination "Oct3/4, Klf4, c-Myc, Sox2", see also *Cell*, 126, 663-676 (2006), *Cell*, 131, 861-872 (2007) and the like; for the combination "Oct3/4, Klf2 (or Klf5), c-Myc, Sox2", see also *Nat. Cell Biol.*, 11, 197-203 (2009); for the combination "Oct3/4, Klf4, c-Myc, Sox2, hTERT, SV40 LT", see also *Nature*, 451, 141-146 (2008).]

(9) Oct3/4, Klf4, Sox2 (see *Nature Biotechnology*, 26, 101-106 (2008))
(10) Oct3/4, Sox2, Nanog, Lin28 (see *Science*, 318, 1917-1920 (2007))
(11) Oct3/4, Sox2, Nanog, Lin28, hTERT, SV40LT (see *Stem Cells*, 26, 1998-2005 (2008))
(12) Oct3/4, Klf4, c-Myc, Sox2, Nanog, Lin28 (see *Cell Research* (2008) 600-603)
(13) Oct3/4, Klf4, c-Myc, Sox2, SV40LT (see also *Stem Cells*, 26, 1998-2005 (2008)).
(14) Oct3/4, Klf4 (see *Nature* 454:646-650 (2008), Cell Stem Cell, 2:525-528 (2008))
(15) Oct3/4, c-Myc (see *Nature* 454:646-650 (2008))
(16) Oct3/4, Sox2 (see *Nature*, 451, 141-146 (2008), WO2008/118820)
(17) Oct3/4, Sox2, Nanog (see WO2008/118820)
(18) Oct3/4, Sox2, Lin28 (see WO2008/118820)
(19) Oct3/4, Sox2, c-Myc, Esrrb (Here, Essrrb can be substituted by Esrrg, see *Nat. Cell Biol.*, 11, 197-203 (2009))
(20) Oct3/4, Sox2, Esrrb (see *Nat. Cell Biol.*, 11, 197-203 (2009))
(21) Oct3/4, Klf4, L-Myc (see *Proc. Natl. Acad. Sci. USA.*, 107, 14152-14157 (2010))
(22) Oct3/4, Nanog
(23) Oct3/4 (Cell 136: 411-419 (2009); *Nature*, 08436, doi:10.1038 published online (2009))
(24) Oct3/4, Klf4, c-Myc, Sox2, Nanog, Lin28, SV40LT (see *Science*, 324: 797-801 (2009))
(25) Oct3/4, Sox2, Klf4, L-Myc, Lin28, Glis1

In (1)-(25) above, Oct3/4 may be replaced with another member of the Oct family, for example, Oct1A, Oct6 or the like. Sox2 (or Sox1, Sox3, Sox15, Sox17, Sox18) may be replaced with another member of the Sox family, for example, Sox7 or the like. Furthermore, in (1) to (25) above, when c-Myc or Lin28 is included as a nuclear reprogramming factor, L-Myc or Lin28B can be used in place of c-Myc or Lin28, respectively.

Any combination that does not fall in (1) to (25) above but comprises all the constituents of any one of (1) to (25) above and further comprises an optionally chosen other substance can also be included in the scope of "nuclear reprogramming substances" in the present invention. Provided that the somatic cell to undergo nuclear reprogramming is endogenously expressing one or more of the constituents of any one of (1) to (25) above at a level sufficient to cause nuclear reprogramming, a combination of only the remaining constituents excluding the one or more constituents can also be included in the scope of "nuclear reprogramming substances" in the present invention.

Of these combinations, a combination of at least one, preferably two or more, more preferably three or more, selected from among Oct3/4, Sox2, Klf4, c-Myc or L-Myc, Nanog, Lin28 or Lin28B, Glis1 and SV40LT, is a preferable nuclear reprogramming substance.

Particularly, when the iPS cells obtained are to be used for therapeutic purposes, a combination of the three factors Oct3/4, Sox2 and Klf4 [combination (9) above] or a combination of the four factors Oct3/4, Sox2, Klf4 and L-Myc [combination (2) above] are preferably used. In addition, Lin28 or Lin28B and/or Glis1 can further be used. When the iPS cells obtained are not to be used for therapeutic purposes (e.g., used as an investigational tool for drug discovery screening and the like), in addition to the three factors consisting of Oct3/4, Sox2 and Klf4 and the four factors consisting of Oct3/4, Sox2, Klf4 and L-Myc, four factors consisting of Oct3/4, Sox2, Klf4 and c-Myc, five to seven factors consisting of Oct3/4, Sox2, Klf4 and c-Myc/L-Myc as well as Nanog and/or Lin28/Lin28b and/or Glis1, or six to eight factors consisting of the above five to seven factors and additional SV40 Large T antigen are exemplified.

Information on the mouse and human cDNA sequences of the aforementioned nuclear reprogramming substances is available with reference to the NCBI accession numbers mentioned in WO 2007/069666 (in the publication, Nanog is described as ECAT4. Mouse and human cDNA sequence information on Lin28, Lin28b, Esrrb, Esrrg, L-Myc can be acquired by referring to the following NCBI accession numbers, respectively); those skilled in the art are easily able to isolate these cDNAs.

| Name of gene | Mouse | Human |
| --- | --- | --- |
| Lin28 | NM_145833 | NM_024674 |
| Lin28b | NM_001031772 | NM_001004317 |
| Esrrb | NM_011934 | NM_004452 |
| Esrrg | NM_011935 | NM_001438 |
| L-Myc | NM_008506 | NM_001033081 |
| Glis1 | NM_147221 | NM_147193 |

A proteinous factor for use as a nuclear reprogramming substance can be prepared by inserting the cDNA obtained into an appropriate expression vector, introducing the vector into a host cell, and recovering the recombinant proteinous factor from the cultured cell or its conditioned medium. Meanwhile, when the nuclear reprogramming substance used is a nucleic acid that encodes a proteinous factor, the cDNA obtained is inserted into a viral vector, episomal vector, or plasmid vector to construct an expression vector, and the vector is subjected to the step of nuclear reprogramming. As appropriate, the above-mentioned Cre-loxP system or piggyBac transposon system can be utilized. When two or more nucleic acids encoding proteinous factors are introduced into a cell, respective nucleic acids can be carried in separate vectors. Alternatively, a polycistronic vector can be constructed by ligating a plurality of nucleic acids in tandem. In latter, it is preferable that 2A self-cleaving peptide from a foot-and-mouth disease virus (*Science,* 322, 949-953, 2008) is ligated between the nucleic acids to allow for an efficient polycistronic expression.

Contact of a nuclear reprogramming substance with a somatic cell can be achieved as with a protein involved in PrS formation (a) when the substance is a proteinous factor; as with the aforementioned nucleic acid that encodes a protein involved in PrS formation (b) when the substance is a nucleic acid that encodes the proteinous factor of (a).

(d) Other iPS Cell Establishment Efficiency Improvers

In recent years, various substances that improve the efficiency of establishment of iPS cells, which has traditionally been low, have been proposed one after another. When brought into contact with a somatic cell together with the aforementioned iPS cell establishment efficiency improving factors of the present invention, these other establishment efficiency improvers are expected to further raise the efficiency of establishment of iPS cells.

Examples of other iPS cell establishment efficiency improvers include, but are not limited to, histone deacetylase (HDAC) inhibitors [e.g., valproic acid (VPA) (*Nat. Biotechnol.*, 26(7): 795-797 (2008)], low-molecular inhibitors such as trichostatin A, sodium butyrate, MC 1293, and M344, nucleic acid-based expression inhibitors such as siRNAs and shRNAs against HDAC (e.g., HDAC1 siRNA Smartpool® (Millipore), HuSH 29mer shRNA Constructs against HDAC1 (OriGene) and the like), and the like], DNA methyltransferase inhibitors (e.g., 5'-azacytidine) [*Nat. Biotechnol.*, 26(7): 795-797 (2008)], G9a histone methyltransferase inhibitors [e.g., low-molecular inhibitors such as BIX-01294 (*Cell Stem Cell,* 2: 525-528 (2008)], nucleic acid-based expression inhibitors such as siRNAs and shRNAs against G9a [e.g., G9a siRNA (human) (Santa Cruz Biotechnology) and the like) and the like], L-channel calcium agonists (e.g., Bayk8644) [*Cell Stem Cell,* 3, 568-574 (2008)], p53 inhibitors [e.g., siRNA, shRNA, dominant negative mutant and the like against p53 (*Cell Stem Cell,* 3, 475-479 (2008); Nature 460, 1132-1135 (2009))], UTF1 [*Cell Stem Cell,* 3, 475-479 (2008)], Wnt Signaling (e.g., soluble Wnt3a) [*Cell Stem Cell,* 3, 132-135 (2008)], 2i/LIF [2i is an inhibitor of mitogen-activated protein kinase signaling and glycogen synthase kinase-3, *PloS Biology,* 6(10), 2237-2247 (2008)], ES cell-specific miRNA (for example, miR-302-367 cluster (*Mol. Cell. Biol.* doi:10.1128/MCB.00398-08), miR-302 (RNA (2008) 14: 1-10), miR-291-3p, miR-294 and miR-295 (*Nat. Biotechnol.* 27: 459-461 (2009)) and the like. As mentioned above, the nucleic acid-based expression inhibitors may be in the form of expression vectors harboring a DNA that encodes an siRNA or shRNA.

Preferably, a p53 inhibitor such as p53 shRNA, p53 siRNA or dominant negative mutant of p53, or a nucleic acid that encodes the same is used as an additional iPS cell establishment efficiency improver, since a protein involved in PrS formation and p53 inhibitor independently enhance reprogramming each other and they can exert synergetic effects in combination.

Among the constituents of the aforementioned nuclear reprogramming substances, SV40 large T and the like, for example, can also be included in the scope of iPS cell establishment efficiency improvers because they are deemed not essential, but auxiliary, factors for somatic cell nuclear reprogramming. In the situation of the mechanisms for nuclear reprogramming remaining unclear, the auxiliary factors, which are not essential for nuclear reprogramming, may be conveniently considered as nuclear reprogramming substances or iPS cell establishment efficiency improvers. Hence, because the somatic cell nuclear reprogramming process is understood as an overall event resulting from contact of nuclear reprogramming substance(s) and IPS cell establishment efficiency improver(s) with a somatic cell, it seems unnecessary for those skilled in the art to always distinguish between the nuclear reprogramming substance and the iPS cell establishment efficiency improver.

Contact of an iPS cell establishment efficiency improver with a somatic cell can be achieved as with a protein involved in PrS formation (a) when the improver is a proteinous factor; as with the aforementioned nucleic acid that encodes a protein involved in PrS formation (b) when the improver is a nucleic acid that encodes the proteinous factor of (a).

An iPS cell establishment efficiency improver including a protein involved in PrS formation or a nucleic acid encoding the same may be brought into contact with a somatic cell simultaneously with a nuclear reprogramming substance, or either one may be contacted in advance, as far as the efficiency of establishment of iPS cells from the somatic cell is significantly improved, compared with the absence of the improver. In an embodiment, for example, when the nuclear reprogramming substance is a nucleic acid that encodes a proteinous factor and the iPS cell establishment efficiency improver is a chemical inhibitor, the iPS cell establishment efficiency improver can be added to the medium after the cell is cultured for a given length of time after the gene transfer treatment, because the nuclear reprogramming substance involves a given length of time lag from the gene transfer treatment to the mass-expression of the proteinous factor, whereas the iPS cell establishment efficiency improver is capable of rapidly acting on the cell. In another embodiment, when a nuclear reprogramming substance and an iPS cell establishment efficiency improver are both used in the form of a viral or plasmid vector, for example, both may be simultaneously introduced into the cell.

(e) Improving Establishment Efficiency by Culture Conditions iPS cell establishment efficiency can further be improved by culturing the cells under hypoxic conditions in the nuclear reprogramming process for somatic cells (*Cell Stem Cell,* 5(3): 237-241 (2009); WO 2010/013845). As mentioned herein, the term "hypoxic conditions" means that the ambient oxygen concentration as of the time of cell culture is significantly lower than that in the atmosphere. Specifically, conditions involving lower oxygen concentrations than the ambient oxygen concentrations in the 5-10% $CO_2$/95-90% air atmosphere, which is commonly used for ordinary cell culture, can be mentioned; examples include conditions involving an ambient oxygen concentration of 18% or less. Preferably, the ambient oxygen concentration is 15% or less (e.g., 14% or less, 13% or less, 12% or less, 11% or less and the like), 10% or less (e.g., 9% or less, 8% or less, 7% or less, 6% or less and the like), or 5% or less (e.g., 4% or less, 3% or less, 2% or less and the like). The ambient oxygen concentration is preferably 0.1% or more (e.g., 0.2% or more, 0.3% or more, 0.4% or more and the like), 0.5% or more (e.g., 0.6% or more, 0.7% or more, 0.8% or more, 0.9% or more and the like), or 1% or more (e.g., 1.1% or more, 1.2% or more, 1.3% or more, 1.4% or more and the like).

Although any method of creating a hypoxic state in a cellular environment can be used, the easiest way is to culture cells in a $CO_2$ incubator permitting adjustments of oxygen concentration, and this represents a suitable case. $CO_2$ incubators permitting adjustment of oxygen concentration are commercially available from various manufacturers (e.g., $CO_2$ incubators for hypoxic culture manufactured by Thermo scientific, Ikemoto Scientific Technology, Juji Field, Wakenyaku etc.).

The time of starting cell culture under hypoxic conditions is not particularly limited, as far as iPS cell establishment efficiency is not prevented from being improved compared with the normal oxygen concentration (20%). Although the culture may be started before the somatic cell is contacted with a protein involved in PrS formation or a nucleic acid encoding the same and nuclear reprogramming substance(s), or at the same time as the contact, or after the contact, it is preferable, for example, that the culture under hypoxic conditions be started just after the somatic cell is contacted with the protein involved in PrS formation or the nucleic acid encoding the same and the nuclear reprogramming substance(s), or at a given time interval after the contact [e.g., 1 to 10 (e.g., 2, 3, 4, 5, 6, 7, 8 or 9) days].

The duration of cultivation of cells under hypoxic conditions is not particularly limited, as far as iPS cell establishment efficiency is not prevented from being improved compared with the normal oxygen concentration (20%); examples include, but are not limited to, periods of 3 days or more, 5 days or more, 7 days or more or 10 days or more, and 50 days or less, 40 days or less, 35 days or less or 30 days or less and the like. Preferred duration of cultivation under hypoxic conditions varies depending on ambient oxygen concentration; those skilled in the art can adjust as appropriate the duration of cultivation according to the oxygen concentration used. In an embodiment of the present invention, if iPS cell candidate colonies are selected with drug resistance as an index, it is preferable that a normal oxygen concentration be restored from hypoxic conditions before starting drug selection.

Furthermore, preferred starting time and preferred duration of cultivation for cell culture under hypoxic conditions also vary depending on the choice of nuclear reprogramming substance used, iPS cell establishment efficiency under normal oxygen concentration conditions and the like.

(f) Selection and Confirmation of iPS Cell

After being contacted with nuclear reprogramming substance(s) and the iPS cell establishment efficiency improving factors of the present invention (and other iPS cell establishment efficiency improving factors), the cell can be cultured under conditions suitable for the cultivation of, for example, ES cells. In the case of mouse cells, the cultivation is carried out with the addition of Leukemia Inhibitory Factor (LIF) as a differentiation suppressor to an ordinary medium. Meanwhile, in the case of human cells, it is desirable that basic fibroblast growth factor (bFGF) and/or stem cell factor (SCF) be added in place of LIF. Usually, the cells are cultured in the co-presence of mouse embryo-derived fibroblasts (MEF) treated with radiation or an antibiotic to terminate the cell division thereof, as feeder cells. MEF in common use as feeders include the STO cell and the like; for induction of an iPS cell, the SNL cell [McMahon, A. P. & Bradley, A. Cell 62, 1073-1085 (1990)] and the like are commonly used. Co-culture with these feeder cells may be started before contact of the nuclear reprogramming substance(s) and the iPS cell establishment efficiency improving factors of the present invention, at the time of the contact, or after the contact (e.g., 1-10 days later).

A candidate colony of iPS cells can be selected by a method with drug resistance and reporter activity as indicators, and also by a method based on visual examination of morphology. As an example of the former, a colony positive for drug resistance and/or reporter activity is selected using a recombinant somatic cell wherein a drug resistance gene and/or a reporter gene is targeted to the locus of a gene highly expressed specifically in pluripotent cells (e.g., Fbx15, Nanog, Oct3/4 and the like, preferably Nanog or Oct3/4). Examples of such recombinant somatic cells include MEFs or TTFs from a mouse having the βgeo (which encodes a fusion protein of β-galactosidase and neomycin phosphotransferase) gene knocked-in to the Fbx15 locus [Takahashi & Yamanaka, *Cell,* 126, 663-676 (2006)], MEFs or TTFs from a transgenic mouse having the green fluorescent protein (GFP) gene and the puromycin resistance gene integrated in the Nanog locus [Okita et al., *Nature,* 448, 313-317 (2007)] and the like. Meanwhile, examples of the method of selecting candidate colonies based on visual examination of morphology include the method described by Takahashi et al. in *Cell,* 131, 861-872 (2007). Although the method using reporter cells is convenient and efficient, it is desirable from the viewpoint of safety that colonies be selected by visual examination when iPS cells are prepared for the purpose of human treatment.

The identity of the cells of a selected colony as iPS cells can be confirmed by positive responses to a Nanog (or Oct3/4) reporter (puromycin resistance, GFP positivity and the like) as well as by the formation of a visible ES cell-like colony, as described above. However, to ensure higher accuracy, it is possible to perform tests such as alkaline phosphatase staining, analyzing the expression of various ES-cell-specific genes, and transplanting the cells selected to a mouse to confirm the formation of teratomas.

When a nucleic acid that encodes a protein involved in PrS formation such as Foxh1 is introduced into a somatic cell, the iPS cell obtained is a novel cell distinct from conventionally known iPS cells because of the containment of the exogenous nucleic acid. In particular, when the exogenous nucleic acid is introduced into the somatic cell using a retrovirus, lentivirus or the like, the exogenous nucleic acid is usually integrated in the genome of the iPS cell obtained, so that the phenotype of containing the exogenous nucleic acid is stably retained.

(g) Use of iPS Cell

The iPS cells thus established can be used for various purposes. For example, by utilizing a method of differentiation induction reported with respect to ES cells (for example, see JP 2002-291469 as a method for inducing differentiation into nerve stem cells, JP 2004-121165 as a method for inducing differentiation into pancreatic stem-like cells, JP 2003-505006 as a method for inducing differentiation into hematopoietic cells, JP 2003-523766 as a differentiation induction method via embryonic body formation), differentiation into various cells (e.g., myocardial cells, blood cells, nerve cells, vascular endothelial cells, insulin-secreting cells and the like) from iPS cells can be induced. Therefore, inducing iPS cells using a somatic cell collected from a patient or another person of the same or substantially the same HLA type would enable stem cell therapy by autogeneic or allogeneic transplantation, wherein the iPS cells are differentiated into desired cells (that is, cells of an affected organ of the patient, cells that have a therapeutic effect on disease, and the like), which are transplanted to the patient. Furthermore, because functional cells (e.g., hepatocytes) differentiated from iPS cells are thought to better reflect the actual state of the functional cells in vivo than do corresponding existing cell lines, they can also be suitably used for in vitro screening for the effectiveness and toxicity of pharmaceutical candidate compounds and the like.

The present invention is hereinafter described in further detail by means of the following examples, to which, however, the invention is never limited.

Examples

Materials & Methods
The Policy of Statistical Analyses

All quantitative experiments were conducted at least biological triplicates. We evaluated data by paired t-test by using Kaleida graph software, and P-values less than 0.05 were considered significant indicated as asterisks. Error bars indicate standard deviation.

Cell Culture

We obtained HDF from the Japanese Collection of Research Bioresources. HDF, PLAT-E and PLAT-GP were maintained in Dulbecco's modified eagle medium (DMEM, Nacalai tesque) containing 10% fetal bovine serum (FBS, Thermo) and 0.5% penicillin and streptomycin (Pen/Strep, Invitrogen).

H1 and H9 ESCs were obtained from WiCELL, and maintained in Primate ESC medium (ReproCELL) supplemented with 4 ng/ml recombinant human basic fibroblast growth factor (bFGF, Wako) on mitomycin C (MMC)-inactivated SNL feeders, or in mTeSR1 (Veritas) on Matrigel-coated plates (BD biosciences) as described previously. Normal human epidermal keratinocytes (NHEK, Lonza), human astrocytes (HA, Cell applications), normal human bronchial epitheliums (NHBE, Lonza), adipose tissue-derived stem cell (ASC, Invitrogen) and prostate epithelium (PrE, Lonza) were maintained in manufacturer's recommended conditions.

Reprogramming

Reprogramming experiments were performed as described previously (Cell 131, 861-872 (2007)). To generate retroviral particles, we introduced retroviral vectors into PLAT-E or PLAT-GP by using FuGENE 6 transfection reagent (Roche) as manufacturer's protocol. Next day, the medium was replaced with fresh one and incubate them for another 24 hours. The virus-containing supernatant was collected, filtrated through a 0.45 μm pore size cellulose acetate filter (Whatman) and was added 4 μg/ml Polybrene (Nacalai Tesque). Then, we mixed appropriate combination and exposed to HDF carrying mouse Slc7a1 gene overnight. This point was designated as day 0. For transduction of retroviruses to cell lines except HDF, we performed spinfection at 700×g for an hour with VSVG-pseudotyped pantropic viruses produced by PLAT-GP. We harvested the cells at day 7 post-transduction, and re-plated them onto MMC-inactivated SNL feeders for generation of iPSC. Next day, the medium was replaced with Primate ESC medium supplemented with 4 ng/ml bFGF, and changed every other day.

Gene Silencing

For short-term gene silencing, Stealth siRNA for FOXH1 (equal amount mixture of HSS189664, HSS113216 and HSS113217) or Negative control Mid GC (Invitrogen) were transfected into human ESC/iPSC by using Lipofectamine RNAi Max (Invitrogen) according to manufacturer's protocol on day 0 of PrS differentiation protocol. For stable knockdown during reprogramming, we introduced pMKO.1-puro retroviral vector (#8452, Addgene) encoding shRNA against genes of interest, at the same timing of OSKM transduction. The target sequences of FOXH1 shRNA 1, 3 and 6 are 5'-CACCTCCTACTTGCCTATCTA-3' (SEQ ID NO:1), 5'-GCCTATCTACACTCCCAATGT-3' (SEQ ID NO:2) and 5'-TGCAGCCTGTGAGGCTCTTAA-3' (SEQ ID NO:3), respectively.

Flow Cytometry and Fluorescence Activated Cell Sorting (FACS)

We harvested the cells at indicated time points by treatment with 0.25% trypsin/1 mM EDTA (Invitrogen) or Accutase (Invitrogen). Fixation and permeabilization were performed before antibody staining with 4% paraformaldehyde and 0.2% TritonX-100, respectively. At least, $5 \times 10^4$ cells were analyzed for quantification in all experiments by using FACS Aria II (BD biosciences). Cell sorting was also performed by using FACS Aria II. We used following antibodies; Alexa 488-conjugated TRA-1-60 (1:20, 560173, BD biosciences), Alexa 488-conjugated SSEA-4 (1:20, 506348, BD biosciences), fluorescein isothiocyanate (FITC)-conjugated TRA-1-2-49/6E (1:5, FCMAB133, Millipore), allophycocyanin (APC)-labeled TRA-1-85 (1:5, FAB3195A, R&D systems), APC-labeled anti-C—X—C chemokine receptor type 4 (CXCR4) mouse monoclonal antibody (1:5, FAB170A, R&D systems), PE-labeled anti-platelet-derived growth factor receptor alpha (PDGFRA) mouse monoclonal antibody (1:5, 556002, BD Pharmingen), APC-conjugated anti-BRACHYURY (1:5, IC20851A, R&D systems), anti-polysialylated neuronal cell adhesion molecule (PSA-NCAM) antibody (MAB5324, Millipore) and Alexa 647-conjugated anti-mouse IgM antibody (1:500, A-21238, Invitogen).

Magnetic Activated Cell Sorting (MACS)

The harvested cells by using 0.25% Trypsin/1 mM EDTA were passed through a 40 μm pore size cell strainer (BD biosciences) to remove the cell debris. The cells were incubated with PE-conjugated TRA-1-60 (1:5, 560193, BD Pharmingen) or SSEA-1 (1:5, 560866, BD Pharmingen), and then with anti-PE microbeads (130-048-801, Miltenyibiotec). Cell separation was performed with serial two column mode of AutoMACS (Miltenyibiotec). After separation, we confirmed the purity by flow cytometry.

Plasmid Construction

The open reading frames (ORF) of genes used in this study were amplified by PCR, subcloned into pENTR-D-TOPO (Invitrogen) and verified by sequencing. ORF were transferred to expression vectors such as pMXs-gw, pMXs-gw-IG, PB/CAG-gw-IP or PB/CAG-gw-IB by using Gateway LR reaction system (Invitrogen) according to manufacturer's protocol. For generation of cGR-fused construct, stop codon-lacking GLIS1 and FOXH1 were amplified by PCR and cloned into pCR2.1-TOPO (Invitrogen). An EcoRI/SpeI fragment of each gene cloned in pCR2.1 and a SpeI/NotI fragment of pPyCAG-cGR-IP were inserted into the EcoRI/NotI site of pMXs. A knockdown vector for human p53 gene (pMKO.1-puro p53 shRNA2, #10672) was purchased from Addgene.

Quantitative Reverse-Transcription Polymerase Chain Reaction

Total RNA was purified from cell lysates treated with Qiazol reagent (Qiagen), and incubated with the Turbo DNA free kit (Ambion) to remove genomic DNA. The reverse transcription reaction was performed with 1 µg of DNase-treated RNA by using the Rever tra ace-α-kit (Toyobo) and oligo $dT_{20}$ primer. Primer sequences for each gene are provided in Table 3.

TABLE 3

| SEQ ID NO | Primer | Sequence (5' to 3') | Purpose |
|---|---|---|---|
| 4 | hOCT3/4-S1165 | GAC AGG GGG AGG GGA GGA GCT AGG | qRT-PCR for endogenous OCT3/4 |
| 5 | hOCT3/4-AS1283 | CTT CCC TCC AAC CAG TTG CCC CAA AC | |
| 6 | hOCT3/4-S944 | CCC CAG GGC CCC ATT TTG GTA CC | qRT-PCR for total OCT3/4 |
| 7 | hOCT3/4-AS | ACC TCA GTT TGA ATG CAT GGG AGA GC | |
| 8 | hSOX2-S1430 | GGG AAA TGG GAG GGG TGC AAA AGA GG | qRT-PCR for endogenous SOX2 |
| 9 | hSOX2-AS1555 | TTG CGT GAG TGT GGA TGG GAT TGG TG | |
| 10 | hSOX2-S875 | TTC ACA TGT CCC AGC ACT ACC AGA | qRT-PCR for total SOX2 |
| 11 | hSOX2-AS | TCA CAT GTG TGA GAG GGG CAG TGT GC | |
| 12 | hNANOG-S1678 | TGG CTG CCG TCT CTG GCT ATA GAT | qRT-PCR for NANOG |
| 13 | hNANOG-AS1797 | AAG CCT CCC AAT CCC AAA CAA TAC | |
| 14 | hKLF2-S811 | ACT CAC ACC TGC AGC TAC GC | qRT-PCR for KLF2 |
| 15 | hKLF2-AS951 | GTC TGA GCG CGC AAA CTT CC | |
| 16 | hKLF4-S1094 | CAT GCC AGA GGA GCC CAA GCC AAA GAG GGG | qRT-PCR for KLF4 |
| 17 | hKLF4-AS1225 | CGC AGG TGT GCC TTG AGA TGG GAA CTC TTT | |
| 18 | hKLF5-S1344 | TCC AAA TTT ACC CAC CAC CCT GCC AG | qRT-PCR for KLF5 |
| 19 | hKLF5-AS1536 | TCC AGT CGC AGC CTT CCC AGG TAC AC | |
| 20 | hMYC-S547 | GCC GCC GCC TCA GAG TGC ATC GAC | qRT-PCR for c-MYC |
| 21 | hMYC-AS947 | CGA GTG GAG GGA GGC GCT GCG TAG | |
| 22 | hMYCN-S835 | GTG GTC ACT GTG GAG AAG CGG CGT TC | qRT-PCR for MYCN |
| 23 | hMYCN-AS1047 | GAC GTG GGG ACG CCT CGC TCT TTA TC | |
| 24 | hMYCL-S581 | ACC CCC TGG ATC CCT GCA TGA AGC | qRT-PCR for MYCL1 |
| 25 | hMYCL-AS724 | TCC TCA TCT TCC TTT TCC CCT GCA GC | |
| 26 | hLIN28A-S229 | AGT AAG CTG CAC ATG GAA GG | qRT-PCR for LIN28A |
| 27 | hLIN28A-AS414 | CCT GTC TCC TTT TGA TCT GC | |
| 28 | hLIN28B-S477 | AAA GGC TTT GAG TCA ATA CGG GTA AC | qRT-PCR for LIN28B |
| 29 | hLIN28B-AS581 | GGC CAC CAC AGT TGT AGC ATC TAT CT | |
| 30 | hGDF3-S248 | GCT ACG TAA AGG AGC TGG GCG TC | qRT-PCR for GDF3 |
| 31 | hGDF3-AS372 | CCC TTT CTT TGA TGG CAG ACA GG | |
| 32 | hLEFTY2-S715 | AAC CGC ACC TCC CTC ATC GAG TC | qRT-PCR for LEFTY2 |
| 33 | hLEFTY2-AS840 | GCT CCC TCT GCA CCG ACA CCT GT | |
| 34 | hGSC-S721 | CAG CTG GCC CGG AAA GTG CAC CTC | qRT-PCR for GSC |
| 35 | hGSC-AS855 | TTC TCC GGT GAC GCC TTC GAC GAC | |
| 36 | hHEX-S623 | ATC GAC GCG CTA AAT GGA GGA GAC | qRT-PCR for HEX |
| 37 | hHEX-AS757 | GGA GGG CGA ACA TTG AGA GCT ATC | |

TABLE 3-continued

| SEQ ID NO | Primer | Sequence (5' to 3') | Purpose |
|---|---|---|---|
| 38 | hSFRP5-S698 | ACC AAG ATC TGC GCC CAG TGT GAG | qRT-PCR for SFRP5 |
| 39 | hSFRP5-AS806 | AAT CAG CTT CCG GTC CCC ATT CTC | |
| 40 | hDKK1-S593 | CGA GGA GAA ATT GAG GAA ACC ATC | qRT-PCR for DKK1 |
| 41 | hDKK1-AS707 | TGA CCG GAG ACA AAC AGA ACC TTC | |
| 42 | hGATA4-S2044 | CGG GTG TTG GAT TTT CTC AGA TGC | qRT-PCR for GATA4 |
| 43 | hGATA4-AS2179 | AAA CCC ACG TCT AGC CAC AGT G | |
| 44 | hTBX6-S771 | CTC CTT CCG CTT CCC CGA GAC CAC | qRT-PCR for TBX6 |
| 45 | hTBX6-AS913 | GCC CCG CAG TTT CCT CTT CAC ACG | |
| 46 | hHNF3β-qS | GGA GCG GTG AAG ATG GAA | qRT-PCR for HNF3β |
| 47 | hHNF3β-qAS | TAC GTG TTC ATG CCG TTC AT | |
| 48 | hSox17-S423 | CGC TTT CAT GGT GTG GGC TAA GGA CG | qRT-PCR for SOX17 |
| 49 | hSox17-AS583 | TAG TTG GGG TGG TCC TGC ATG TGC TG | |
| 50 | hBrachyury-S1807 | CAA GGC CCA GGT CCC GAA AGA TGC | qRT-PCR for T |
| 51 | hBrachyury-AS1939 | GGT GCC GTG TGC TCC TCC ACT GC | |
| 52 | hFLK1-qS | TGA TCG GAA ATG ACA CTG GA | qRT-PCR for KDR |
| 53 | hFLK1-qAS | CAC GAC TCC ATG TTG GTC AC | |
| 54 | hPAX6-S1206 | ACC CAT TAT CCA GAT GTG TTT GCC CGA G | qRT-PCR for PAX6 |
| 55 | hPAX6-AS1497 | ATG GTG AAG CTG GGC ATA GGC GGC AG | |
| 56 | hMIXL1-S350 | CGC GCT CAC CCT GCT CCC CGA GTC | qRT-PCR for MIXL1 |
| 57 | hMIXL1-AS538 | TTG GTT CGG GCA GGC AGT TCA CAT C | |
| 58 | hGLIS1-S2434 | CAC CTC GCC CAC CTG CTG TCG CTC | qRT-PCR for endogenous GLIS1 |
| 59 | hGLIS1-AS2604 | GTG CGC CCA GCT CAA GCT CGG ATG | |
| 60 | hGLIS1-S1421 | TGC CCC CAT CCT CTC AGA GCC ATT C | qRT-PCR for total GLIS1 |
| 61 | hGLIS1-AS1578 | CAG CCA TCC GGT AGC AGT CGC CAT AG | |
| 62 | G3PDH-S | ACC ACA GTC CAT GCC ATC AC | qRT-PCR for G3PDH |
| 63 | G3PDH-AS | TCC ACC ACC CTG TTG CTG TA | |
| 64 | hFOXH1-S709 | TTG GTG ATT CAG GCC GCT CCC TC | qRT-PCR for FOXH1 |
| 65 | hFOXH1-AS848 | GTC CTT GGG CAC CTT GCG GAA GC | |
| 66 | hLHX1-S1957 | CGG TCT GCG GAG TTC GTG GTT GT | qRT-PCR for LHX1 |
| 67 | hLHX1-AS2139 | GAC AGC AGC TGC GCG GAT CCC AG | |
| 68 | hCER1-S553 | GGA CAG TGC CCT TCA GCC AGA CTA | qRT-PCR for CER1 |
| 69 | hCER1-AS659 | TGG CAG GCA AAC AGT GAG AGC AGG | |
| 70 | hFOXF1-S1230 | ACC CTG GAC CGG CAC AAG AAA CTG | qRT-PCR for FOXF1 |
| 71 | hFOXF1-AS1338 | GCC AAC CGC AGC GCT GTG TCT TTG | |
| 72 | hID3-S871 | ACT TCG CCC TGC CCA CTT GAC TTC | qRT-PCR for ID3 |
| 73 | hID3-AS1045 | CAG CCA CTC CTT CCA CAC CTC CAC | |
| 74 | hEVX1-S1049 | CCG CCT TCA CCC GAG AGC AGA TTG | qRT-PCR for EVX1 |
| 75 | hEVX1-AS1179 | TTG TCC TTC ATG CGC CGG TTC TGG | |
| 76 | hBMP4-S678 | TAC CGG CTT CAG TCT GGG GAG GAG | qRT-PCR for BMP4 |
| 77 | hBMP4-AS798 | TTC ACT GGT CCC TGG GAT GTT CTC | |
| 78 | hOCT3-CR1-F1 | TTT TTT GGA TGG TGG AGA GAG A | Methylome of OCT3/4 CR1 |
| 79 | hOCT3-CR1-R1 (Biotinated) | CAC CAT TAC CAC CAC CAT TAA AC | |
| 80 | hOCT3-CR1-S1 | ATG GGT GGA GGA GAG | |
| 81 | hOCT3-CR2-F 1 | GGG TGT GGA GAA AAA ATA TTT GAT TTT AGG | Methylome of OCT3/4 CR2 |
| 82 | hOCT3-CR2-R1 (Biotinated) | CCA AAC CCA TTC AAA AAT TAA ACA CTT A | |
| 83 | hOCT3-CR2-S1 | GGG GGT AGG ATA ATG | |
| 84 | hNANOG-CR1-F1 | TTT GTA TTA TAA TGG TTT GGT GAG ATT G | Methylome of NANOG CR1 |
| 85 | hNANOG-CR1-R1 (Biotinated) | CCT ACT AAC CCA CCC TTA TAA ATT | |
| 86 | hNANOG-CR1-S1 | GTT TTG GTG AGA TTG G | |
| 87 | h-OCT3/4-DMR pyro-F1 | GTG GGA TTG GGA GGA GAG A | Methylome of OCT3/4 5' UTR |
| 88 | h-OCT3/4-DMR pyro-R1 (Biotinated) | CCC CTA ACC CAT CAC CTC C | |
| 89 | h-OCT3/4-DMR pyro-S1 | GTA AGT TTT TAT TTT ATT AGG TTT | |

TABLE 3-continued

| SEQ ID NO | Primer | Sequence (5' to 3') | Purpose |
|---|---|---|---|
| 90 | hGLIS1 ChIP S1 | ACA CAG AAC GTT GCA GGA GGG TAT C | ChIP-PCR for GLIS1 locus |
| 91 | hGLIS1 ChIP AS1 | AAA TGC CTG CTG AGT GTT ATT GCT G | |
| 92 | hGLIS1 ChIP S2 | AGG GCC TGA GAC AGA ACA GCA CTG G | |
| 93 | hGLIS1 ChIP AS2 | GAG TTC ACC ACC TAC CGT GCA CCA G | |
| 94 | hGLIS1 ChIP S3 | TTG AGT AAT TTC TGG TGC GAG GCT G | |
| 95 | hGLIS1 ChIP AS3 | GCT TTA TGG TGG TGT GGG TGT GTG C | |

Microarray and Gene Ontology Analyses

Fifty-nanograms of total RNA was labeled with Cyanine 3-CTP and used for hybridization with SurePrint G3 Human GE 8×60K (G4112F, Agilent technologies) or SurePrint G3 Mouse GE 8×60K (G4852A) with the one color protocol. The arrays were scanned with a Microarray Scanner System (G2565BA, Agilent technologies), and extracted signals were analyzed by using GeneSpring version 11 software (Agilent technologies). Gene expression values were normalized by the 75% percentile shifts. The component 1 and 2 genes in FIGS. 2c, d and e were narrowed down by cutting off as the rate of contribution was less than −0.6. Microarray datasets, GSE28024, was downloaded from Gene Expression Omnibus (GEO) in National Institute for biotechnology Information (NCB') website. Gene ontology analyses were performed by using EASE program on DAVID bioinformatics database website (http://david.abcc.ncifcrf.gov/home-.jsp).

Embryoid Body Formation

Small clamps of human ESC/iPSC transferred to low-binding plate (Nunc) in DMEM/F12 containing 20% KSR, 1% Glutamax, 1% NEAA, 100 nM 2-ME, and 0.5% Pen/Strep. The medium was changed every other day. After 8-days floating culture, aggregates were transferred onto gelatinized plates and cultured for another 8 days. The medium was changed every other day.

Primitive Streak Differentiation

Differentiation of human ESC/iPSC into primitive streak was performed as described previously (*Nat Biotechnol* 28, 1187-1194, doi:nbt.1683 [pii]). In brief, the single cell suspension of human ESC/iPSC were plated onto fibronectin-coated plate (BD biosciences) in DMEM/F12 supplemented with 1% Insulin-Transferrin-Selenite (ITS, Invitrogen), 1% Glutamax, 1% NEAR, 2% B27 (Invitrogen), 100 nM 2-ME, and 0.5% Pen/Strep. We added 3 µM CHIR99021 (Stemgent) and 50 ng/ml Activin A for day 1, 3 µM CHIR99021, 25 ng/ml Activin A and 20 ng/ml bFGF for day 2, 3 µM CHIR99021, 10 ng/ml Activin A, 20 ng/ml bFGF and 40 ng/ml BMP4 (R&D systems) for day 3.

Endoderm Differentiation

Endoderm differentiation was performed as described previously with slight modification (*Proc Natl Acad Sci USA* 109, 12538-12543, doi:10.1073/pnas.1209979109 (2012)). The single cell suspension of human pluripotent stem cells were plated onto Matrigel-coated plate in RPMI1640 (Invitrogen) containing 2% 327, 100 ng/ml Activin A, 3 µM CHIR99021 and 0.5% Pen/Strep. We added 0.5 mM sodium butyrate (Sigma) for day 1 to 3, and then carried out sodium butyrate-free culture to day 7.

Mesoderm Differentiation

The single cell suspension of human pluripotent stem cells were plated onto Collagen I-coated plate (BD biosciences) in DMEM/F12 containing 2% B27, 100 ng/ml Activin A, 3 µM CHIR99021 and 0.5% Pen/Strep. Forty eight hours later, the medium was replaced with DMEM/F12 supplemented with 2% B27, 25 ng/ml BMP4, and 0.5% Pen/Strep. The medium was changed every other day to day 8.

Neural Differentiation

Neural differentiation protocol with dual SMAD inhibition was according to previous report (*Nat Biotechnol* 27, 275-280 (2009); *J Neurosci Res* 89(2), 117-126. doi: 10.1002/jnr.22547. Epub 2010 Dec. 8). The single cell suspension of pluripotent stem cells were transferred to Lipidure-coated low binding 96-well plate (NOF corporation) in DMEM/F12 containing 5% KSR, 1% NEAA, 1% Glutamax, 100 nM 2-ME, 2 µM Dorsomorphin (Stemgent) and 10 µM SB431542 (Stemgent). The medium was changed at day 5, 8 and 11. Differentiation period was 14 days.

Immunocytochemistry

The cells were fixed with 4% paraformaldehyde and permeabilized with PBS containing 5% goat or donkey normal serum (Chemicon), 1% bovine serum albumin (BSA; Nacalai Tesque) and 0.2% TritonX-100 (Nacalai Tesque). Samples were incubated with primary antibodies for SOX17 (1:200, AF1924, R&D systems), α-smooth muscle actin (1:600, M085101, DAKO) and NESTIN (1:1000, ab5968, Abcam) which were diluted in staining solution (PBS containing 1% BSA) at 4° C. overnight. After washing with PBS, samples were exposed to staining solution containing fluorescence-conjugated secondary antibodies such as Alexa 488-conjugated anti-goat IgG (1:500, A-11055, Invitrogen), Alexa 546-conjugated anti-mouse IgG (1:500, A-11030, Invitrogen) or Alexa 488-conjugated anti-rabbit IgG (1:500, A-11034, Invitrogen), and Hoechst 33342 (1 µg/ml, H3570, Invitrogen). Images were obtained by using BZ9000 (KEYENCE).

Pyro-Sequencing

Five-hundred micrograms of purified genomic DNA was used for bisulfite CT conversion with EZ DNA methylation kit (Zymo research) according to manufacturer's recommendation. Resultant DNA samples were used for PCR with biotinated primers as templates, and amplified products were analyzed by Pyromark (Qiagen). Primer sequences were provided in Table 3.

Teratoma Formation and Histological Analyses

Approximately $3 \times 10^5$ harvested cells suspended in DMEM/F12 containing 10 µM Y-27632 were injected into testes of severe combined immunodeficiency mice (6 weeks old) by using a Hamilton syringe. After 8 to 10 weeks, tumors were dissected and fixed with 4% paraformaldehyde and 70% ethanol in sequence. Paraffin-embedded sections were stained with hematoxylin and eosin. Images were obtained by using BZ9000.

Results

Nascent Reprogrammed Cells are Similar to PrS in Gene Expression

Figure 1B:
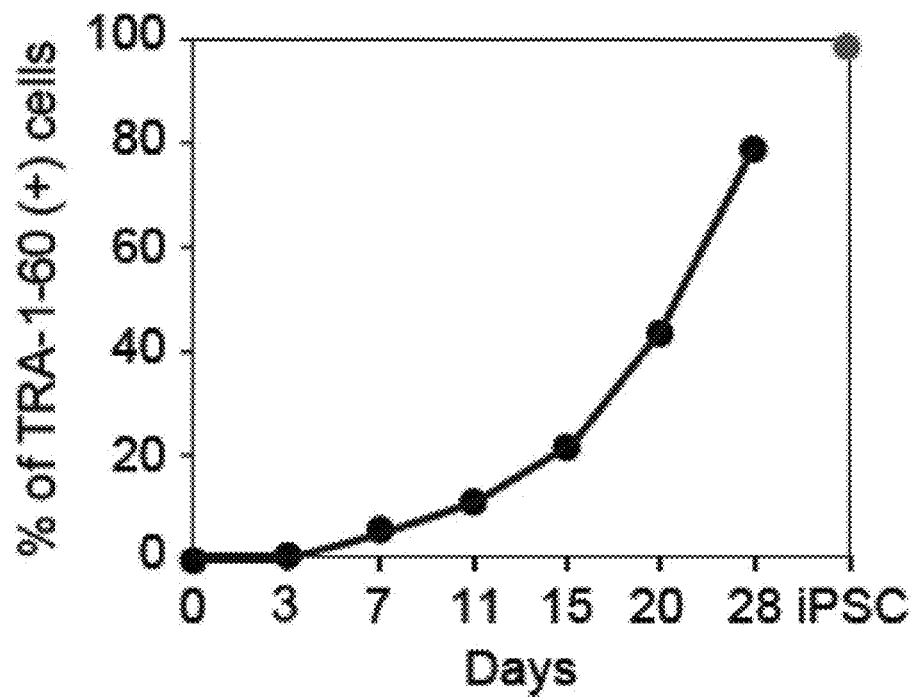
Figure 1C:
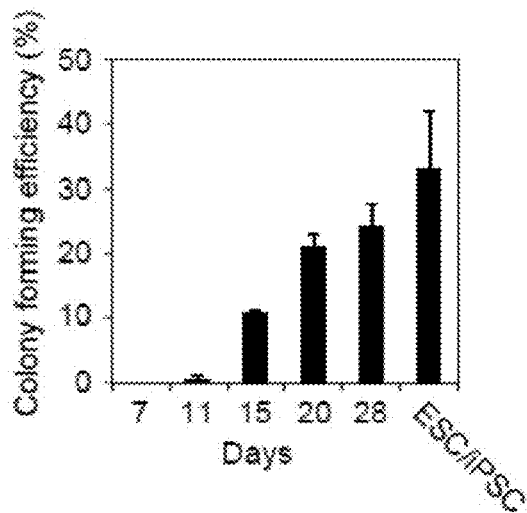
Figure 1D:
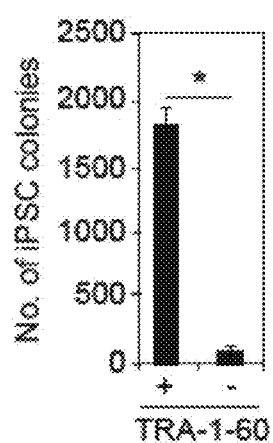
Figure 1E:
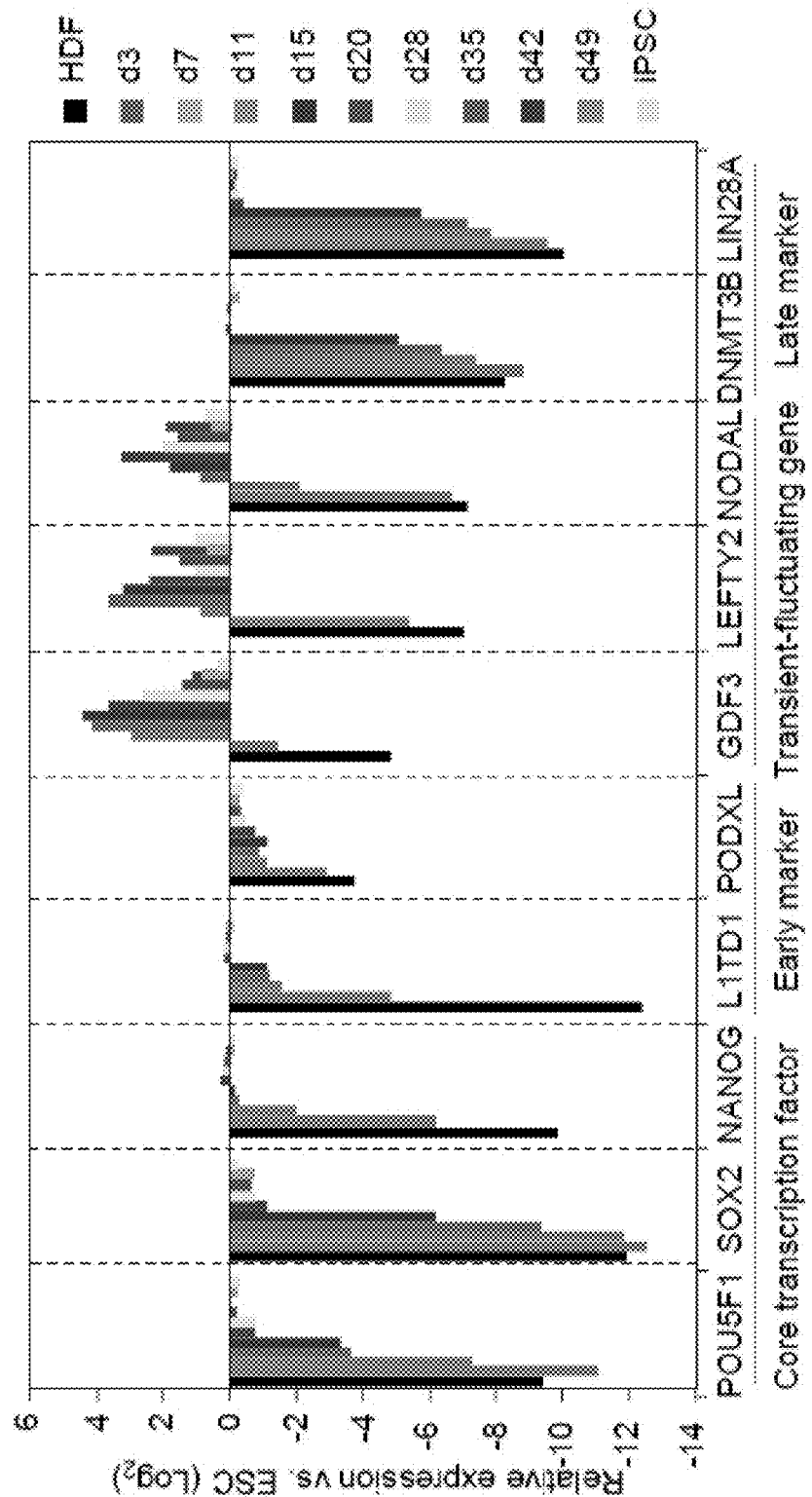

Large numbers of non-reprogrammed cells during induction of induced pluripotent stem cell (iPSC) inhibit accurate analyses of the reprogramming process. To overcome this issue, we used a pluripotent cell-specific surface antigen, TRA-1-60 to capture nascent reprogrammed cells (FIG. 1a). TRA-1-60 positive (+) cells initially appeared in human dermal fibroblast (HDF) culture at day 4 post-transduction of OSKM (FIG. 1b). We confirmed that most of induced pluripotent stem cell (iPSC) colonies were derived from TRA-1-60 (+) cells purified by magnetic activated cell sorting 7 days after transduction (FIG. 1d). The ability of TRA-1-60 (+) cells to form iPSC colonies also gradually increased and reached to an efficiency similar to ESCs/iPSCs on day 20 or 28 (FIG. 1c). In TRA-1-60 (+) cells, pluripotent stem cell markers such as NANOG progressively increased (FIG. 1e) and OSKM transgenes were silenced.

Figure 2A:
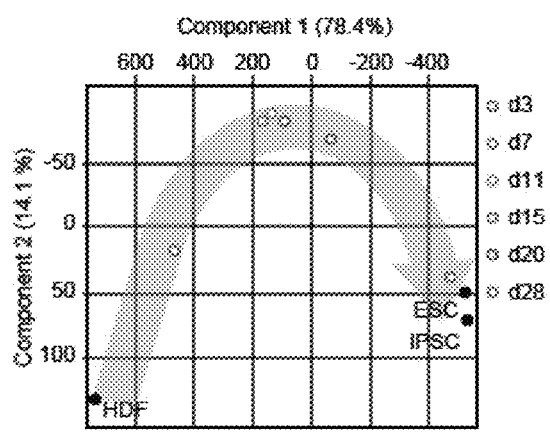
Figure 2B:
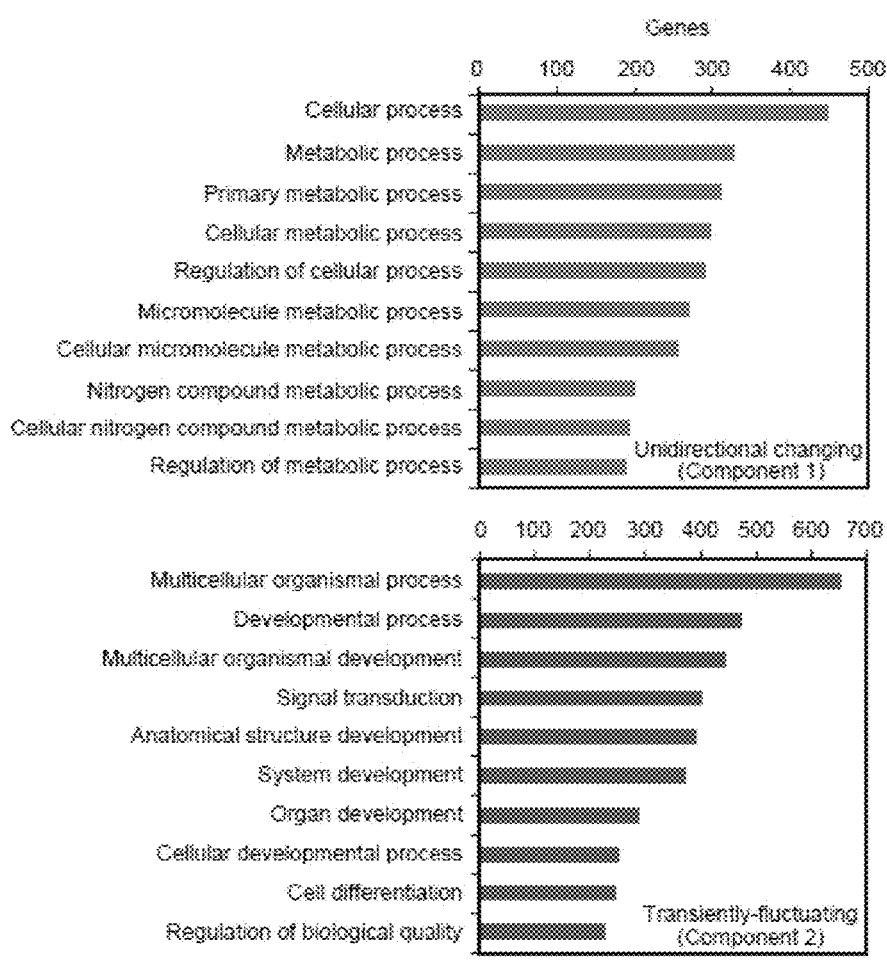
Figure 2C:
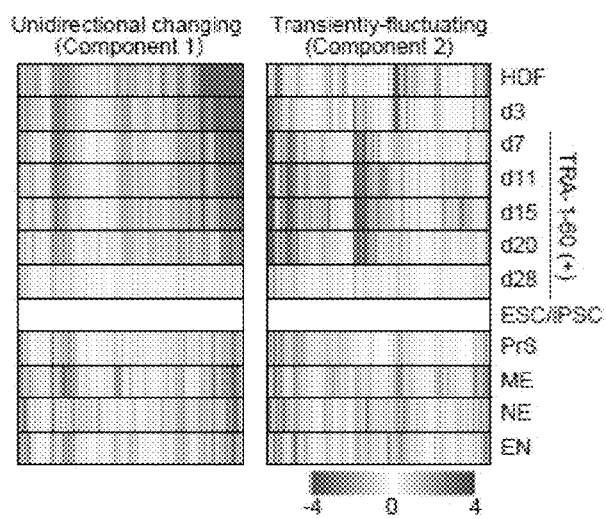
Figure 2D:
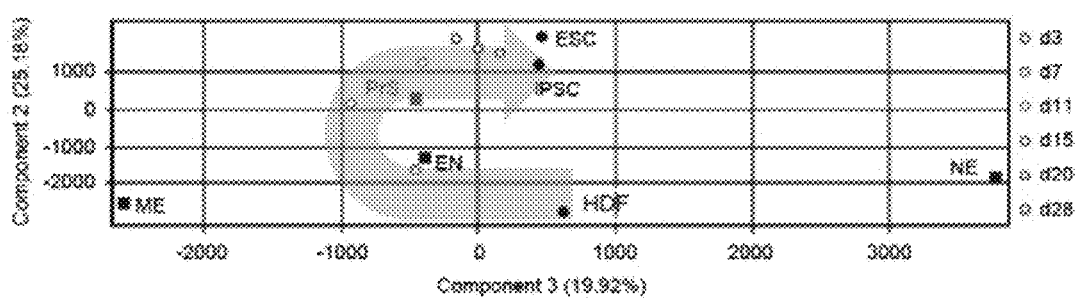

We examined the global and time-course gene expression patterns of purified TRA-1-60 (+) cells with DNA microarrays. We predicted that most genes in TRA-1-60 (+) cells would show expression patterns somehow between HDFs and established iPSCs. Preliminary principle component analysis (PCA) identified component 1 characterized with gradual increases in ESC/iPSC-enriched genes and decreases in fibroblast-enriched genes, as expected (FIG. 2a). However, component 2 revealed substantial numbers of genes that showed transient fluctuation during iPSC generation, suggesting that the route from fibroblasts to iPSCs was not simple or straightforward (FIG. 2a). Gene ontology analyses showed that genes included in component 2 were mainly classified in processes related to "development" (FIG. 2b, lower panel). We compared gene expression of TRA-1-60 (+) cells with three germ lineages, including mesoderm (ME), endoderm (EN), and neuroectoderm (NE), as well as PrS, which were all differentiated from ESC/iPSC (FIG. 2c). PCA analyses showed that nascent reprogrammed cells are most similar to PrS in gene expression (FIG. 2d).

Figure 2E:
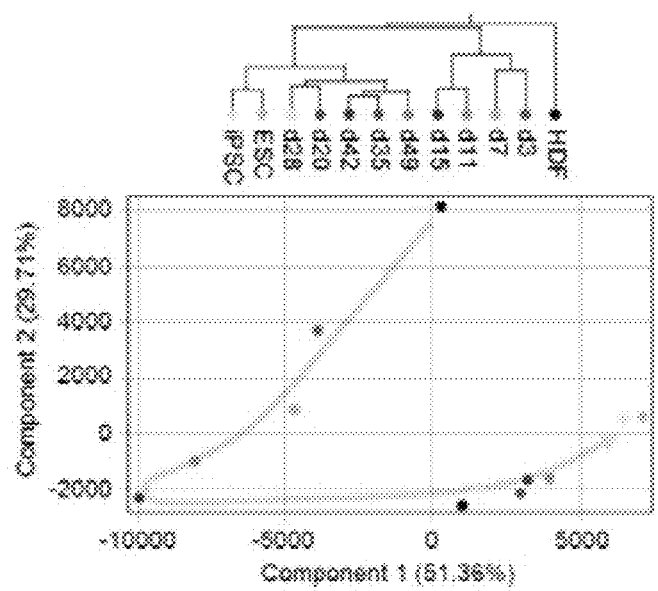
Figure 2F:
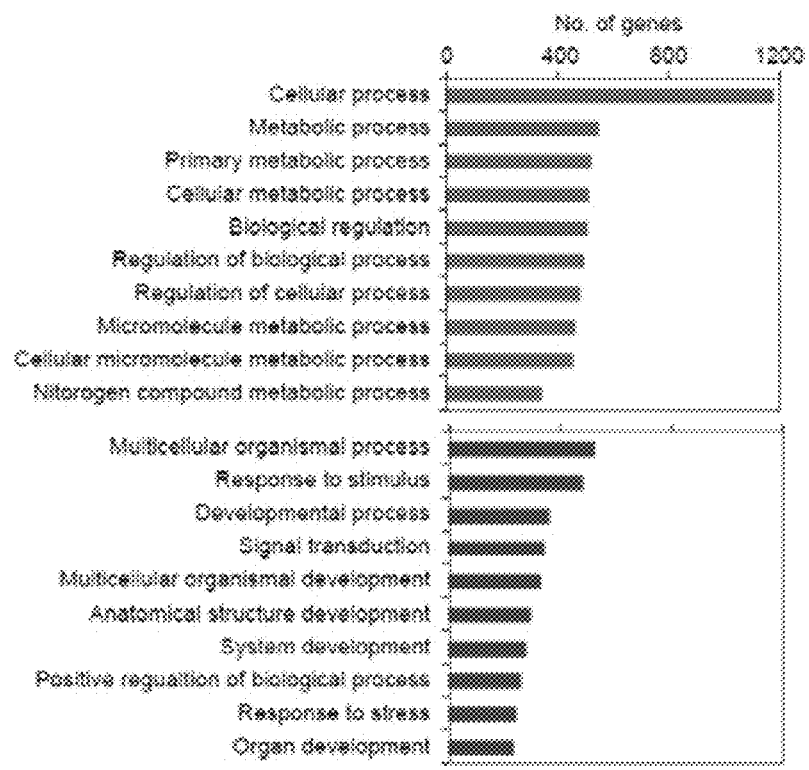

Further PCA analyses revealed that the expression levels of significant number of genes in TRA-1-60 (+) cells were not intermediate between HDFs and iPSCs, but were transiently activated or suppressed during iPSC generation (FIG. 2e). Gene ontology analyses demonstrated that transiently-downregulated genes were mainly categorized as metabolic terms (FIG. 2f, upper panel). On the other hand, transiently-activated genes were associated with terms related to development (FIG. 2f, lower panel). The hierarchical clustering suggested that the fate of TRA-1-60 (+) cells in the first-half of reprogramming (d3-15) verged to those of epithelial cells including epidermis (EDM) (green box in FIG. 2g). Actually, in this stage, some EDM-associated genes were transiently increased, although the correlation coefficient between EDM and nascent reprogrammed cells on day 3-15 were 0.9082-0.9105. Furthermore, the drastic suppression of mesenchymal genes and activation of epithelial genes were observed (FIG. 2h). These data suggest that epitheliarization is one of dominant events in TRA-1-60 (+) intermediate cells in first-half of reprogramming.

Nascent Human Reprogrammed Cells Transiently Acquire a PrS-Like State

Figure 2G:
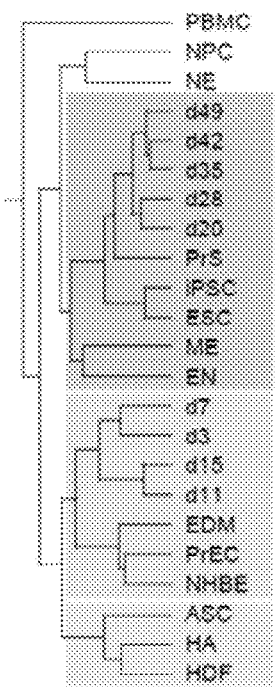
Figure 2H:
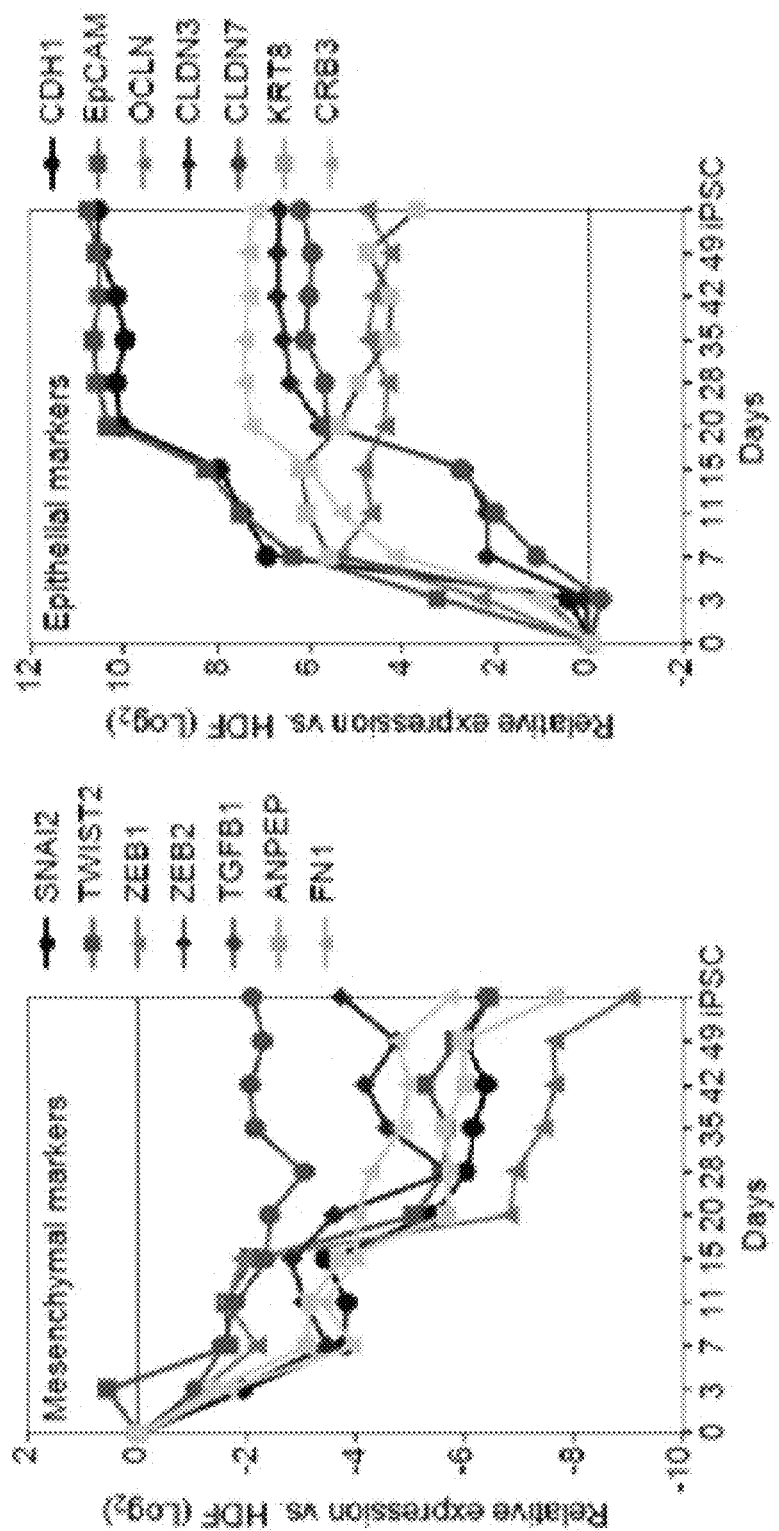

We found that TRA-1-60 (+) cells in the last-half of reprogramming (d20-49) were involved in the cluster with not only ESCs/iPSCs but also differentiated lineages such as mesoderm (ME), endoderm (EN) and primitive streak (PrS) which have early mesendodermal features (red box in FIG. 2g). The PCA and the hierarchical clustering for the comparison of TRA-1-60 (+) cells with differentiated lineages including EDM and PrS showed that the route of reprogramming made a close passage to PrS in the last-half of reprogramming (FIG. 3a).

Figure 3B:
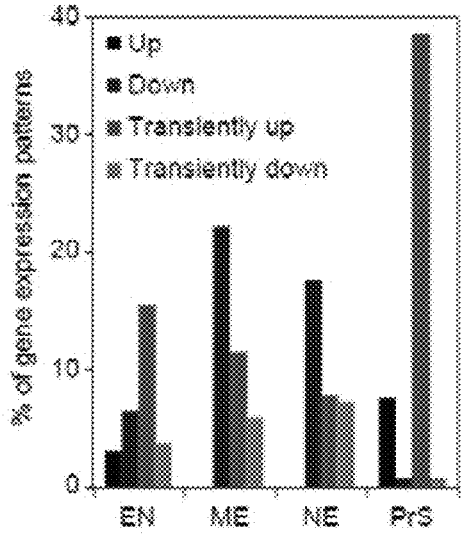
Figure 3C:
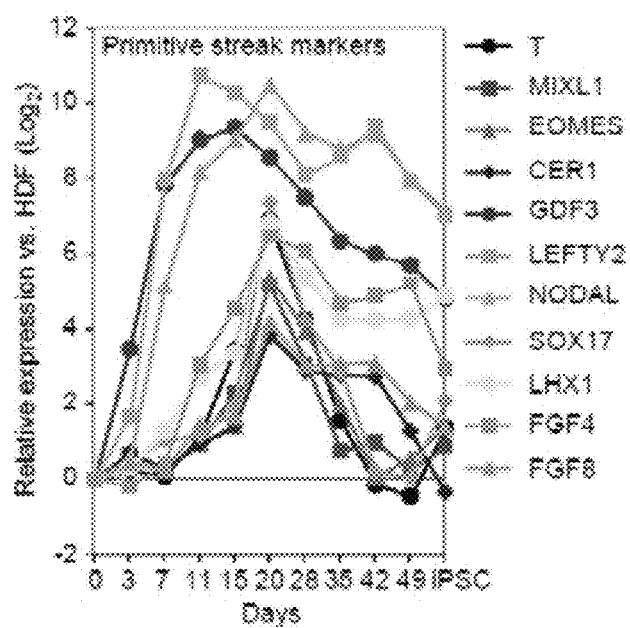
Figure 4A:
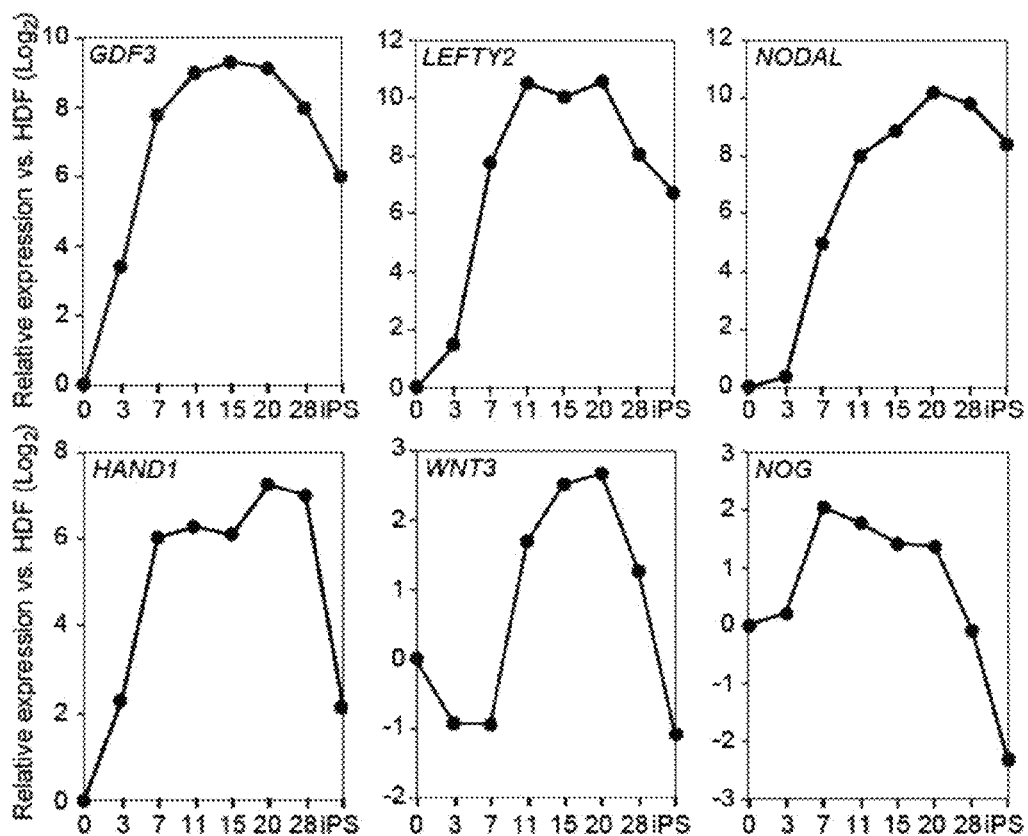
Figure 4B:
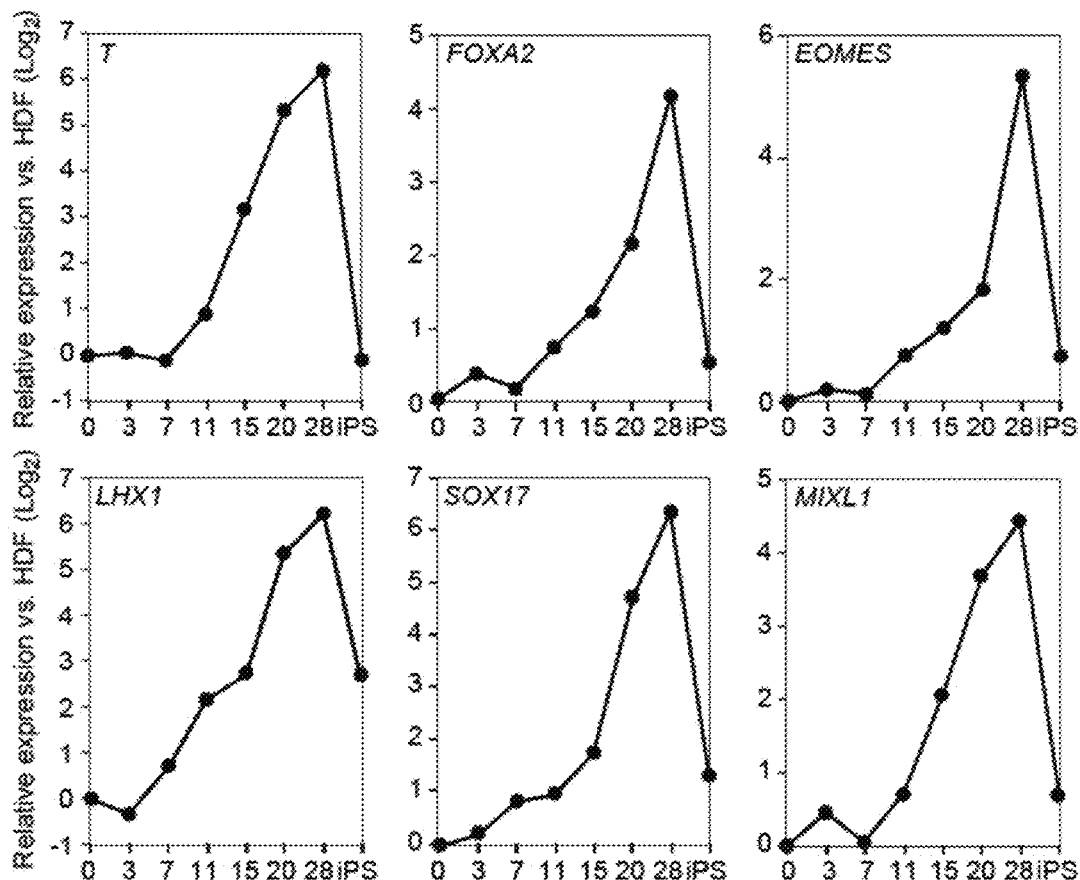

We then checked the expression levels of marker genes for various developmental lineages. Marker genes for PrS such as BRACHYURY (T), GDF3, LEFTY2, MIXL1, LHX1, and NODAL showed a transient activation during iPSC generation in TRA-1-60 (+) cells (FIG. 3c). Approximately 40% of PrS-enriched genes were included in transiently-upregulated genes in TRA-1-60 (+) cells (FIG. 3b). Genes such as GDF3, LEFTY2, NODAL, HAND1, WNT3 and NOG were induced at as early as day 3 (FIG. 4a). On the other hand, genes such as T, FOXA2, EOMES, LHX1, SOX17 and MIXL1 rose up at relative late stages at day 15 or later (FIG. 4b). In contrast, marker genes for other lineages, including pluripotent stem cell, ME, EN and neuroectoderm (NE), did not show such transient changes.

Figure 3A:
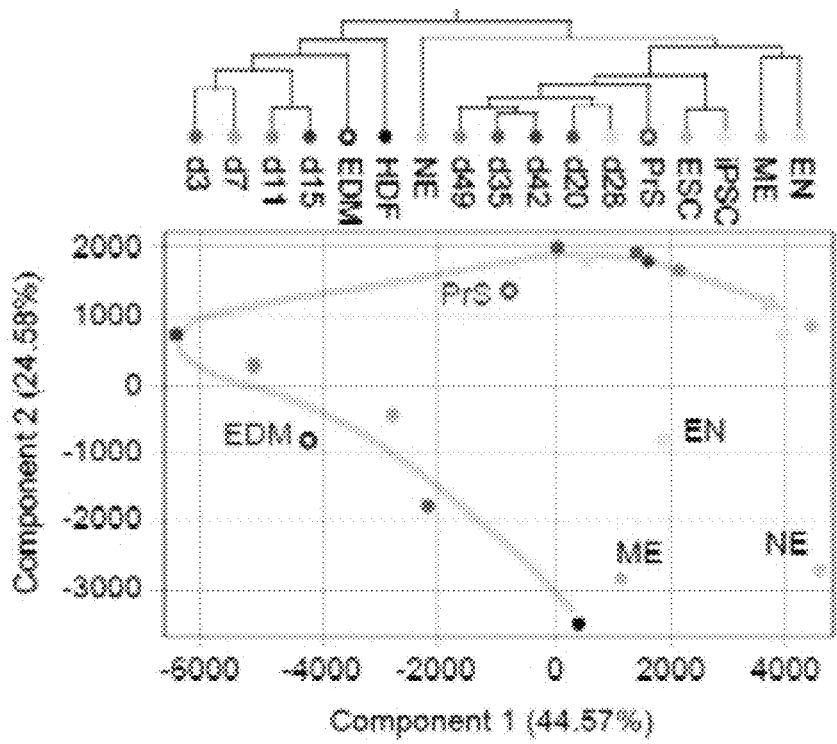
Figure 3D:
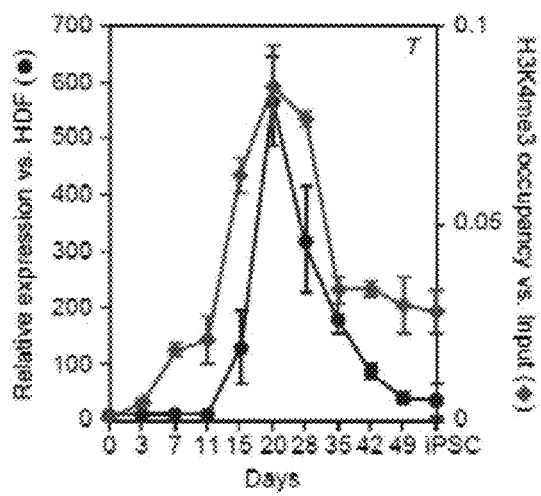
Figure 3E:
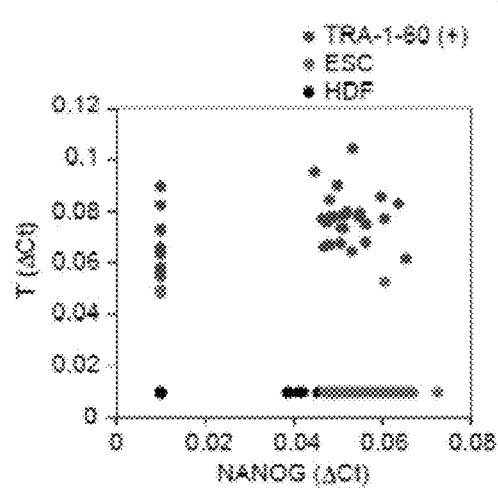
Figure 3F:
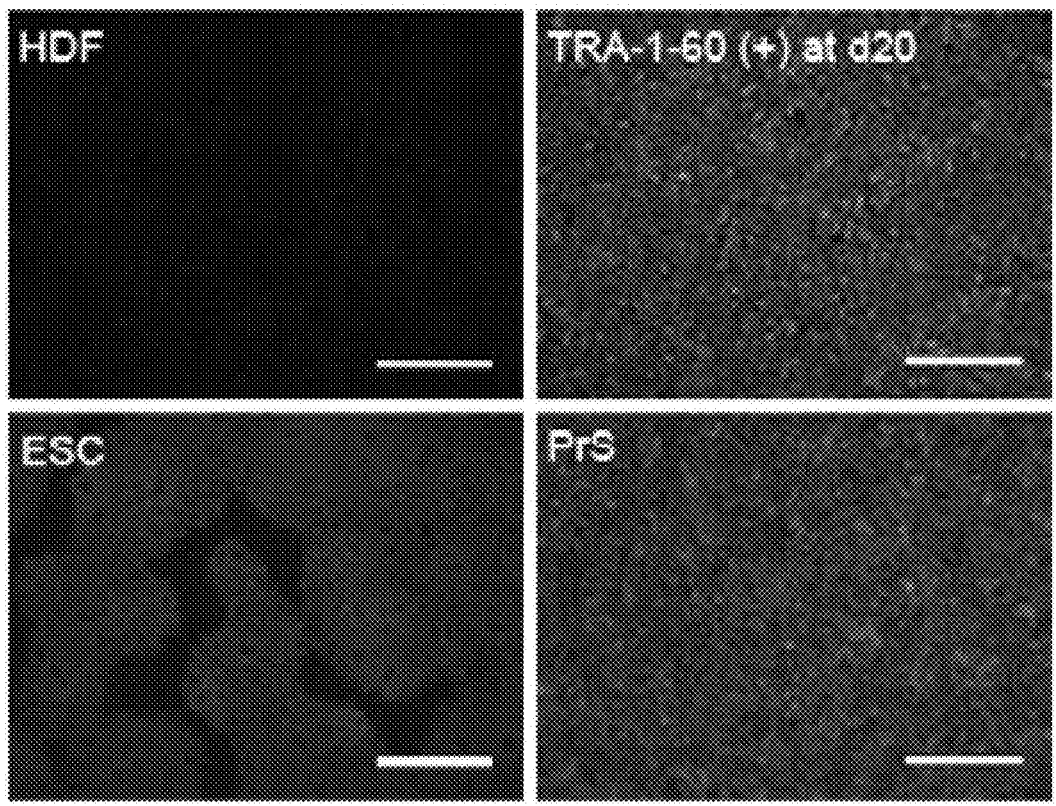
Figure 3G:
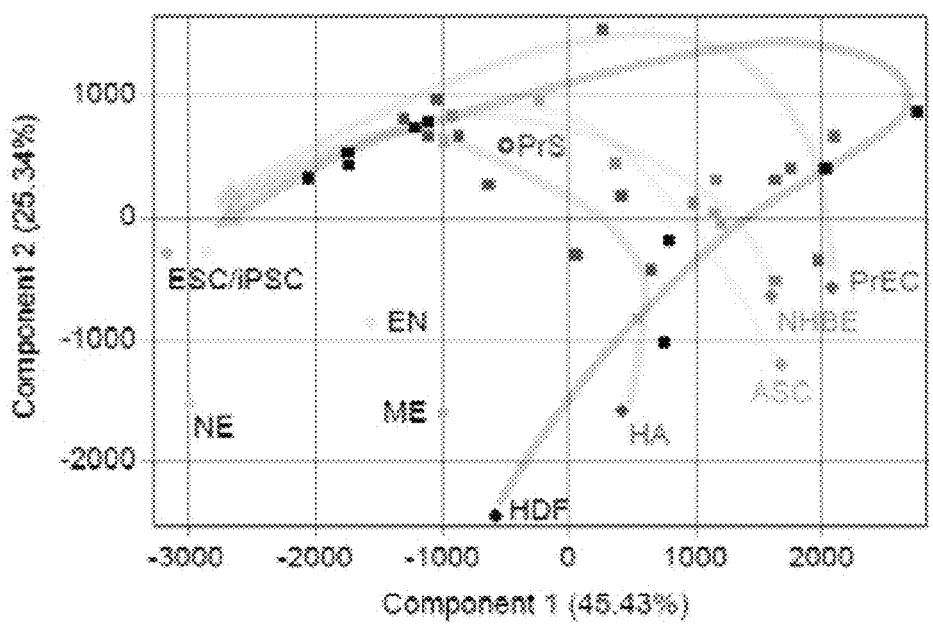
Figure 4C:
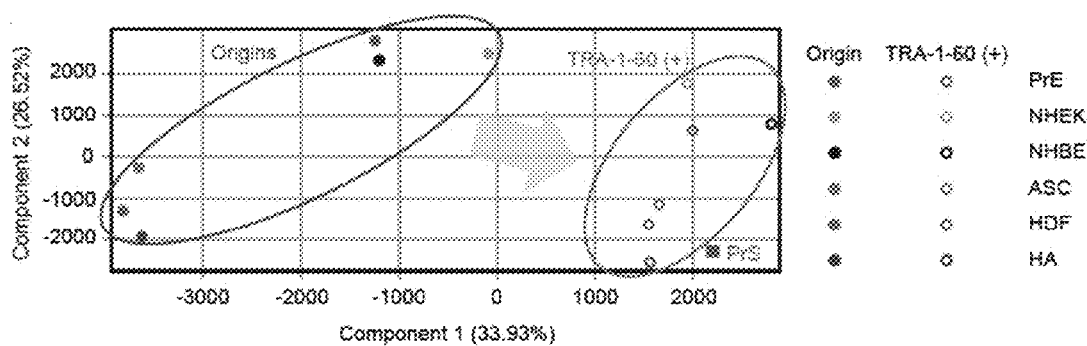

The PCA and hierarchical clustering revealed that TRA-1-60 (+) cells on day 20 post-transduction were more similar but not identical to PrS, than to NE, EN, ME or ESC/iPSC (FIG. 3a). The correlation coefficient of global gene expression between TRA-1-60 (+) cells on day 20 and PrS was 0.9718 which was quite similar level to the clonal variation of ESCs/iPSCs (0.9634-0.9862). The occupancy of tri-methylated lysine 4 of histone H3 (H3K4me3), which is a mark of activated promoter, also transiently increased in PrS-related gene loci during reprogramming (FIG. 3d). Single cell qRT-PCR and immunocytochemistry revealed that vertically all of TRA-1-60 (+) cells on day 20 but not HDFs and ESCs expressed T (FIGS. 3e and 3f). These data suggest that TRA-1-60 (+) cells in late stage of reprogramming possess gene expression profiles partially resembling PrS. TRA-1-60 (+) cells derived from adipose-derived stem cells (ASC), as well as non-mesodermal lineages such as astrocytes (HA, ectoderm), bronchial epithelium (NHBE, endoderm), and prostate epithelial cells (PrEC, endoderm), also showed similarities in global gene expression with PrS (FIGS. 3g and 4c).

GLIS1 has a PrS Induction Activity

Figure 5A:
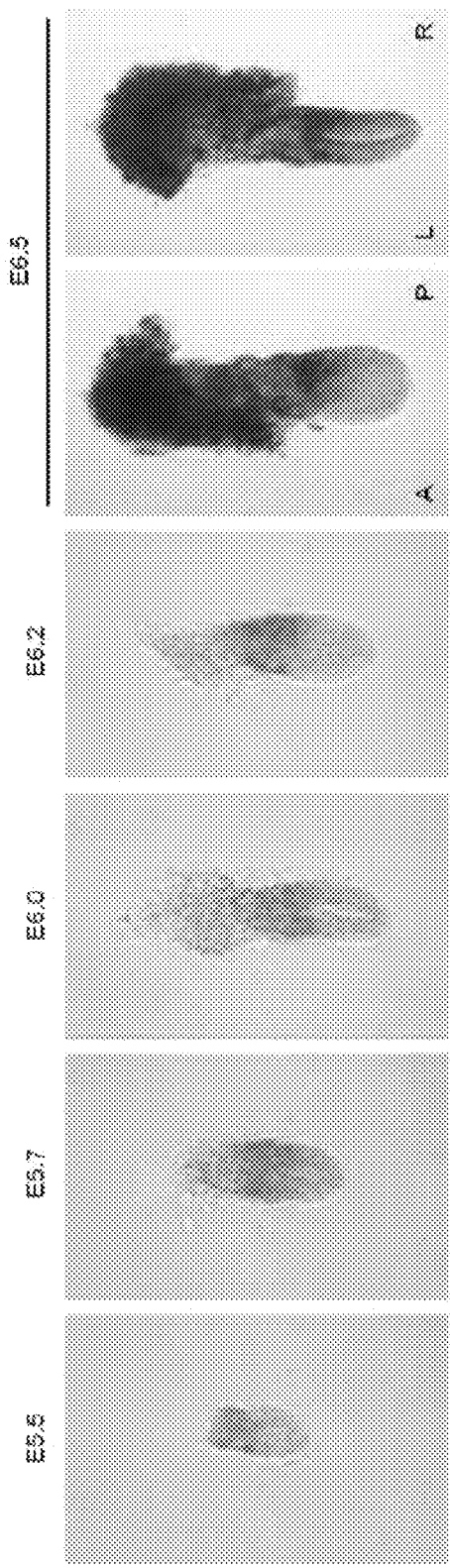
Figure 5B:
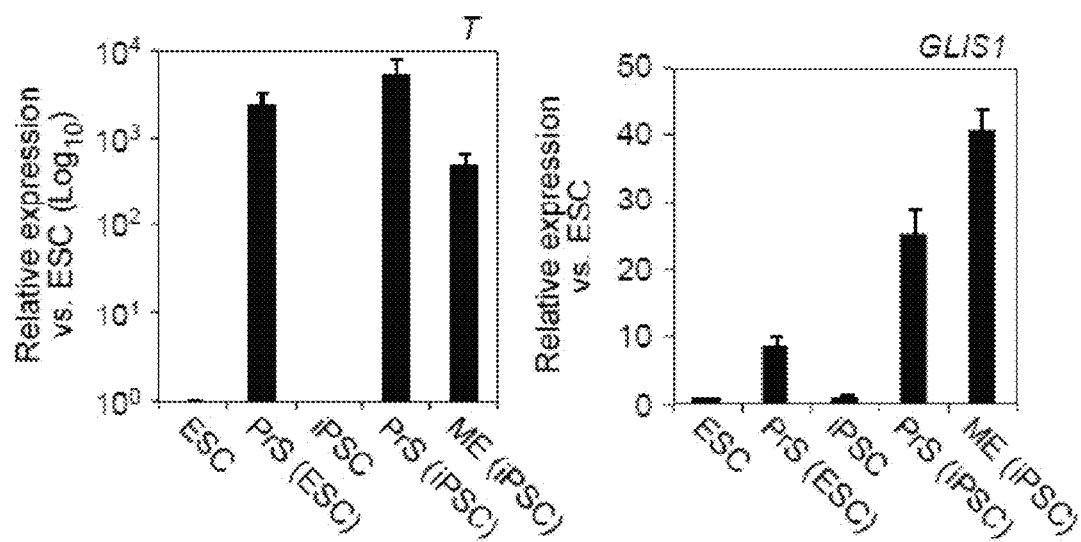

Another set of evidence connecting reprogramming and PrS arose from GLIS1, which we recently reported as a maternal transcription factor enhancing iPSC generation. We found, in this study, GLIS1 is also expressed in a proximal region of epiblast at embryonic day (E) 5.5 and in mesoderm, extraembryonic ectoderm, and PrS including node at E6.5 (FIG. 5a). We also found high expressions of GLIS1 in PrS and mesoendoderm derived from human ESC/iPSC (FIG. 5b). In contrast, Glis1 is barely expressed in undifferentiated human pluripotent stem cells.

Figure 5C:
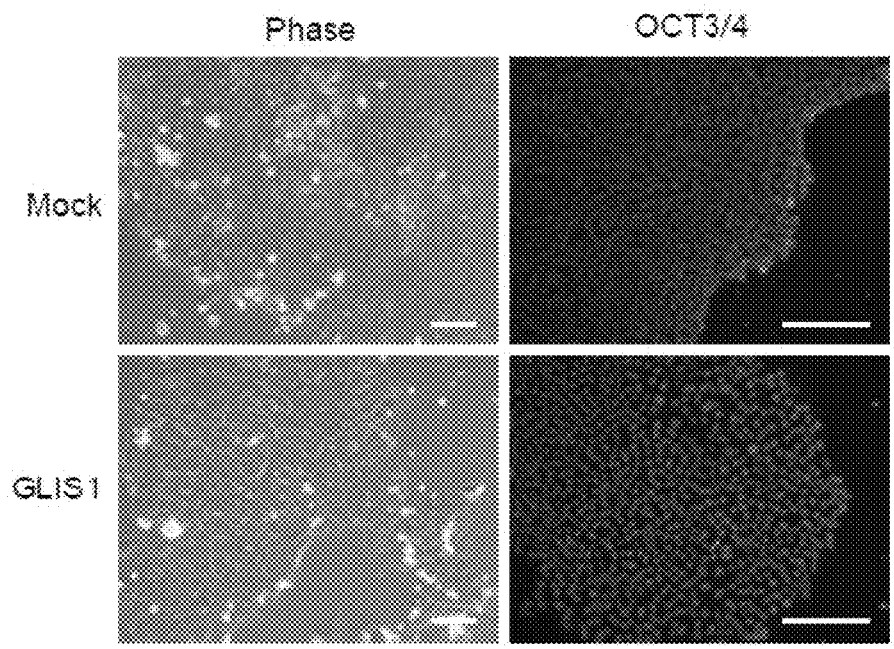
Figure 5D:
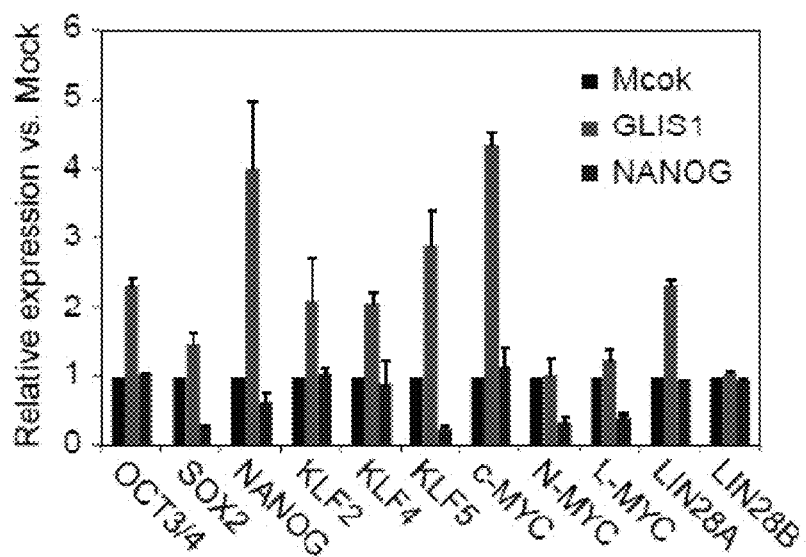
Figure 5E:
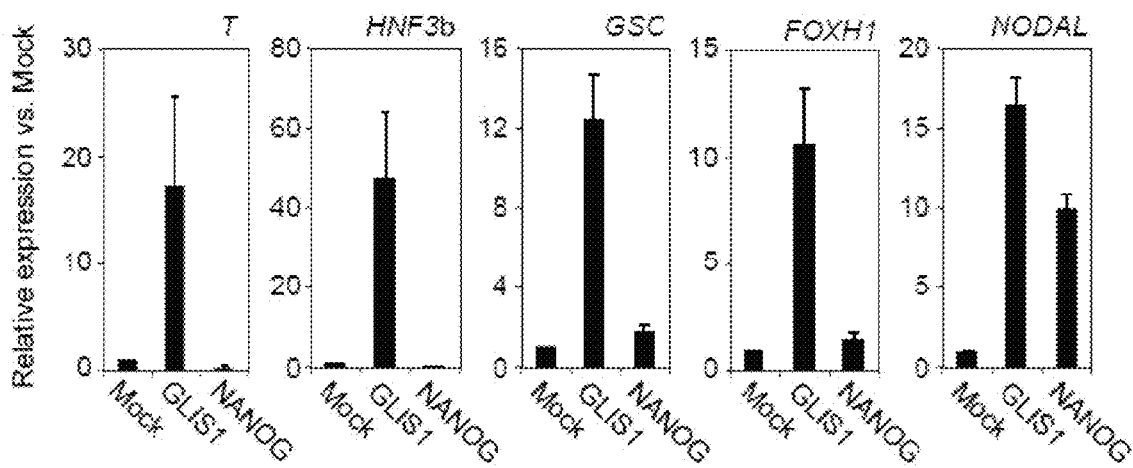
Figure 5F:
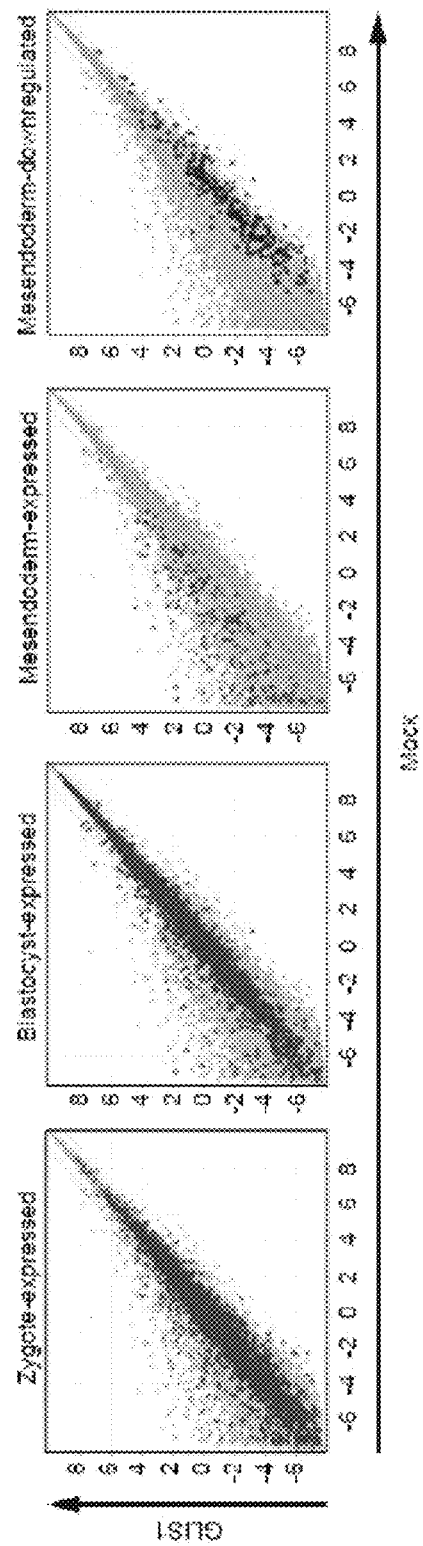
Figure 5G:
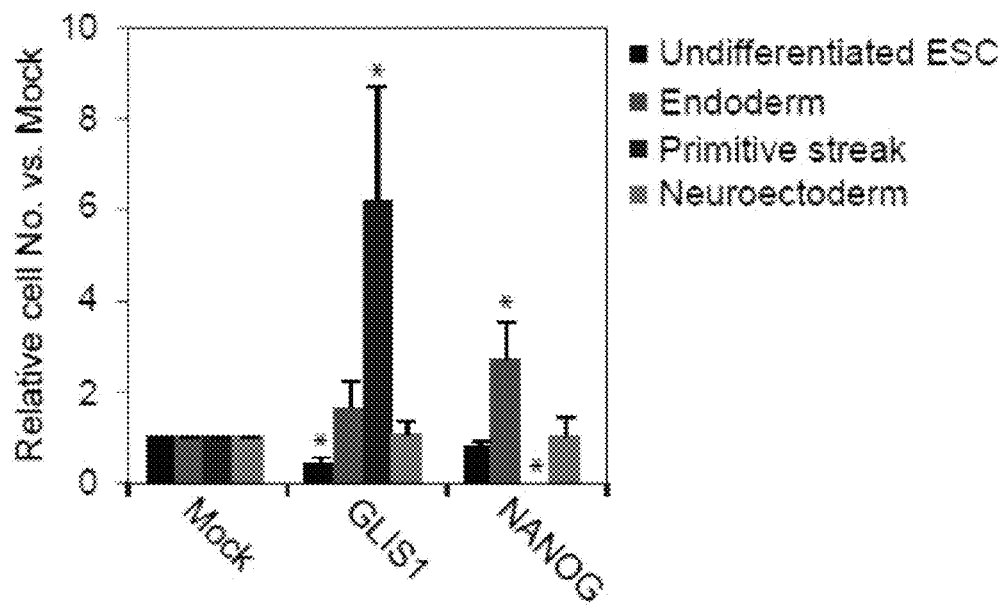

To further examine functions of GLIS1, we introduced an expression vector of GLIS1 into human ESC. We found that forced-expression of GLIS1 in human ESC resulted in morphological changes characterized with looser cell-cell interactions and a slower proliferation rate (FIG. 5c). In consistent with our previous report, GLIS1 enhanced expression of pluripotency-related genes, including OCT3/4, NANOG, LIN28A and c-MYC (FIG. 5d). On the other hand, GLIS1 markedly increased expression of PrS-related genes, such as T, GSC, FOXH1, and NODAL (FIG. 5e). Global gene expression analyses with microarray revealed that GLIS1 significantly activated the expression of meso- and PrS-related genes (106 out of 196 genes, P<0.05) (FIG. 5f). Furthermore, GLIS1 markedly enhanced PrS differentiation potentials of human ESC, whereas reduced neural differentiation (FIG. 5g). These data suggest that the reprogramming enhancer GLIS1 also has a PrS induction activity.

FOXH1 Markedly Enhances Human iPSC Generation

Figure 6A:
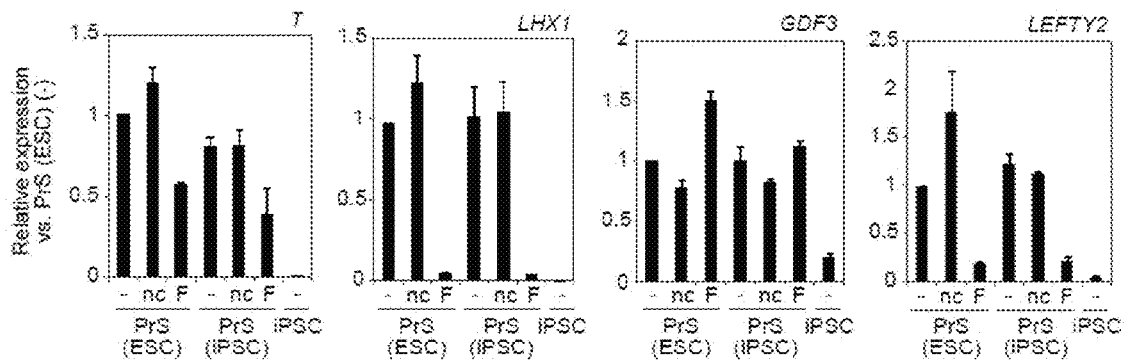

Our findings led us to hypothesize that genes that play important roles in PrS formation during development may facilitate iPSC generation. We initially focused on FOXH1, since knockout mouse experiments have shown that the transcription factor is essential for PrS formation. We confirmed that suppression of FOXH1 prevented the differentiation of human ESC/iPSC into PrS (FIG. 6a).

Figure 6B:
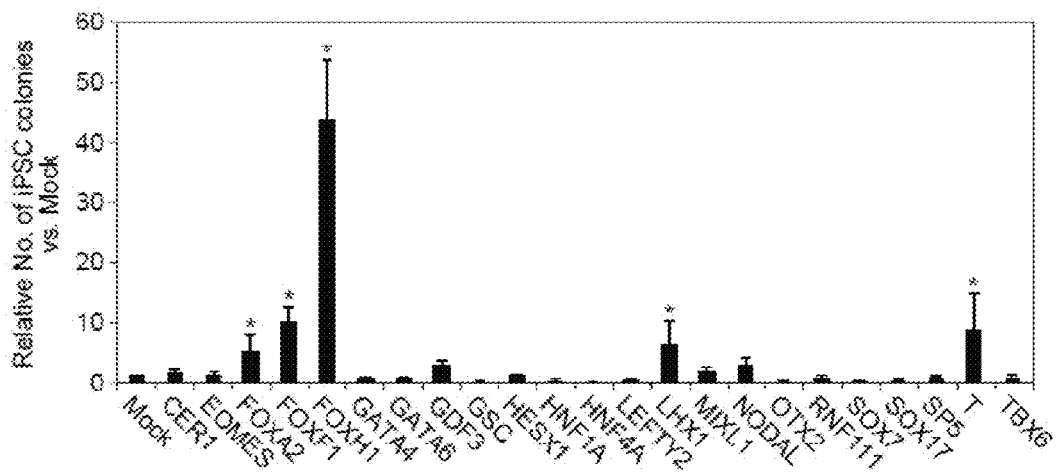

Next, we selected 23 transcription factors that were highly expressed in mesendoderm and transduced each of them together with OSKM into HDFs (FIG. 6b). We found that five factors, including FOXA2, FOXF1, FOXH1, LHX1, and T, significantly increased the numbers of iPSC colonies. Among them, FOXH1 showed the strongest effect (FIG. 6b). FOXH1 functions as a downstream target of the Nodal signal and is required for the specification of anterior PrS.

Figure 6C:
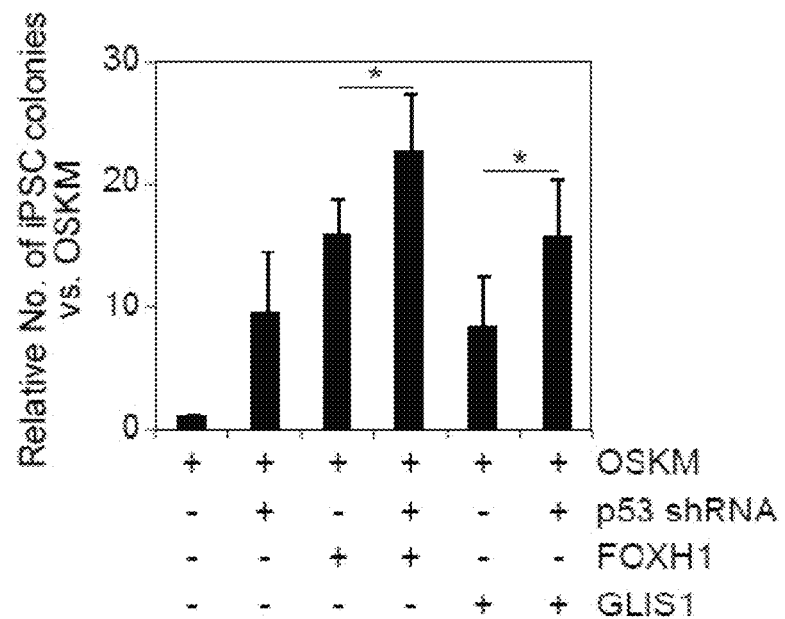

On studying in more detail the effect of markedly increasing the number of iPSC colonies by transduction of FOXH1 along with OSKM (OSKMF), its effect was stronger than short-hairpin RNA mediated depletion of p53 (p53 shRNA) and Glis1, two of the strongest known enhancers of reprogramming (FIG. 6c). FOXH1 and p53 shRNA showed synergistic effects, suggesting that FOXH1 enhances reprogramming independently of p53 activities. We confirmed that human iPSC generated with FOXH1 were indistinguishable from those with OSKM alone (FIG. 7). Taken together, these data suggest that FOXH1 has a strong activity to enhance human iPSC generation.

Figure 6D:
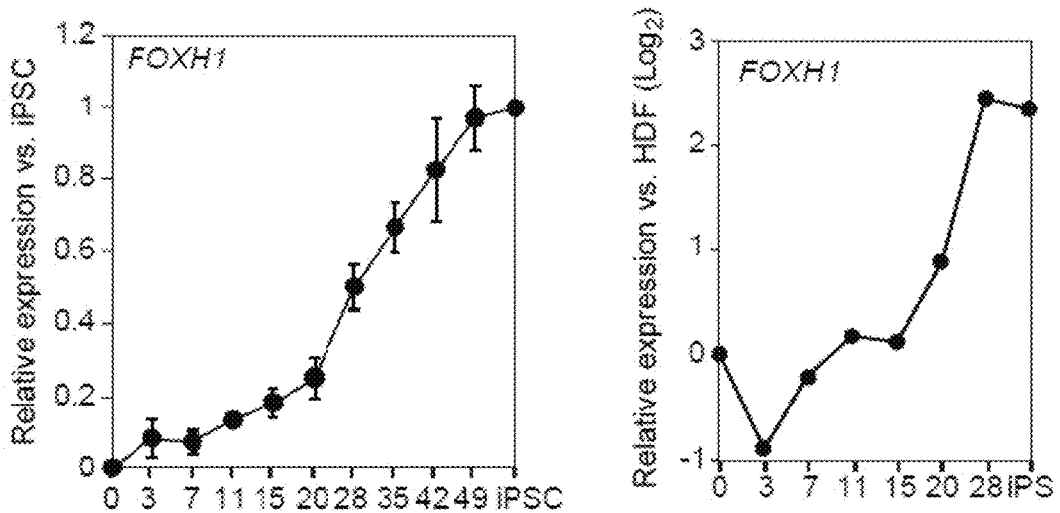
Figure 6E:
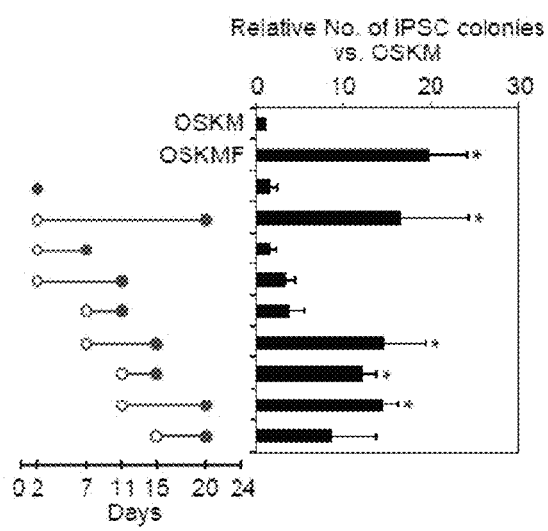
Figure 6F:
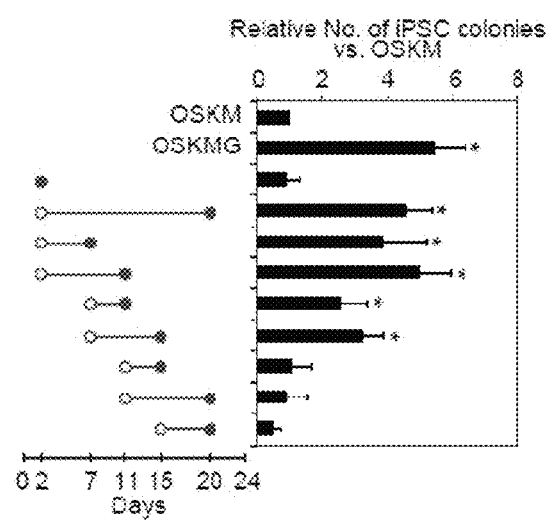
Figure 6G:
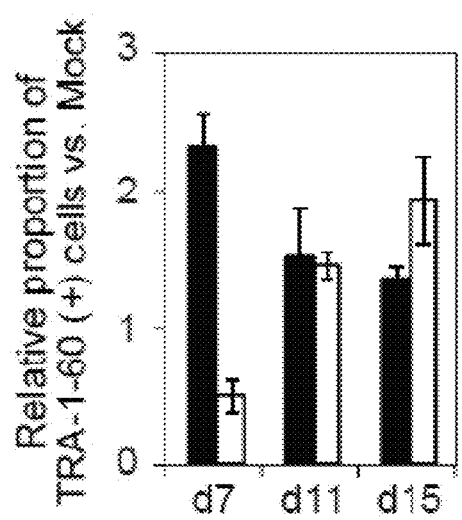
Figure 6H:
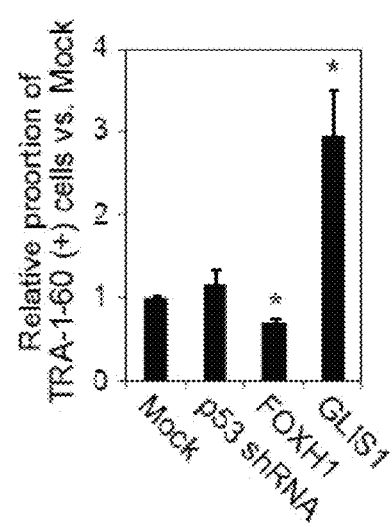
Figure 6I:
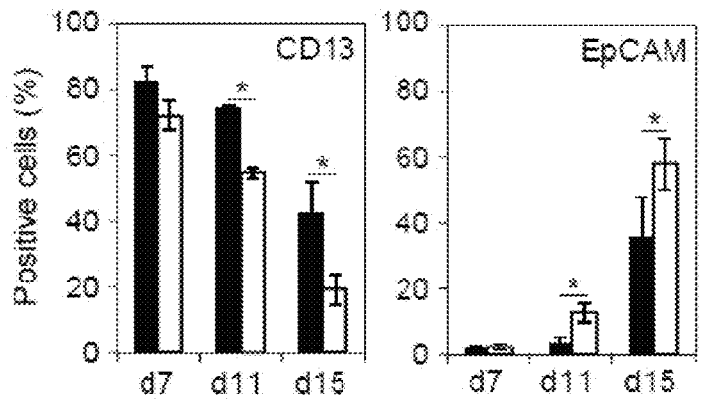
Figure 6J:
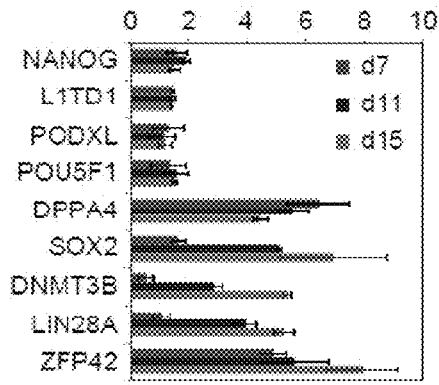

During human iPSC generation, endogenous FOXH1 increased in late stages (FIG. 6d). Stage-specific activation of FOXH1 demonstrated that FOXH1 clearly facilitated reprogramming efficiency in late stages (FIGS. 6e and 6g). These results are in contrast to those using GLIS1, which facilitated reprogramming in the earlier stages and increased the proportion of TRA-1-60 (+) cells (FIGS. 6f and 6g). This may suggest that GLIS1 promotes induction of a PrS-like state whereas FOXH1 promotes its maturation. Actually, the proportion of TRA-1-60 (+) cells were reproducibly reduced by FOXH1 on day 7 but turned back on day 11 and 15 compared to OSKM with GLIS1 (FIG. 6g). In addition, FOXH1 did not increase the proportion of TRA-1-60 (+) cells at day 7 (FIG. 6h). We found that FOXH1 promoted the downregulation of a fibroblast marker, CD13, and the upregulation of an epithelial marker, EpCAM in TRA-1-60 (+) cells on day 11 and 15 (FIG. 6i). In addition, the expression of late reprogramming markers such as DPPA4, DNMT3B, LIN28A, ZFP42 and endogenous SOX2 were significantly enhanced by FOXH1 action (FIG. 6j). These results further support our hypothesis that GLIS1 promotes induction of a PrS-like state whereas FOXH1 promotes its maturation.

Figure 6K:
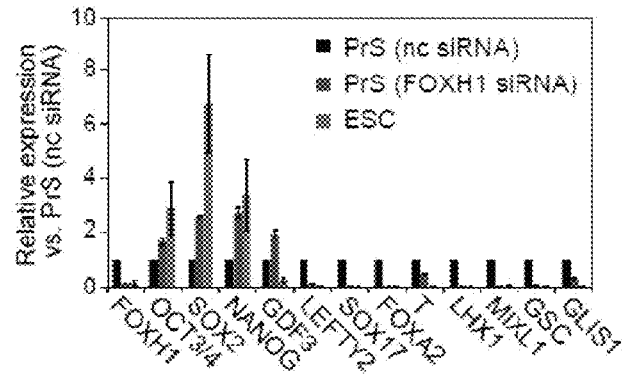
Figure 6L:
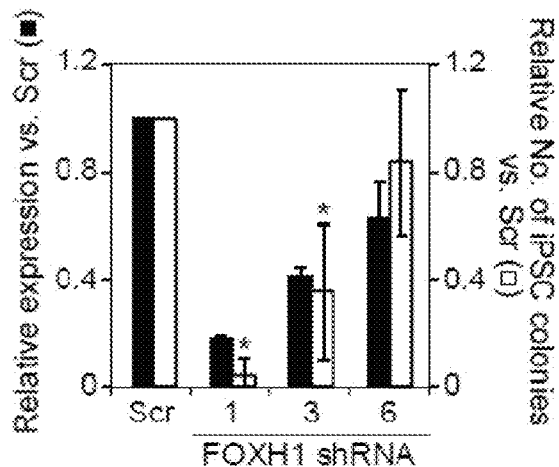
Figure 6M:
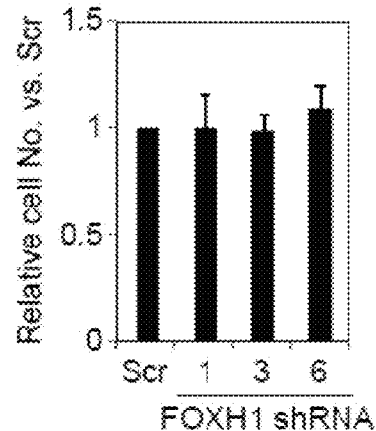
Figure 7A:
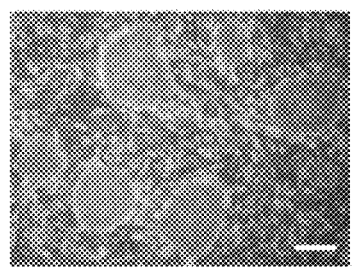
Figure 7B:
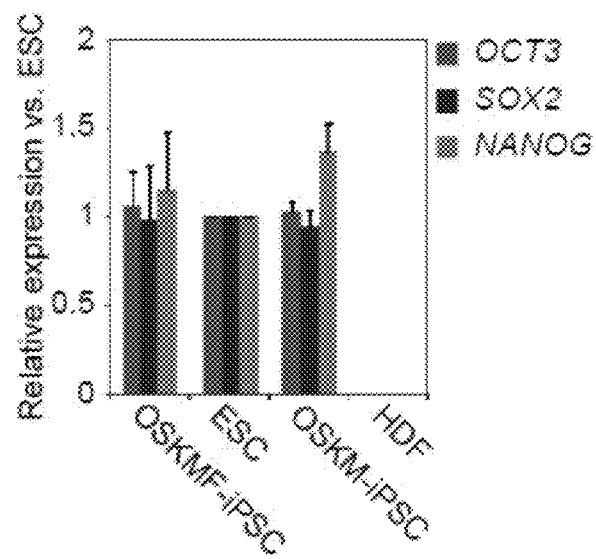
Figure 7C:
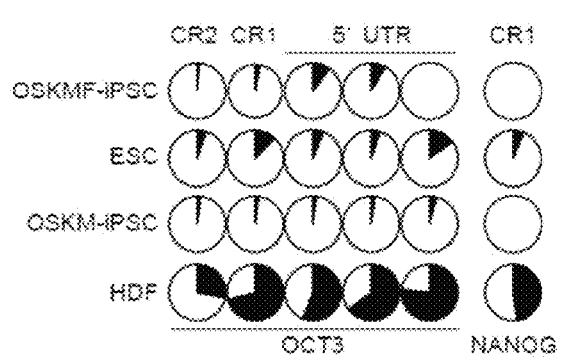
Figure 7D:
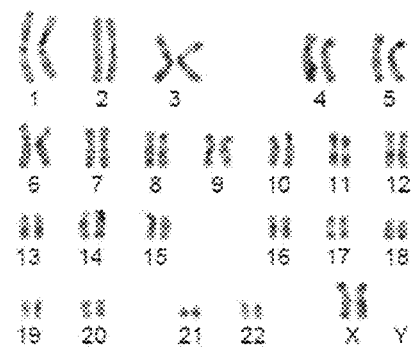
Figure 7E:
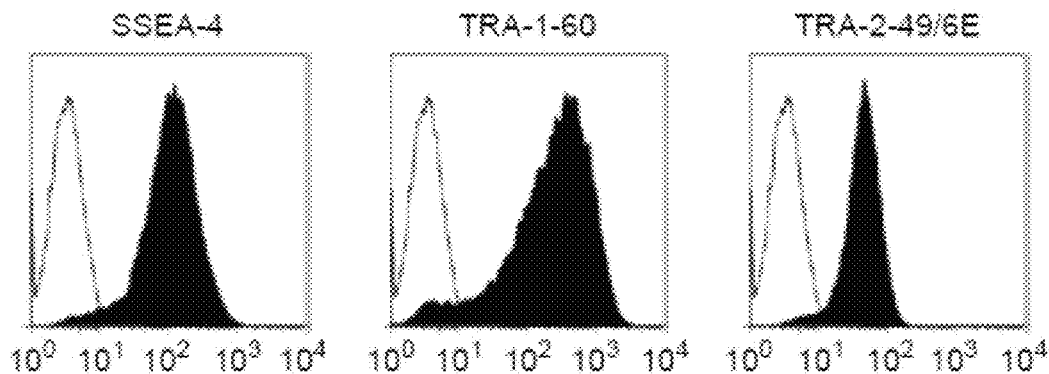
Figure 7F:
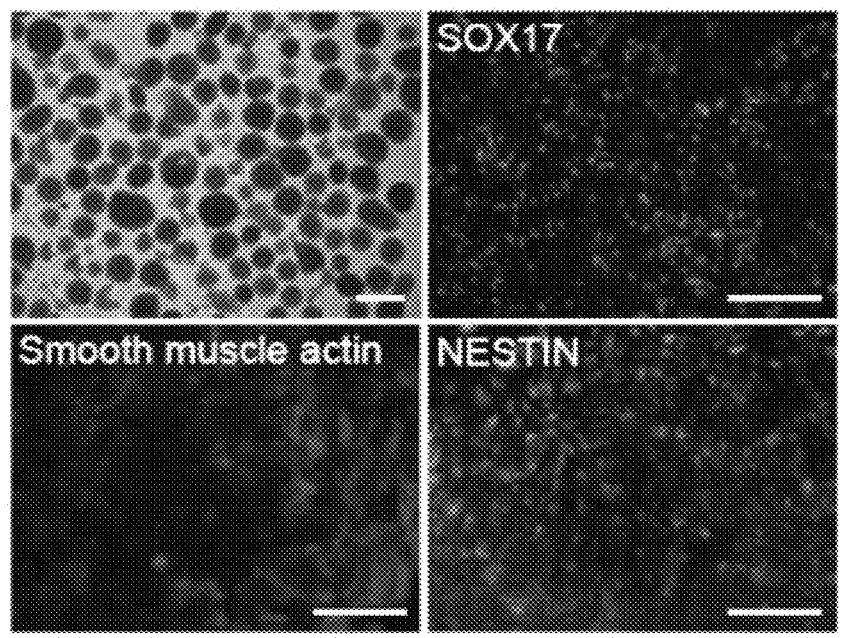
Figure 7G:
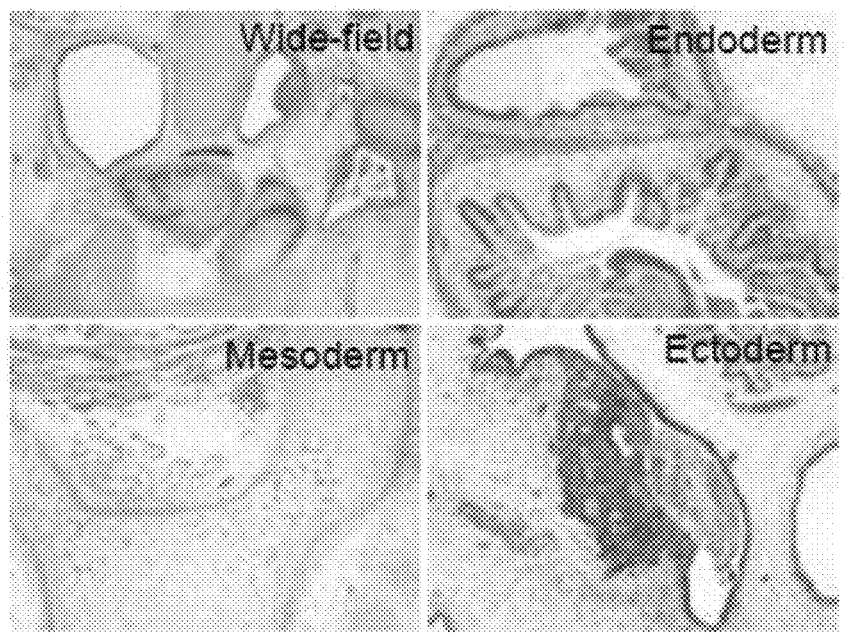

Next, we again examined whether the endogenous FOXH1 is required for human iPSC generation and PrS differentiation in more detail. Knockdown of FOXH1 in ESC significantly interfered the differentiation into PrS (FIG. 6k). The expression of endogenous FOXH1 was ever-increased in TRA-1-60 (+) cells during reprogramming toward iPSC (FIG. 6d). Three out of six shRNAs (#1, 3 and 6) suppressed the expression of endogenous FOXH1 in ESC or OSKM-transduced HDF with −90%, 70% and 50% efficiencies, respectively (FIG. 6l). When co-introduced with OSKM, shRNA #1 nearly abolished the generation of iPSC colonies (FIG. 6l). In addition, shRNA #3 decreased iPSC colony formation by 50%. In contrast, the suppression of FOXH1 did not ameliorate proliferation of transduced HDFs (FIG. 6m). These data suggest that FOXH1 plays an important role in the reprogramming process toward iPSCs.

A Fox Family Member Enhances Human iPSC Generation

Finally, we examined the effects of other FOX family transcription factors on human iPSC generation. We found that 5 factors such as FOXA2, FOXB1, FOXF1 (same as FOXF2), FOXG1, and FOXH1 out of selected 36 FOX genes significantly increased numbers of iPSC colonies (FIG. 8). As similar to SOX, KLF and MYC families, some of FOX family transcription factors have overlapping effects on human iPSC generation (FIG. 9).

In summary, our analyses of purified nascent reprogrammed cells revealed that the route to induced pluripotency in human goes through a PrS-like state. This led us to demonstrate that FOXH1, one of the key factors for PrS identify, markedly enhances human iPSC generation.

While the present invention has been described with emphasis on preferred embodiments, it is obvious to those skilled in the art that the preferred embodiments can be modified. The present invention intends that the present invention can be embodied by methods other than those described in detail in the present specification. Accordingly, the present invention encompasses all modifications encompassed in the gist and scope of the appended "CLAIMS."

The contents disclosed in any publication cited herein, including patents and patent applications, are hereby incorporated in their entireties by reference, to the extent that they have been disclosed herein.

This application is based on US provisional patent application No. 61/717,250 filed on Oct. 23, 2012, the contents of which are incorporated in full herein.

The invention claimed is:

1. A method of improving induced pluripotent stem (iPS) cell establishment efficiency, comprising contacting a protein involved in primitive streak (PrS) formation or a nucleic acid that encodes the same with a somatic cell in vitro in a nuclear reprogramming step,
   wherein the protein is selected from the group consisting of forkhead box protein h1 (Foxh1), brachyury, Lin-11/Isl-1/Mec-3 homeobox protein 1 (LHX1), forkhead box protein b1 (Foxb1), forkhead box protein f1 (Foxf1), forkhead box protein f2 (Foxf2), and forkhead box protein g1 (Foxg1), and
   wherein the nuclear reprogramming step is performed by introducing nuclear reprogramming substances into the somatic cell, wherein the nuclear reprogramming substances comprise any of the following (a) to (d):
   (a) Oct3/4, Sox2, and Klf4,
   (b) (i) Oct3/4,
       (ii) a member of the Sox family selected from the group consisting of Sox1, Sox2, Sox3, Sox15, Sox17, and Sox18,
       (iii) a member of the Klf family selected from the group consisting of Klf1, Klf2, Klf4, and Klf5, and
       (iv) a member of the Myc family selected from the group consisting of c-Myc, L-Myc, and n-Myc,
   (c) Oct3/4, Sox2, Nanog, and Lin28, and
   (d) nucleic acids that encode any of (a) to (c), wherein (a) to (c) are proteins,
   thereby improving iPS cell establishment efficiency compared to that obtained by introducing the nuclear reprogramming substances alone into the somatic cell.

2. The method according to claim 1, wherein the protein is Foxh1.

3. The method according to claim 1, wherein the somatic cell is further contacted with Glioma-associated oncogene-similar 1 (Glis1) or a nucleic acid that encodes the same and/or a p53 inhibitor in vitro in the nuclear reprogramming step.

4. The method according to claim 1, wherein the protein is brachyury.

5. The method according to claim 1, wherein the protein is LHX1.

6. The method according to claim 1, wherein the protein is Foxb1.

7. The method according to claim 1, wherein the protein is Foxf1.

8. The method according to claim 1, wherein the protein is Foxf2.

9. The method according to claim 1, wherein the protein is Foxg1.

10. The method according to claim 1, wherein the nuclear reprogramming substances are Oct3/4, Sox2, and Klf4 proteins, or nucleic acids that encode Oct3/4, Sox2, and Klf4 proteins.

11. The method according to claim 1, wherein the nuclear reprogramming substances are proteins (i) Oct3/4, (ii) a member of the Sox family selected from the group consisting of Sox1, Sox2, Sox3, Sox15, Sox17 and Sox18, (iii) a member of the Klf family selected from the group consisting of Klf1, Klf2, Klf4, and Klf5, and (iv) a member of the Myc family selected from the group consisting of c-Myc, L-Myc, and n-Myc, or nucleic acids that encode (i)-(iv).

12. The method according to claim 1, wherein the nuclear reprogramming substances are Oct3/4, Sox2, Nanog, and Lin28 proteins, or nucleic acids that encode Oct3/4, Sox2, Nanog, and Lin28 proteins.

* * * * *